United States Patent
Wales et al.

(10) Patent No.: US 7,559,450 B2
(45) Date of Patent: *Jul. 14, 2009

(54) SURGICAL INSTRUMENT INCORPORATING A FLUID TRANSFER CONTROLLED ARTICULATION MECHANISM

(75) Inventors: Kenneth S. Wales, Mason, OH (US); Chad P. Boudreaux, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 253 days.

This patent is subject to a terminal disclaimer.

(21) Appl. No.: 11/061,908

(22) Filed: Feb. 18, 2005

(65) Prior Publication Data

US 2006/0190028 A1 Aug. 24, 2006

(51) Int. Cl.
*A61B 17/10* (2006.01)

(52) U.S. Cl. ............... 227/175.1; 227/176.1; 227/19; 606/143

(58) Field of Classification Search ............... 227/19, 227/175.1, 176.1, 179.1; 606/143
See application file for complete search history.

(56) References Cited

U.S. PATENT DOCUMENTS

| | | | |
|---|---|---|---|
| 3,506,005 A | 4/1970 | Gilio et al. | |
| 4,331,277 A | 5/1982 | Green | |
| 4,485,817 A * | 12/1984 | Swiggett | 227/179.1 |
| 4,488,523 A * | 12/1984 | Shichman | 227/179.1 |
| 4,794,912 A | 1/1989 | Lia | |
| 4,921,482 A | 5/1990 | Hammerslag et al. | |
| 5,005,754 A | 4/1991 | Van Overloop | |
| 5,018,657 A | 5/1991 | Pedlick et al. | |
| 5,179,934 A * | 1/1993 | Nagayoshi et al. | 600/152 |
| 5,197,649 A * | 3/1993 | Bessler et al. | 227/179.1 |
| 5,219,111 A | 6/1993 | Bilotti et al. | |
| 5,250,074 A | 10/1993 | Wilk et al. | |
| 5,275,608 A | 1/1994 | Forman et al. | |
| 5,314,466 A | 5/1994 | Stern et al. | |
| 5,339,723 A | 8/1994 | Huitema | |
| 5,361,583 A | 11/1994 | Huitema | |
| 5,405,344 A | 4/1995 | Williamson et al. | |

(Continued)

FOREIGN PATENT DOCUMENTS

EP          071959          2/1983

(Continued)

OTHER PUBLICATIONS

EPO Search Report, Application No. 06 25 0869, Jun. 19, 2006, pp. 1-4.

(Continued)

*Primary Examiner*—Stephen F Gerrity
(74) *Attorney, Agent, or Firm*—Frost Brown Todd LLC

(57) ABSTRACT

A surgical instrument particularly suited to endoscopic use articulates an end effector by including a fluid transfer articulation mechanism that is proximally controlled. A fluid control, which is attached to a proximal portion, transfers fluid through the elongate shaft through a first fluid passage to a first fluid actuator that responds by articulating an articulation joint. Two opposing fluid actuators may respond to differential fluid transfer to effect articulation. Thereby, design flexibility is achieved by avoiding the design constraints of transferring a mechanical motion through the tight confines of the elongate shaft sufficient to effect articulation.

24 Claims, 32 Drawing Sheets

U.S. PATENT DOCUMENTS

| | | | |
|---|---|---|---|
| 5,411,508 A | 5/1995 | Bessler et al. | |
| 5,411,519 A | 5/1995 | Tovey et al. | |
| 5,456,401 A | 10/1995 | Green et al. | |
| 5,465,895 A | 11/1995 | Knodel et al. | |
| 5,485,952 A | 1/1996 | Fontayne | |
| 5,518,164 A | 5/1996 | Hooven | |
| 5,520,678 A | 5/1996 | Heckele et al. | |
| 5,547,117 A | 8/1996 | Hamblin et al. | |
| 5,562,682 A | 10/1996 | Oberlin et al. | |
| 5,575,799 A * | 11/1996 | Bolanos et al. | 606/139 |
| 5,588,623 A | 12/1996 | Leduc | |
| 5,620,649 A | 4/1997 | Trotta | |
| 5,632,433 A | 5/1997 | Grant et al. | |
| 5,662,662 A | 9/1997 | Bishop et al. | |
| 5,669,544 A * | 9/1997 | Schulze et al. | 227/176.1 |
| 5,673,840 A | 10/1997 | Schulze et al. | |
| 5,673,841 A | 10/1997 | Schulze et al. | |
| 5,690,269 A | 11/1997 | Bolanos et al. | |
| 5,692,668 A | 12/1997 | Schulze et al. | |
| 5,702,408 A | 12/1997 | Wales et al. | |
| 5,743,456 A | 4/1998 | Jones et al. | |
| 5,752,973 A | 5/1998 | Kieturakis | |
| 5,779,727 A | 7/1998 | Orejola | |
| 5,797,537 A | 8/1998 | Oberlin et al. | |
| 5,826,776 A * | 10/1998 | Schulze et al. | 227/176.1 |
| 5,829,662 A | 11/1998 | Allen et al. | |
| 5,865,361 A | 2/1999 | Milliman et al. | |
| 5,901,895 A | 5/1999 | Heaton et al. | |
| 5,918,791 A | 7/1999 | Sorrentino et al. | |
| 6,010,054 A | 1/2000 | Johnson et al. | |
| 6,460,749 B1 | 10/2002 | Levinson et al. | |
| 6,485,406 B1 | 11/2002 | Ziegler et al. | |
| 6,485,409 B1 | 11/2002 | Voloshin et al. | |
| 6,488,197 B1 | 12/2002 | Whitman | |
| 6,506,202 B1 | 1/2003 | Dutta et al. | |
| 6,666,854 B1 | 12/2003 | Lange | |
| 6,667,825 B2 | 12/2003 | Lu et al. | |
| 6,715,259 B2 | 4/2004 | Johnston et al. | |
| 6,755,338 B2 | 6/2004 | Hahnen et al. | |
| 6,756,094 B1 | 6/2004 | Wang et al. | |
| 6,786,382 B1 | 9/2004 | Hoffman | |
| 6,830,174 B2 * | 12/2004 | Hillstead et al. | 227/175.1 |
| 6,905,057 B2 | 6/2005 | Swayze et al. | |
| 6,951,675 B2 | 10/2005 | Chin et al. | |
| 6,953,139 B2 | 10/2005 | Milliman et al. | |
| 6,978,921 B2 | 12/2005 | Shelton, IV et al. | |
| 7,087,052 B2 | 8/2006 | Sampson et al. | |
| 7,100,949 B2 | 9/2006 | Williams et al. | |
| 7,111,769 B2 | 9/2006 | Wales et al. | |
| 7,112,357 B2 | 9/2006 | Miller et al. | |
| 7,166,077 B2 | 1/2007 | Millay et al. | |
| 7,213,736 B2 | 5/2007 | Wales et al. | |
| 7,380,696 B2 | 6/2008 | Shelton, IV et al. | |
| 7,407,074 B2 | 8/2008 | Ortiz et al. | |
| 7,410,086 B2 | 8/2008 | Ortiz et al. | |
| 2003/0011507 A1 | 1/2003 | Kondo et al. | |
| 2003/0045900 A1 | 3/2003 | Hahnen et al. | |
| 2003/0111507 A1 | 6/2003 | Nunez | |
| 2004/0002726 A1 | 1/2004 | Nunez et al. | |
| 2004/0108357 A1 | 6/2004 | Milliman et al. | |
| 2004/0173659 A1 | 9/2004 | Green et al. | |
| 2004/0179244 A1 | 9/2004 | Lai et al. | |
| 2004/0232196 A1 | 11/2004 | Shelton et al. | |
| 2004/0232197 A1 | 11/2004 | Shelton et al. | |
| 2004/0232201 A1 | 11/2004 | Wenchell et al. | |
| 2004/0243176 A1 * | 12/2004 | Hahnen et al. | 606/205 |
| 2005/0006429 A1 | 1/2005 | Wales et al. | |
| 2005/0006430 A1 | 1/2005 | Wales | |
| 2005/0006432 A1 | 1/2005 | Racenet et al. | |
| 2005/0006434 A1 | 1/2005 | Wales et al. | |
| 2005/0070958 A1 | 3/2005 | Swayze et al. | |
| 2005/0107824 A1 * | 5/2005 | Hillstead et al. | 606/205 |
| 2005/0165415 A1 | 7/2005 | Wales | |
| 2006/0011699 A1 | 1/2006 | Olson et al. | |
| 2006/0016853 A1 | 1/2006 | Racenet | |
| 2006/0022014 A1 | 2/2006 | Shelton, IV et al. | |
| 2006/0022015 A1 | 2/2006 | Shelton, IV et al. | |
| 2006/0025809 A1 | 2/2006 | Shelton, IV | |
| 2006/0025817 A1 | 2/2006 | Ortiz et al. | |
| 2006/0041273 A1 | 2/2006 | Ortiz et al. | |
| 2006/0025813 A1 | 3/2006 | Shelton et al. | |
| 2006/0047307 A1 | 3/2006 | Ortiz et al. | |
| 2006/0047308 A1 * | 3/2006 | Ortiz et al. | 606/219 |
| 2006/0089535 A1 | 4/2006 | Raz et al. | |
| 2006/0190028 A1 | 8/2006 | Wales et al. | |
| 2006/0190032 A1 | 8/2006 | Wales | |
| 2006/0226196 A1 | 10/2006 | Hueil et al. | |
| 2006/0229665 A1 | 10/2006 | Wales et al. | |
| 2006/0289600 A1 * | 12/2006 | Wales et al. | 227/175.1 |
| 2007/0027468 A1 | 2/2007 | Wales et al. | |

FOREIGN PATENT DOCUMENTS

| | | |
|---|---|---|
| EP | 0 324 635 | 7/1989 |
| EP | 0 598 976 | 6/1994 |
| EP | 0769273 | 4/1997 |
| EP | 0807409 | 11/1997 |
| EP | 0 603 472 | 6/2004 |
| EP | 1495726 | 1/2005 |
| EP | 1 522 263 | 4/2005 |
| EP | 0717959 | 2/2006 |
| EP | 1627605 | 2/2006 |
| EP | 1693008 | 8/2006 |
| WO | WO 01/93766 | 12/2001 |
| WO | WO 03/013374 | 2/2003 |
| WO | WO 03/101313 | 12/2003 |
| WO | WO 2004/002327 | 1/2004 |
| WO | WO 2004/006980 | 1/2004 |
| WO | WO 2004/032762 | 4/2004 |
| WO | WO 2004/112618 | 12/2004 |

OTHER PUBLICATIONS

EPO Search Report, Application No. 06253759.2, Nov. 24, 2006, pp. 1-5.
Australian Search Report for Application No. SG 200600909-6, dated Mar. 2, 2007.
Australian Search Report for Application No. SG 200601987-1, dated Feb. 8, 2007.
Danish Search Report for Application No. 200601986-3, dated Apr. 11, 2007.
European Search Report dated Aug. 8, 2007 for EPO Application No. 06251959.
European Search Report dated Jul. 19, 2007 for EPO Application No. 06253226.
European Search Report dated Aug. 21, 2007 for EPO Application No. 06254005.
Notice of Allowance dated Nov. 15, 2006 for U.S. Appl. No. 11/100,847.
Office Action dated Jun. 1, 2006 for U.S. Appl. No. 11/100,847.
Office Action dated Sep. 27, 2006 for U.S. Appl. No. 11/165,094.
Office Action dated Mar. 29, 2007 for U.S. Appl. No. 11/165,094.
Office Action dated Jun. 26, 2007 for U.S. Appl. No. 11/239,528.
Office Action dated Aug. 1, 2007 for U.S. Appl. No. 11/100,847.
Office Action dated Aug. 23, 2007 for U.S. Appl. No. 11/165,094.
Office Action dated Sep. 7, 2007 for U.S. Appl. No. 11/238,358.
European Search Report dated Nov. 23, 2007 for EPO Application 06253224.
Office Action dated Apr. 5, 2007 for U.S. Appl. No. 11/239,528.
Office Action dated Jan. 14, 2008 for U.S. Appl. No. 11/239,528.
Notice of Allowance dated Jun. 26, 2008 for U.S. Appl. No. 11/165,094.
Notice of Allowance dated Jul. 31, 2008 for U.S. Appl. No. 11/238,358.
Final Rejection dated Feb. 25, 2008 for U.S. Appl. No. 11/165,094.

Final Rejection dated Mar. 26, 2008 for U.S. Appl. No. 11/238,358.
Non-Final Rejection dated Apr. 7, 2008 for U.S. Appl. No. 11/165,468.
Non-Final Rejection dated Jul. 11, 2008 for U.S. Appl. No. 11/239,528.
Non-Final Rejection dated Jul. 17, 2008 for U.S. Appl. No. 11/100,772.
Office Action dated Jun. 4, 2007 for U.S. Appl. No. 11/165,094.
European Search Report dated Nov. 20, 2006 for Application No. 06254005.9.
EPO Search Report dated Jul. 28, 2006 for Application No. 06253224.
EPO Search Report dated Aug. 31, 2006 for Application No. 06253226.
EPO Search Report dated Nov. 20, 2006 for Application No. 06254005.
EPO Search Report dated May 5, 2008 for Application No. 06251960.

* cited by examiner

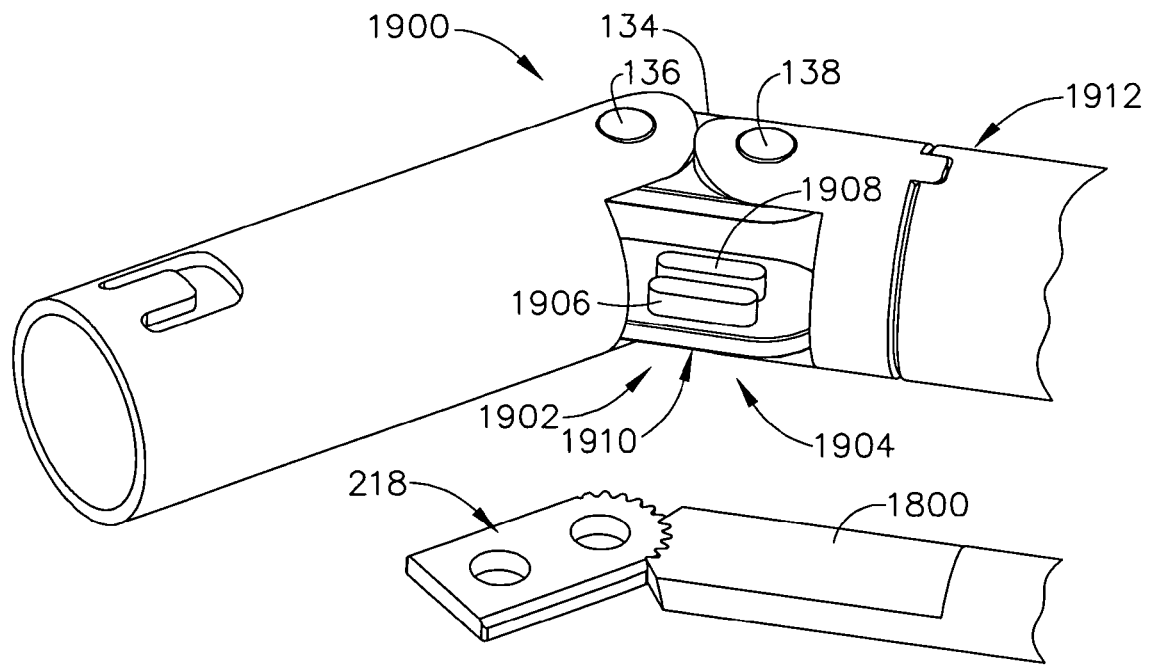
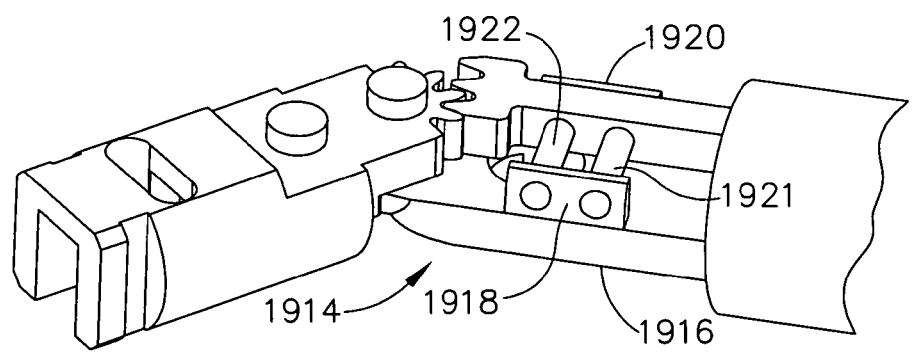
FIG. 9

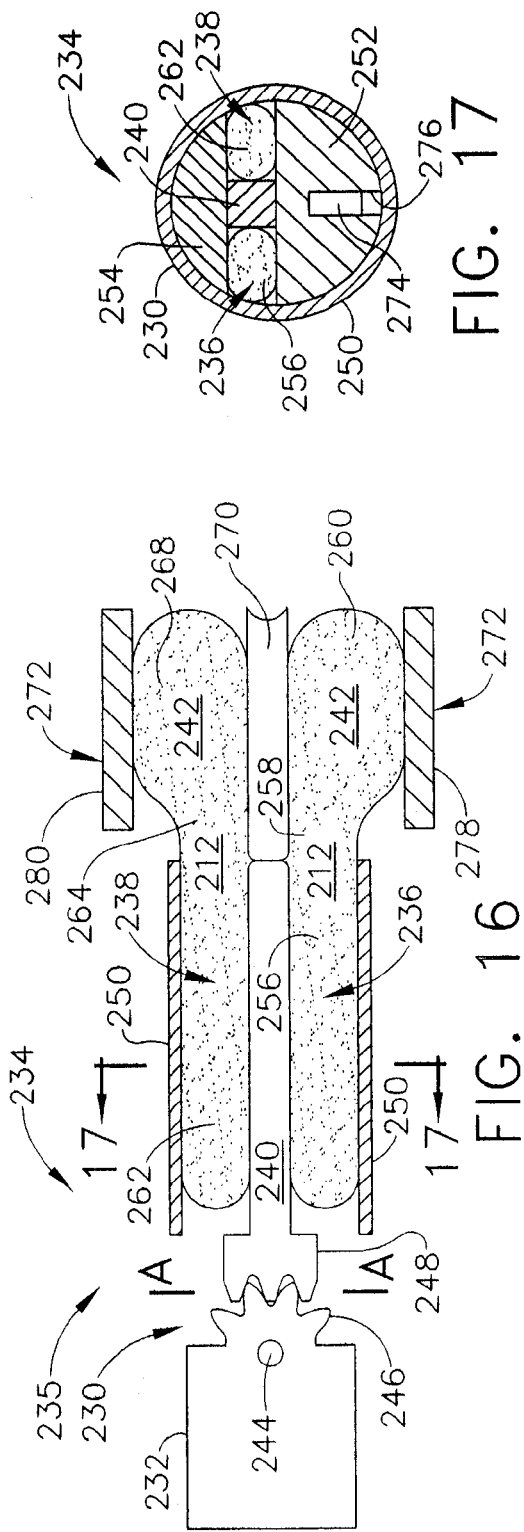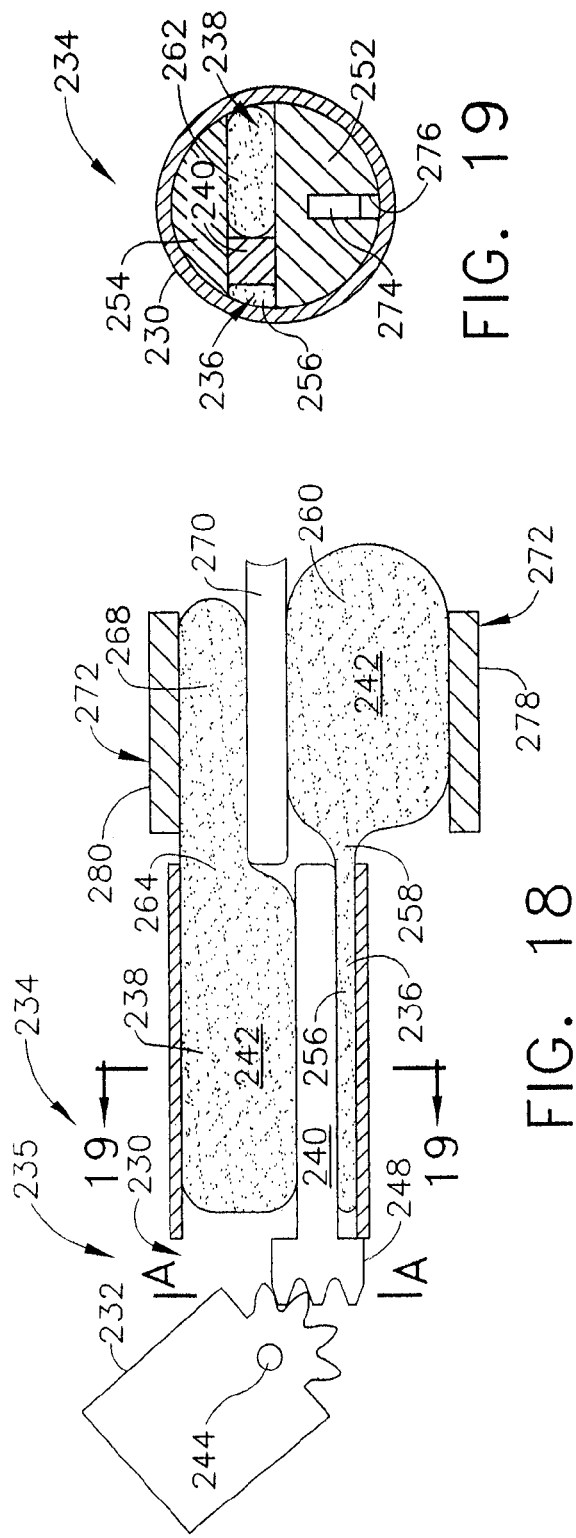

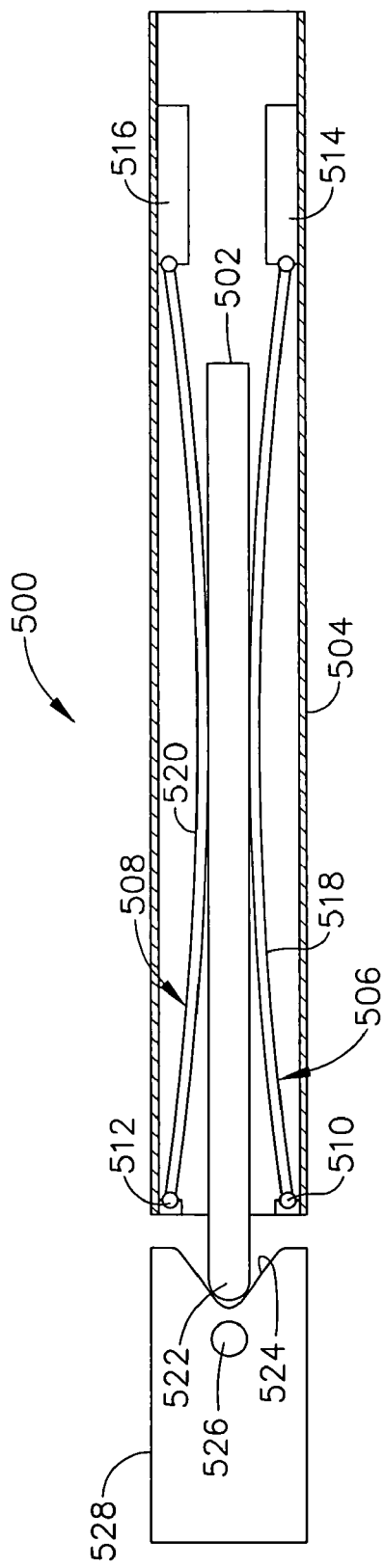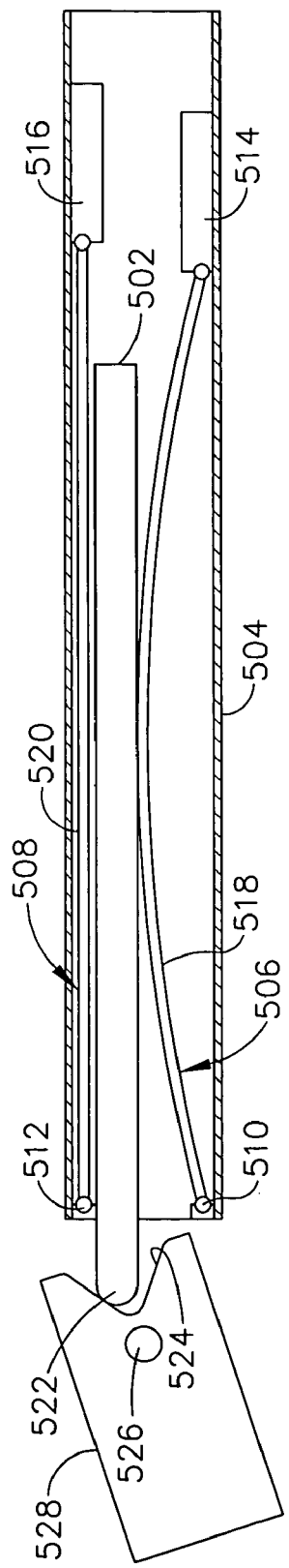

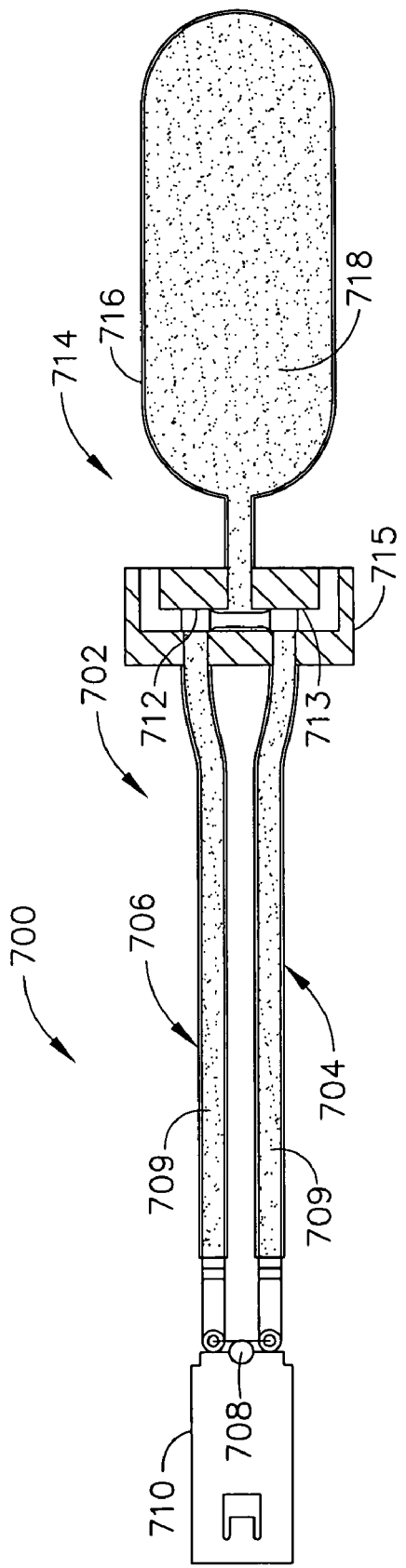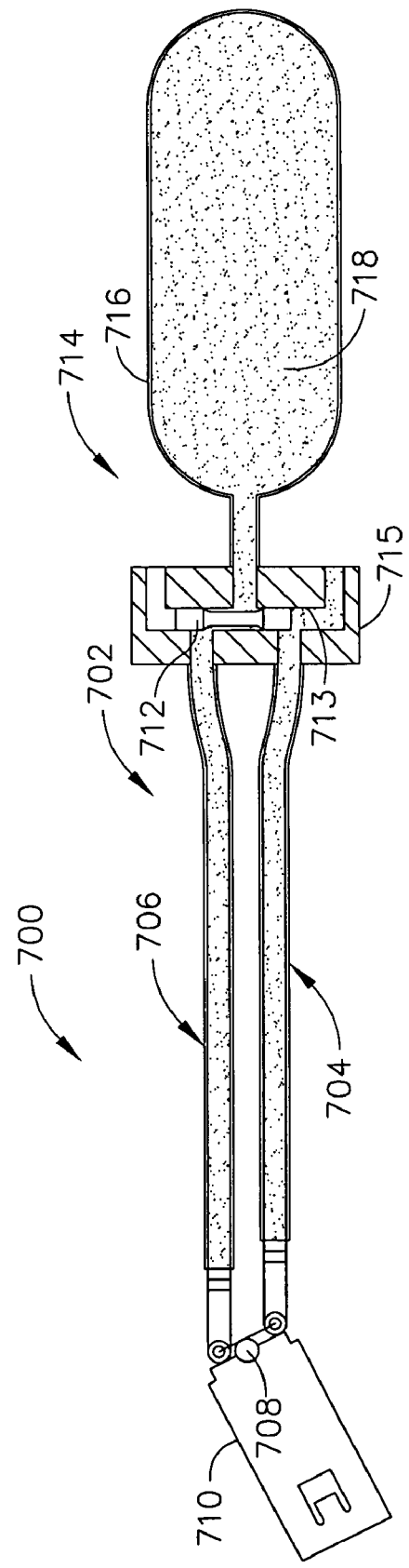
FIG. 28
FIG. 29

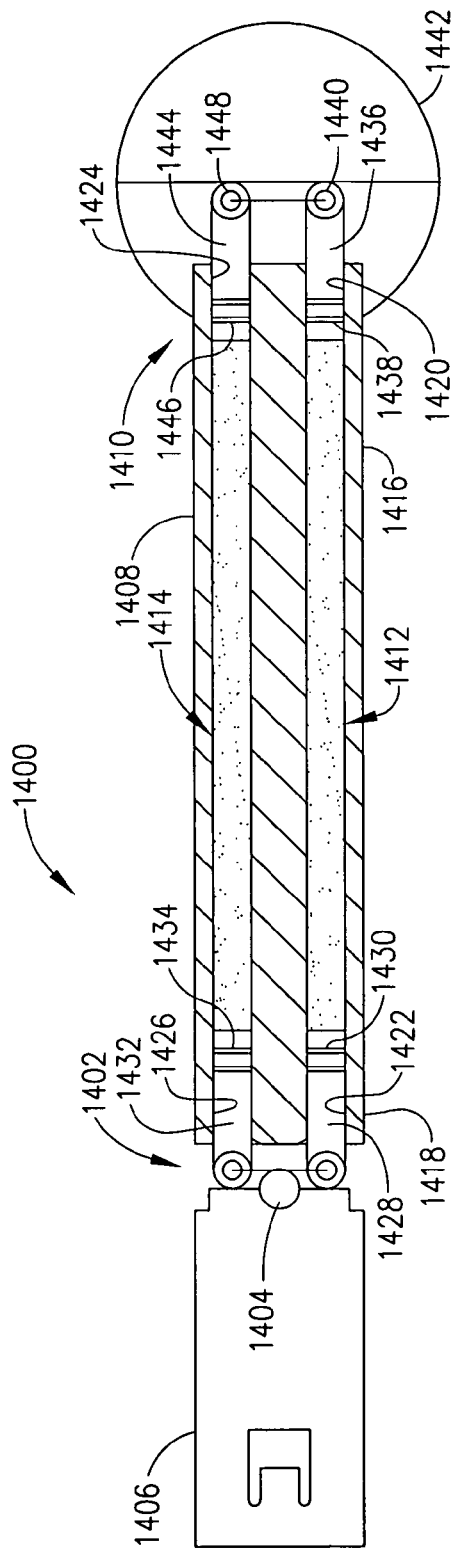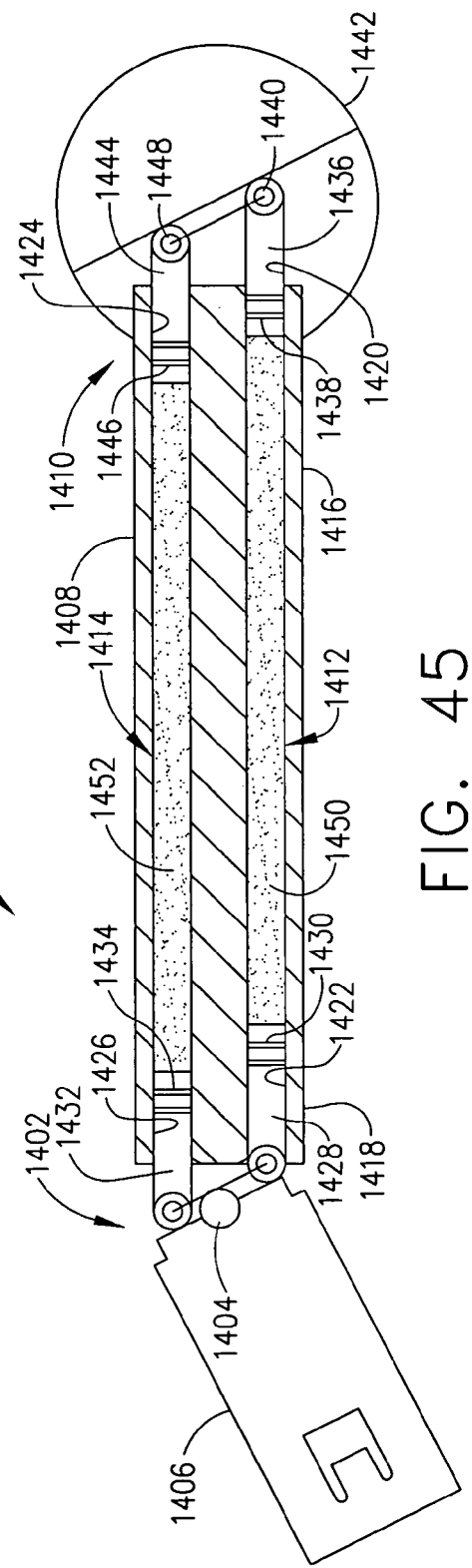
FIG. 44
FIG. 45

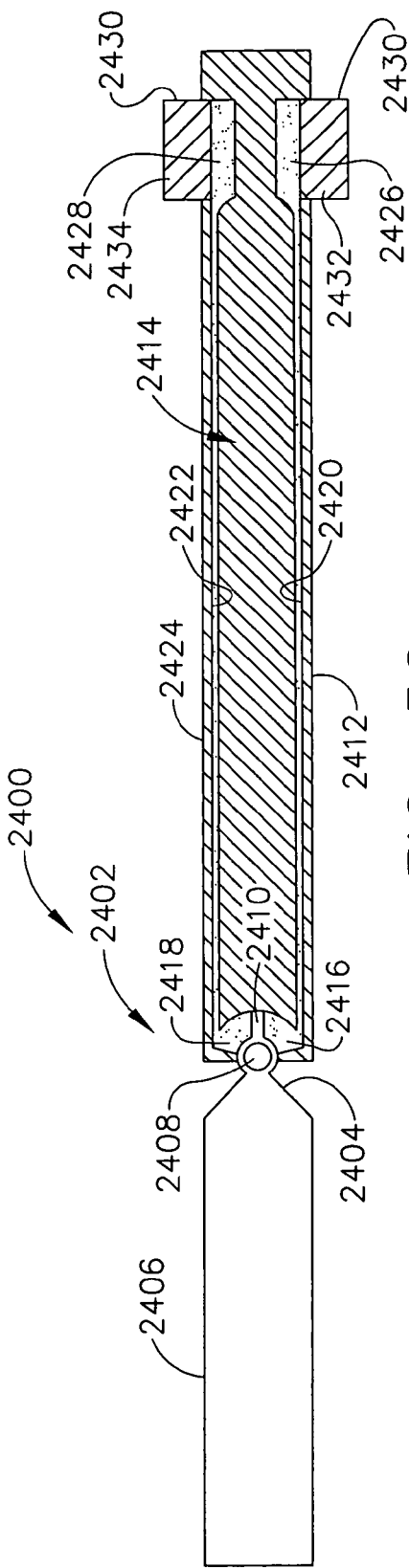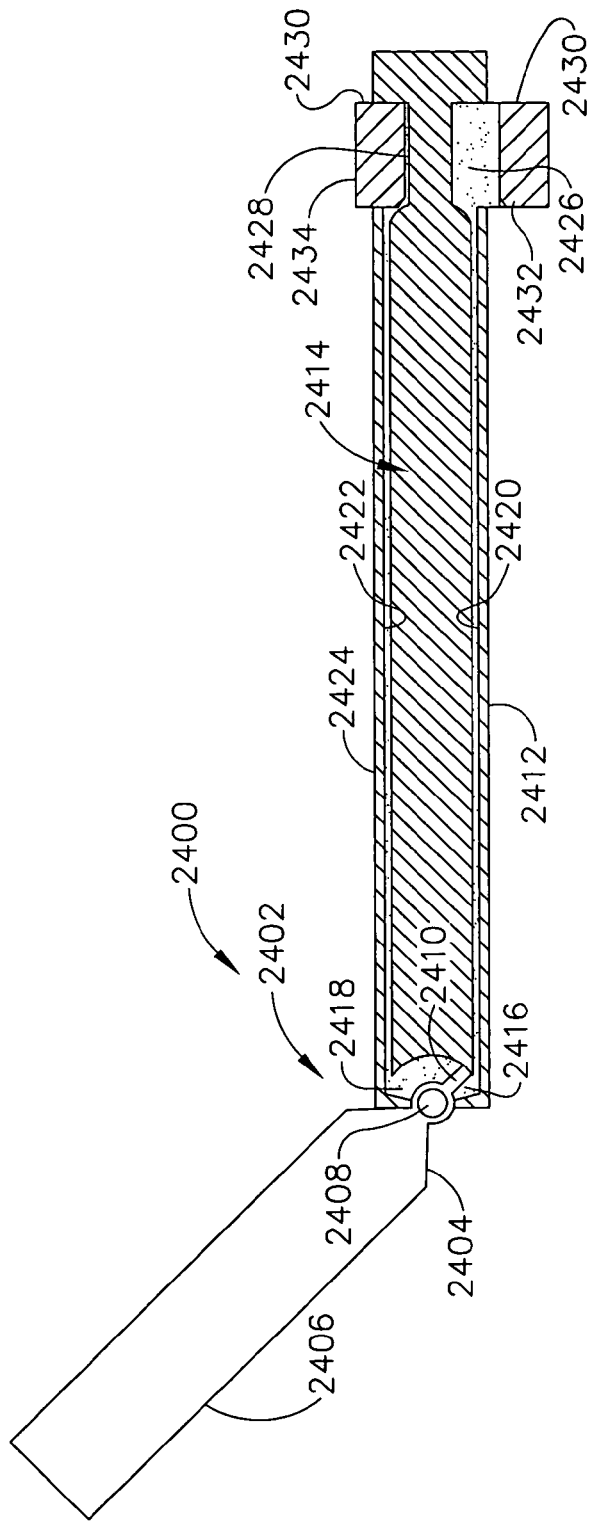

SURGICAL INSTRUMENT INCORPORATING A FLUID TRANSFER CONTROLLED ARTICULATION MECHANISM

FIELD OF THE INVENTION

The present invention relates in general to surgical instruments that are suitable for endoscopically inserting an end effector (e.g., endocutter, grasper, cutter, staplers, clip applier, access device, drug/gene therapy delivery device, and an energy device using ultrasound, RF, laser, etc.) to a surgical site, and more particularly to such surgical instruments with an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

The positioning of the end effector is constrained by the trocar. Generally, these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. Pat. No. 6,978,921 entitled, "SURGICAL STAPLING INSTRUMENT INCORPORATING AN E-BEAM FIRING MECHANISM" to Shelton et al., filed on 20 May 2003, which is hereby incorporated by reference in its entirety, describes an improved "E-beam" firing bar for severing tissue and actuating staples. Some of the additional advantages include affirmatively spacing the jaws of the end effector, or more specifically a staple applying assembly, even if slightly too much or too little tissue is clamped for optimal staple formation. Moreover, the E-beam firing bar engages the end effector and staple cartridge in a way that enables several beneficial lockouts to be incorporated.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally referred to as "articulation". This is typically accomplished by a pivot (or articulation) joint being placed in the extended shaft just proximal to the staple applying assembly. This allows the surgeon to articulate the staple applying assembly remotely to either side for better surgical placement of the staple lines and easier tissue manipulation and orientation. This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations.

For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation.

In commonly owned U.S. Pat. No. 7,111,769 entitled "SURGICAL INSTRUMENT INCORPORATING AN ARTICULATION MECHANISM HAVING ROTATION ABOUT THE LONGITUDINAL AXIS" to Frederick E. Shelton IV et al, the disclosure of which is hereby incorporated by reference in its entirety, a rotational motion is used to transfer articulation motion as an alternative to a longitudinal motion.

While these mechanically communicated articulation motions have successfully enabled an endoscopic surgical stapling and severing instrument to articulate, development trends pose numerous challenges and barriers to entry into the market. Conflicting design objects include a shaft of as small a diameter as possible to reduce the size of the surgical opening yet with sufficient strength to perform the several motions (e.g., closing, firing, articulation, rotation, etc.). In addition, transferring sufficient force without binding and other frictional problems imposes design constraints that limit desirable features and reliability.

Consequently, a significant need exists for an articulating surgical instrument that incorporates an articulation mechanism that employs an articulation force that may be incorporated within the close confines thereof without interfering with the firing and closing motions.

BRIEF SUMMARY OF THE INVENTION

The invention overcomes the above-noted and other deficiencies of the prior art by providing a surgical instrument having an articulating shaft attached between a handle and an end effector that uses fluid pressure to effect articulation.

In one aspect of the invention, a surgical instrument includes a proximal portion that is manipulated external to a patient to position an attached elongate shaft and end effector to a desired surgical site inside of the patient. An articulation joint attaches the end effector to the elongate shaft to give further clinical flexibility in reaching tissue at a desired angle. A fluid control, which is attached to the proximal portion, transfers fluid through the elongate shaft through a first fluid passage to a first fluid actuator that responds by articulating the articulation joint. Thereby, design flexibility is achieved by avoiding the design constraints of transferring a mechanical motion through the tight confines of the elongate shaft sufficient to effect articulation.

In another aspect of the invention, a surgical instrument includes a fluid control that differentially transfers fluid through two fluid passages in an elongate shaft that each communicate with opposing fluid actuators that cooperate to articulate the articulation joint. Thereby, actuators that perform efficiently and accurately in response to an increase in fluid pressure may be used to articulate the articulation joint in one direction with the other fluid actuator compressed thereby.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above and the detailed description of the embodiments given below, serve to explain the principles of the present invention.

FIG. 9 is top left perspective exploded view of a further alternative articulation joint for the surgical instrument of FIG. 1, including an alternate solid wall support plate mechanism incorporated into a lower double pivot link to support a firing bar and including a rail guided laterally moving member (T-bar).

FIG. 16 is a diagram of a laterally moving fluidic articulation mechanism with the rack and gear segment pivoting depicted in a nonarticulated state.

FIG. 17 is cross-section, front view in elevation of the fluidic articulation mechanism of FIG. 16 taken along lines 17-17.

FIG. 18 is a diagram of the laterally moving fluidic articulation mechanism with the rack and gear segment pivoting depicted in an articulated state.

FIG. 19 is cross-section, front view in elevation of the fluidic articulation mechanism of FIG. 18 taken along lines 19-19.

FIG. 24 is a top diagrammatic view of a surgical instrument having a slide bar laterally positioned by a pair of buckling members, each with a longitudinally adjustable proximal endpoint, to articulate an end effector.

FIG. 25 is a top diagrammatic view of the surgical instrument of FIG. 24 depicted in an articulated state.

FIG. 28 is a top diagrammatic view of a surgical instrument incorporating a pressurized fluid source and an articulation control mechanism.

FIG. 29 is a top diagrammatic view of the surgical instrument of FIG. 28 in an articulated state.

FIG. 44 is a top diagrammatic view of a surgical instrument incorporating left and right fluid bores that distally project fluidically translated distal pistons to differentially articulate an end effector about its pivotal attachment to an elongate shaft.

FIG. 45 is a top diagrammatic view of the surgical instrument of FIG. 44 in a leftward articulated state in response to rotation of an articulation control that differentially and proximally translates proximal pistons in respective fluid bores.

FIG. 52 is a top diagrammatic view of a surgical instrument of a tiller articulation mechanism positioned with a fluid transfer.

FIG. 53 is a top diagrammatic view of the surgical instrument of FIG. 52 articulated to the right.

DETAILED DESCRIPTION OF THE INVENTION

Overview of Articulating Shaft

Figure 1:
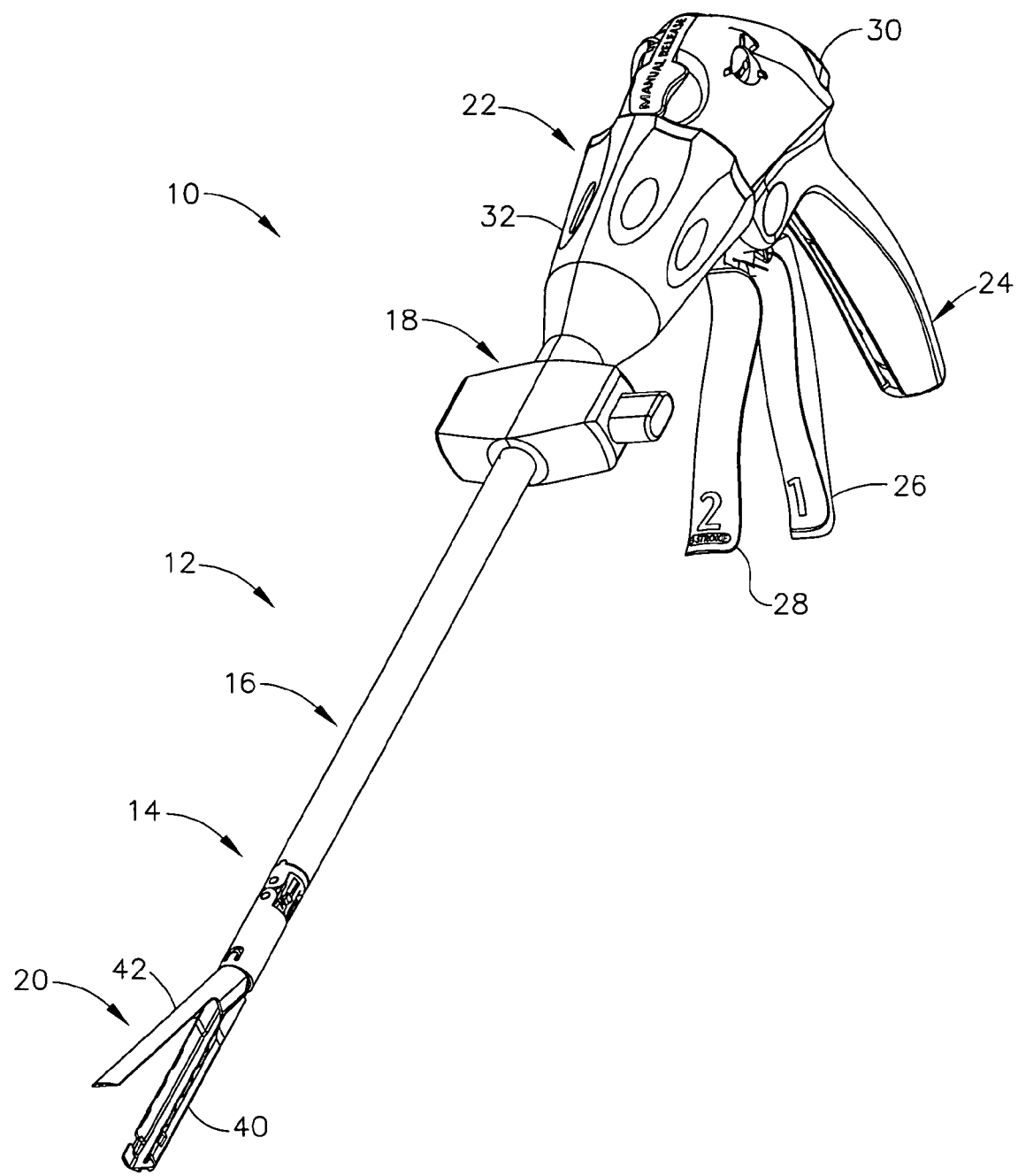
FIG. 1 is a front top perspective view of a surgical stapling and severing instrument shown with an open end effector, or staple applying assembly, and with the staple cartridge removed.
Figure 2:
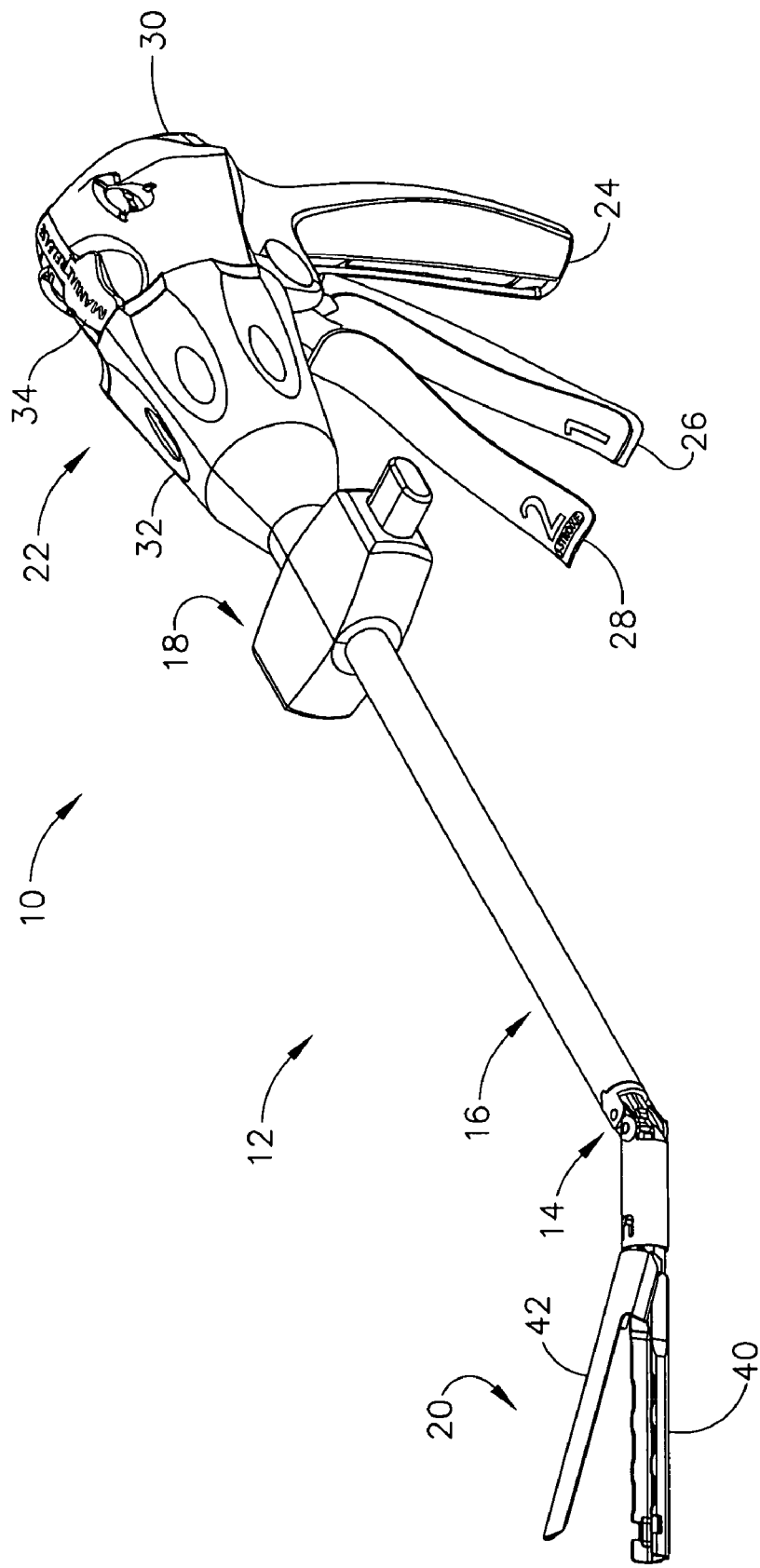
FIG. 2 is a front top perspective view of the surgical stapling and severing instrument of FIG. 1 with an articulation mechanism actuated by a fluidic actuation control.

Turning to the Drawings, wherein like numerals denote like components throughout the several views, FIG. 1 depicts a surgical instrument, which in the illustrative versions is more particularly a surgical stapling and severing instrument 10, that is capable of practicing the unique benefits of the present invention. In particular, the surgical stapling and severing instrument 10 is sized for insertion, in a nonarticulated state as depicted in FIG. 1, through a trocar cannula passageway to a surgical site in a patient (not shown) for performing a surgical procedure. Once an implement portion 12 is inserted through a cannula passageway, an articulation mechanism 14 incorporated into a distal portion of an elongate shaft 16 of the implement portion 12 may be remotely articulated, as depicted in FIG. 2, by an articulation control 18. An end effector, depicted in the illustrative version as a staple applying assembly 20, is distally attached to the articulation mechanism 14. Thus, remotely articulating the articulation mechanism 14 thereby articulates the staple applying assembly 20 from a longitudinal axis of the elongate shaft 16. Such an angled position may have advantages in approaching tissue from a desired angle for severing and stapling, approaching tissue otherwise obstructed by other organs and tissue, and/or allowing an endoscope to be positioned behind and aligned with the staple applying assembly 20 for confirming placement.

Handle

The surgical and stapling and severing instrument 10 includes a handle portion 22 proximally connected to the implement portion 12 for providing positioning, articulation, closure and firing motions thereto. The handle portion 22 includes a pistol grip 24 toward which a closure trigger 26 is pivotally and proximally drawn by the clinician to cause clamping, or closing, of the staple applying assembly 20. A firing trigger 28 is farther outboard of the closure trigger 26 and is pivotally drawn by the clinician to cause the stapling and severing of clamped tissue clamped in the staple applying assembly 20. Thereafter, a closure release button 30 is depressed to release the clamped closure trigger 26, and thus the severed and stapled ends of the clamped tissue. The handle portion 22 also includes a rotation knob 32 coupled for movement with the elongate shaft 16 to rotate the shaft 16 and the articulated staple applying assembly 20 about the longitudinal axis of the shaft 16. The handle portion 22 also includes a firing retraction handle 34 to assist in retracting a firing mechanism (not depicted in FIGS. 1-2) should binding occur, so that opening of the staple applying assembly 20 may occur thereafter.

It will be appreciated that the terms "proximal" and "distal" are used herein with reference to a clinician gripping a handle of an instrument. Thus, the surgical stapling assembly 20 is distal with respect to the more proximal handle portion 22. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

An illustrative multi-stroke handle portion 22 for the surgical stapling and severing instrument 10 of FIGS. 1-2 is described in greater detail in the co-pending and commonly-owned U.S. patent application currently abandoned and entitled "SURGICAL STAPLING INSTRUMENT INCORPORATING A MULTISTROKE FIRING POSITION INDICATOR AND RETRACTION MECHANISM" to Swayze and Shelton, Ser. No. 10/374,026, the disclosure of which is hereby incorporated by reference in its entirety, with additional features and variation as described herein. While a multi-stroke handle portion 22 advantageously supports applications with high firing forces over a long distance, applications consistent with the present invention may incorporate a single firing stroke, such as described in co-pending and commonly owned U.S. Pat. No. 7,000,818 entitled "SURGICAL STAPLING INSTRUMENT HAVING SEPARATE DISTINCT CLOSING AND FIRING SYSTEMS" to Frederick E. Shelton IV, Michael E. Setser, and Brian J. Hemmelgarn, the disclosure of which is hereby incorporated by reference in its entirety.

Implement Portion (Articulating Elongate Shaft and Staple Applying Assembly)

Figure 3:
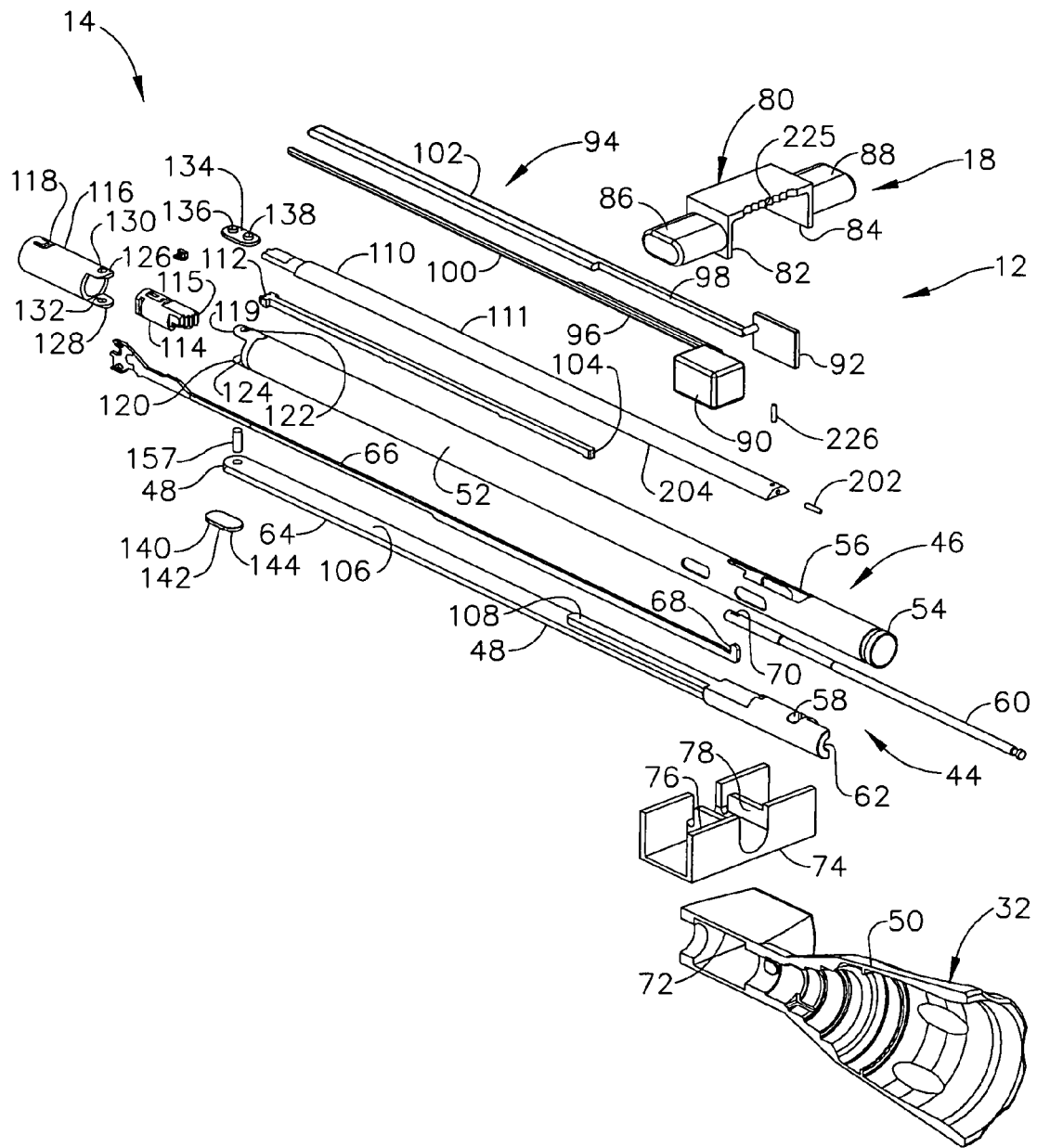
FIG. 3 is a perspective disassembled view of an elongate shaft and articulation mechanism of the surgical stapling and severing instrument of FIG. 1.
Figure 4:
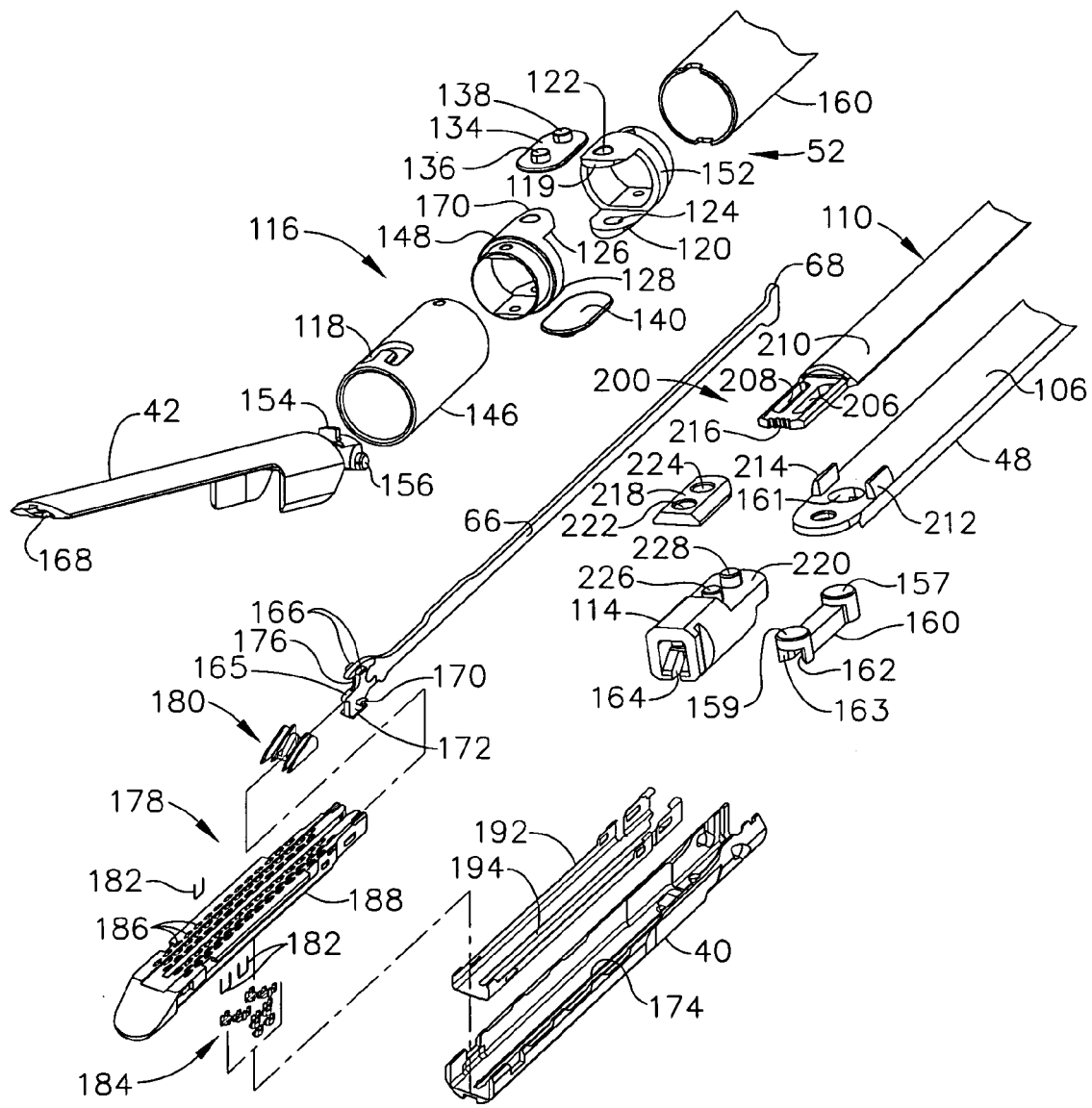
FIG. 4 is a perspective disassembled view of distal portions of an implement portion of the surgical stapling and severing instrument of FIG. 1, including the staple applying assembly and articulation mechanism.
Figure 5:
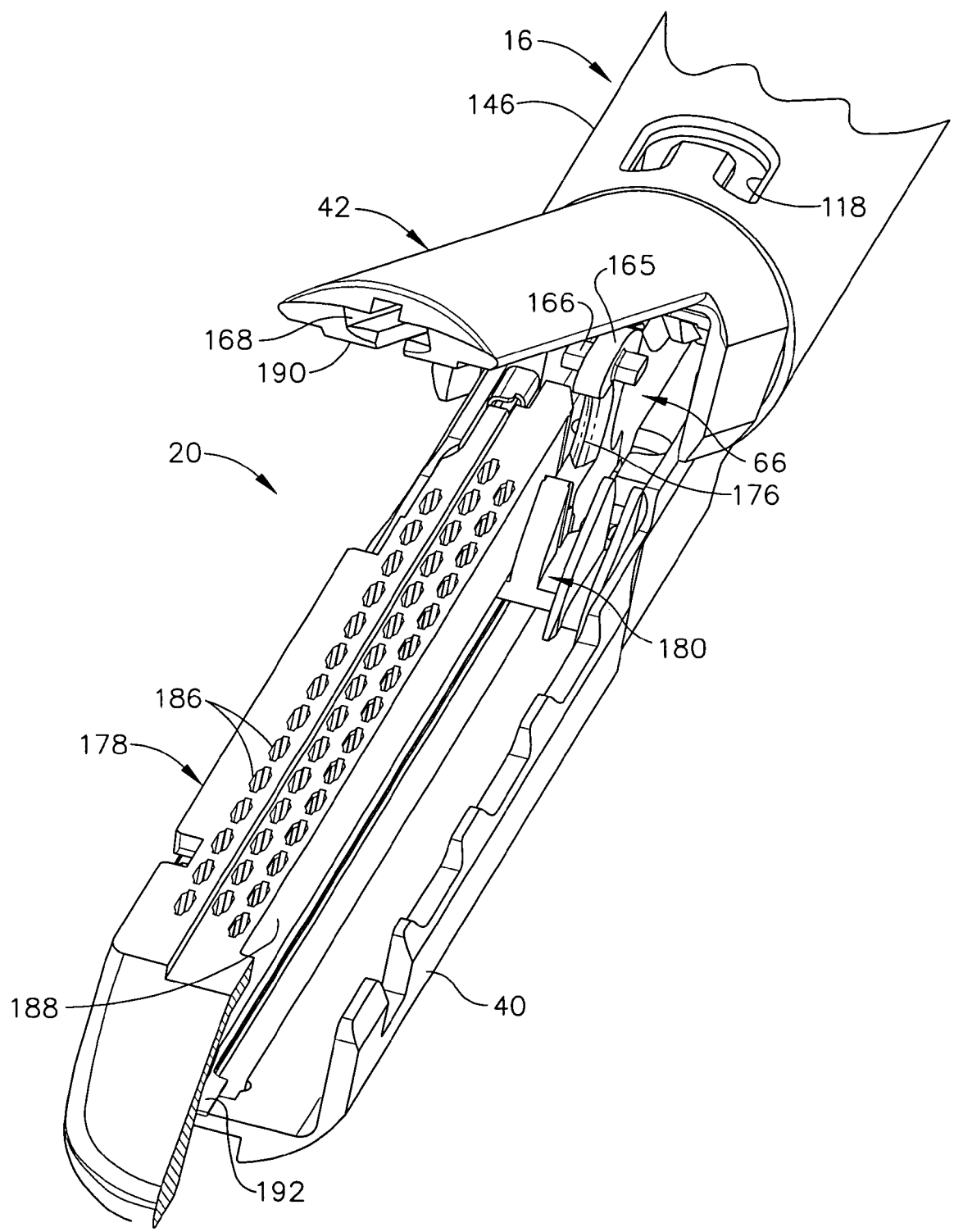
FIG. 5 is a top perspective view of the staple applying assembly of FIGS. 1 and 4 with a lateral half of a staple cartridge removed to expose components driven by a firing motion.

In FIGS. 3-5, the implement portion 12 advantageously incorporates the multiple actuation motions of longitudinal rotation, articulation, closure and firing within a small diameter suitable for endoscopic and laparoscopic procedures. The staple applying assembly 20 ("end effector") has a pair of pivotally opposed jaws, depicted as an elongate channel 40 with a pivotally attached anvil 42 (FIGS. 1-2, 4-5). Closure and clamping of the anvil 42 to the elongate channel 40 is achieved by longitudinally supporting the elongate channel 40 with a frame assembly 44 (FIG. 3) rotatingly attached to the handle portion 22 over which a double pivot closure sleeve assembly 46 longitudinally moves to impart a closing and opening respectively to a distal and proximal motion to the anvil 42, even with the staple applying assembly 20 articulated as in FIG. 2.

With particular reference to FIG. 3, the frame assembly 44 includes a single pivot frame ground 48 whose proximal end is engaged to the rotation knob 32, with a right half shell 50 thereon shown in FIG. 3. It should be appreciated a proximal end of the closure sleeve assembly 46, specifically of a closure straight tube 52, encompasses the proximal end of the frame ground 48, passing further internally to the handle portion 22 to engage closure components (not shown) that longitudinally translate the closure sleeve assembly 46. A circular lip 54 at the proximal end of the closure straight tube 52 provides a rotating engagement to such components. Engaging components of the rotation knob 32 pass through a longitudinal slot 56 on a proximal portion of the straight closure tube 52 to engage an aperture 58 proximally positioned on the frame ground 48. The longitudinal slot 56 is of sufficient length to allow the closure longitudinal translation of the closure sleeve assembly 46 at various rotational angles set by the rotation knob 32 to the closure sleeve assembly 46 and the frame ground 48.

The elongate shaft 16 supports the firing motion by receiving a firing rod 60 that rotatingly engages firing components of the handle portion 22 (not shown). The firing rod 60 enters a proximal opening 62 along the longitudinal centerline of the frame ground 48. The distal portion of the frame ground 48 includes a firing bar slot 64 along its bottom that communicates with the proximal opening 62. A firing bar 66 longitudinally translates in the firing bar slot 64 and includes an upwardly projecting proximal pin 68 that engages a distal end 70 of the firing rod 60.

The elongate shaft 16 supports articulation by incorporating a rectangular reservoir cavity 72, one lateral portion depicted in a distal portion of the rotation knob 32. A bottom compartment 74 that resides within the rectangular reservoir cavity 72 has laterally spaced apart left and right baffles 76, 78. An articulation actuator 80 slides laterally overtop of the bottom compartment 74, its downward laterally spaced left and right flanges 82, 84, which are outboard of the baffles 76, 78, each communicating laterally to left and right push buttons 86, 88 that extend outwardly from the respective shell halves of the rotation knob 32. The lateral movement of the articulation actuator 80 draws left and right flanges 82, 84 nearer and farther respectively to the left and right baffles 76, 78, operating against left and right reservoir bladders 90, 92 of a fluidic articulation system 94, each bladder 90, 92 communicating respectively and distally to left and right fluid conduits or passageways 96, 98 that in turn communicate respectively with left and right actuating bladders 100, 102. The latter oppose and laterally pivot a T-bar 104 of the articulation mechanism 14.

The frame assembly 44 constrains these fluidic actuations by including a top and distal recessed table 106 of the frame ground 48 upon which resides the fluid passages 96, 98 and actuating bladders 100, 102. The T-bar 104 also slidingly resides upon the recessed table 106 between the actuating bladders 100, 102. Proximal to the T-Bar 104, a raised barrier rib 108 is aligned thereto, serving to prevent inward expansion of the fluid passages 96, 98. The frame assembly 44 has a rounded top frame cover (spacer) 110 that slides overtop of the frame ground 48, preventing vertical expansion of the fluid passages 96, 98 and actuating bladders 100, 102, as well as constraining any vertical movement of the T-bar 104. In particular, the frame cover 110 includes features that enable it to also provide an articulation locking member 111, described in greater detail below as part of an articulation locking mechanism 113.

A distal end ("rack") 112 of the T-bar 104 engages to pivot a proximally directed gear segment 115 of an articulated distal frame member 114 of the articulation mechanism 14. An articulating closure ring 116 encompasses the articulated frame member 14 and includes a horseshoe aperture 118 that engages the anvil 42. A double pivoting attachment is formed between the closure straight tube 52 and articulating closure ring 116 over the articulating mechanism 14, allowing longitudinal closure motion even when the articulating mechanism 14 is articulated. In particular, top and bottom distally projecting pivot tabs 118, 120 on the closure straight tube 52 having pin holes 122, 124 respectively are longitudinally spaced away from corresponding top and bottom proximally projecting pivot tabs 126, 128 on the articulating closure ring 116 having pin holes 130, 132 respectively. An upper double pivot link 134 has longitudinally spaced upwardly directed distal and aft pins 136, 138 that engage pin holes 122, 130 respectively and a lower double pivot link 140 has longitudinally spaced downwardly projecting distal and aft pins 142, 144 that engage pin holes 124, 132 respectively.

With particular reference to FIG. 4, the articulating closure ring 116 is shown for enhanced manufacturability to include a short tube 146 attached to an articulating attachment collar 148 that includes the proximally projecting pivot tabs 126, 128. Similarly, the straight closure tube 52 is assembled from a long closure tube 150 that attaches to an aft attachment collar 152 that includes the distally projecting pivot tabs 118, 120. The horseshoe aperture 118 in the short closure tube 146 engages an upwardly projecting anvil feature 154 slightly proximal to lateral pivot pins 156 that engage pivot recesses 158 inside of the elongate channel 40.

The illustrative version of FIG. 4 includes a dog bone link 160 whose proximal pin 157 pivotally attaches to the frame ground 48 in a frame hole 161 and whose proximal pin 159 rigidly attaches to a proximal undersurface 162 of the articulating frame member 114, thereby providing pivotal support therebetween. A bottom longitudinal knife slot 163 in the dog bone link 160 guides an articulating portion of the firing bar 66. The articulating frame member 114 also includes a bottom longitudinal slot 164 for guiding a distal portion of the firing bar 66.

Staple Applying Apparatus (End Effector)

With reference to FIGS. 4-5, the firing bar 66 distally terminates in an E-beam 165 that includes upper guide pins 166 that enter an anvil slot 168 in the anvil 42 to verify and assist in maintaining the anvil 42 in a closed state during staple formation and severing. Spacing between the elongate channel 40 and anvil 42 is further maintained by the E-beam 164 by having middle pins 170 slide along the top surface of the elongate channel 40 while a bottom foot 172 opposingly slides along the undersurface of the elongate channel 40, guided by a longitudinal opening 174 in the elongate channel 40. A distally presented cutting surface 176 of the E-beam 164, which is between the upper guide pins 166 and middle pin 170, severs clamped tissue while the E-beam actuates a replaceable staple cartridge 178 by distally moving a wedge sled 180 that causes staple drivers 182 to cam upwardly driving staples 184 out of upwardly open staple holes 186 in a staple cartridge body 188, forming against a staple forming undersurface 190 of the anvil 42. A staple cartridge tray 192 encompasses from the bottom the other components of the staple cartridge 178 to hold them in place. The staple cartridge tray 192 includes a rearwardly open slot 194 that overlies the longitudinal opening 174 in the elongate channel 40, thus the middle pins 170 pass inside of the staple cartridge tray 192.

The staple applying assembly 20 is described in greater detail in co-pending and commonly-owned U.S. patent application Ser. No. 10/955,042 and U.S. Publication No. U.S. 2005-0263562 entitled "ARTICULATING SURGICAL STAPLING INSTRUMENT INCORPORATING A TWO-PIECE E-BEAM FIRING MECHANISM" to Frederick E. Shelton IV, et al., filed 30 Sep. 2004, the disclosure of which is hereby incorporated by reference in its entirety.

Articulation Locking Mechanism

In FIGS. 3,4 and 6-8, an articulation lock mechanism 200 is advantageously incorporated to maintain the staple applying assembly 20 at a desired articulation angle. The articulation lock mechanism 200 reduces loads on the left and right actuating bladders 100, 102. In particular, a compression spring 202 (FIG. 3) is proximally positioned between a proximal end 204 of the articulation locking member 111 and the handle portion 22, biasing the articulation locking member 111 distally. With particular reference to FIG. 4, two parallel slots 206, 208 at a distal end 210 of the articulation locking member 111 receive respectively upwardly projecting guide ribs 212, 214 on the frame ground 48. The guide ribs 212, 214 are longitudinally shorter than the parallel slots 206, 208 allowing a range of relative longitudinal travel. Thereby, with particular reference to FIG. 8, selective abutting engagement of a distal frictional surface, depicted as a toothed recess 216 distally projecting from the articulation locking member 111, is engaged to a corresponding locking gear segment 217 in a brake plate 218 received into a top proximal recess 220 of the articulating frame member 114. Distal and proximal holes 221, 222 in the brake plate 218 receive distal and proximal pins 223, 224 that upwardly project from the top proximal recess 220.

Figure 6:
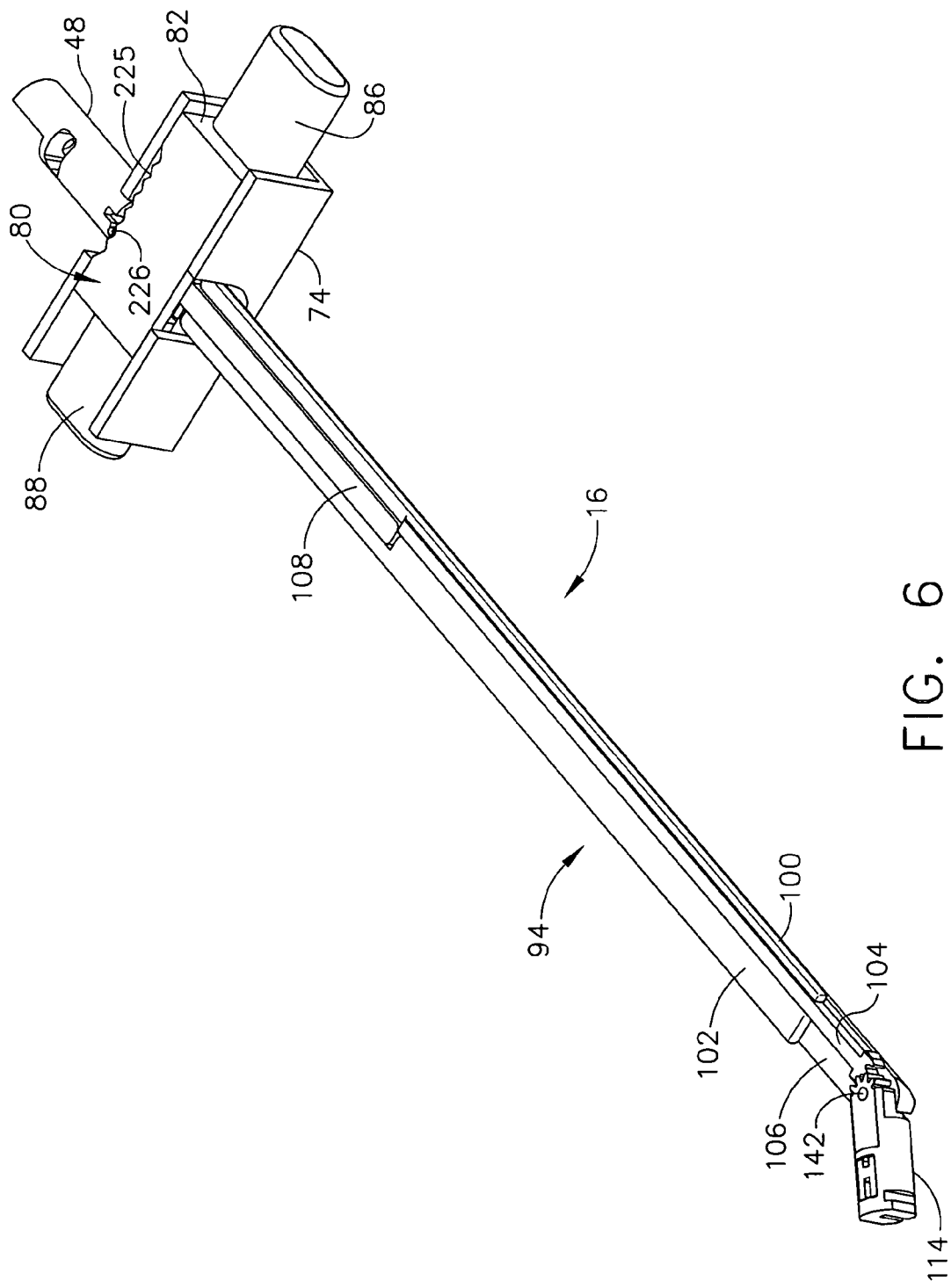
FIG. 6 is a front perspective view of an implement portion of the surgical instrument of FIG. 1 with a double pivot closure sleeve assembly and end effector removed to expose a single pivot frame ground articulated by a fluidic articulation mechanism.

With particular reference to FIG. 6, the elongate shaft 16 is depicted in an articulated position with the closure sleeve assembly 46 removed from around the frame assembly 44 and without the elongate channel 40 and anvil 42. Articulation actuator 80 is shown moved laterally to the left to compress right proximal reservoir bladder 90 and expand distal right actuation bladder 100 moving T-bar 104 to the position shown. Thus, lateral movement of the articulation actuator 80 articulates the distal frame 114 clockwise about the single pivot frame ground 48 as shown. The articulation actuator 80 advantageously also automatically engages and disengages the articulation lock mechanism 200. In particular, a toothed detent surface 225 along a proximal top surface of the articulation actuator 80 receives an upwardly projecting locking pin 226 from the proximal end 204 of the articulation locking member 111. The engagement of the locking pin 226 within the root of the toothed detent surface 225 provides sufficient distal movement of the articulation locking member 111 for locking engagement of the locking gear segment 217 in the brake plate 218. Lateral movement by an operator of the compression member 272 proximally urges the locking pin 226 proximally, and thus disengages the articulation locking member 111 from the brake plate 218. When the operator releases the articulation actuator 80, the locking pin 226 is urged by the compression spring 202 into the adjacent detent in detent surface 225 to lock the locking mechanism 111, and thereby the staple applying assembly 20, and to constrain the articulation mechanism 14 at a desired articulation position by constraining and expanding the inflated shape of the proximal left and right reservoir bladders 90, 92.

Portions of the articulation lock mechanism 200 are described in greater detail in commonly-owned U.S. Pat. No. 5,673,841 A "SURGICAL INSTRUMENT" to Dale R. Schulze and Kenneth S. Wales, et al., filed 10 Mar. 1996, the disclosure of which is hereby incorporated by reference in its entirety.

Alternatively or additionally, an orifice may be provided within parallel fluid bladders 236, 238 to control the flow rate between the proximal actuating bladders 100,102 and distal reservoir bladders 90, 92. In FIGS. 16, 18, the fluid passageways 258, 264 may be sized to provide resistance to changing the angle of articulation, serving as the orifices or to include a fluid flow rate limiting structure.

Figure 10:
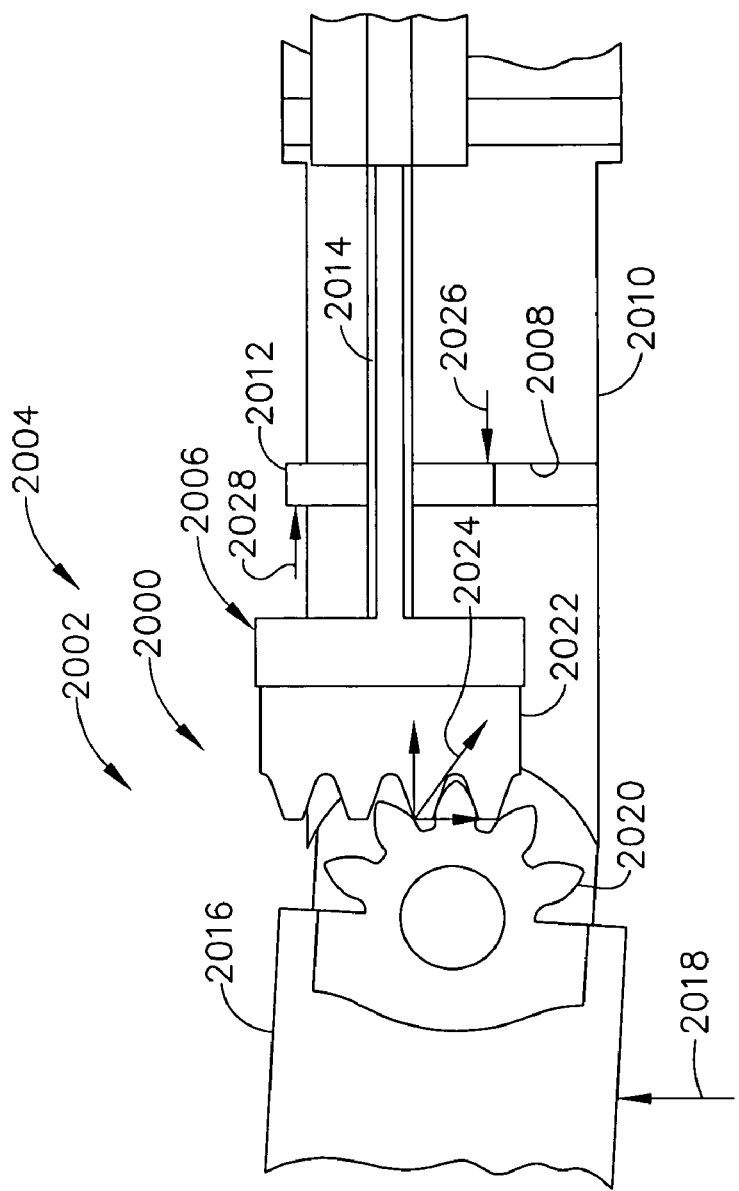
FIG. 10 is a top diagrammatic view of an alternate articulation locking mechanism for the surgical instrument of FIG. 1 with a closure sleeve assembly removed to expose a backloading disengaged T-bar for automatic articulation lock engagement and disengagement.

In FIG. 10, an alternate locking mechanism 2000 of an articulation mechanism 2002 of a surgical instrument 2004, is normally unlocked and is activated by cocking a laterally moving T-bar 2006 due to back loading. A slot 2008 is located in a frame ground 2010 to receive and guide a rib 2012 extending down from the T-bar 2006. A slender longitudinal section 2014, which is orthogonally attached to the rib 2012 deflects if an end effector 2016 is backloaded. For instance, as the end effector 2016 is forced to the right as depicted at arrow 2018, for instance, its proximal gear segment 2020 acts upon a rack 2022 of the T-bar 2006, imparting a nonorthogonal backdriving force, as depicted at arrow 2024. Thus, the slender longitudinal section 2014 bends, cocking rib 2012 in slot 2008. This cocking produces opposing binding forces, as depicted by arrows 2026, 2028, that lock the T-bar 2006 and prevent further articulation. Unlocking occurs when actuation of the articulation bladders uncocks the laterally moving T-bar 2006. Thereafter, the rib 2016 may assist in guiding the T-bar 2006.

Figure 11:
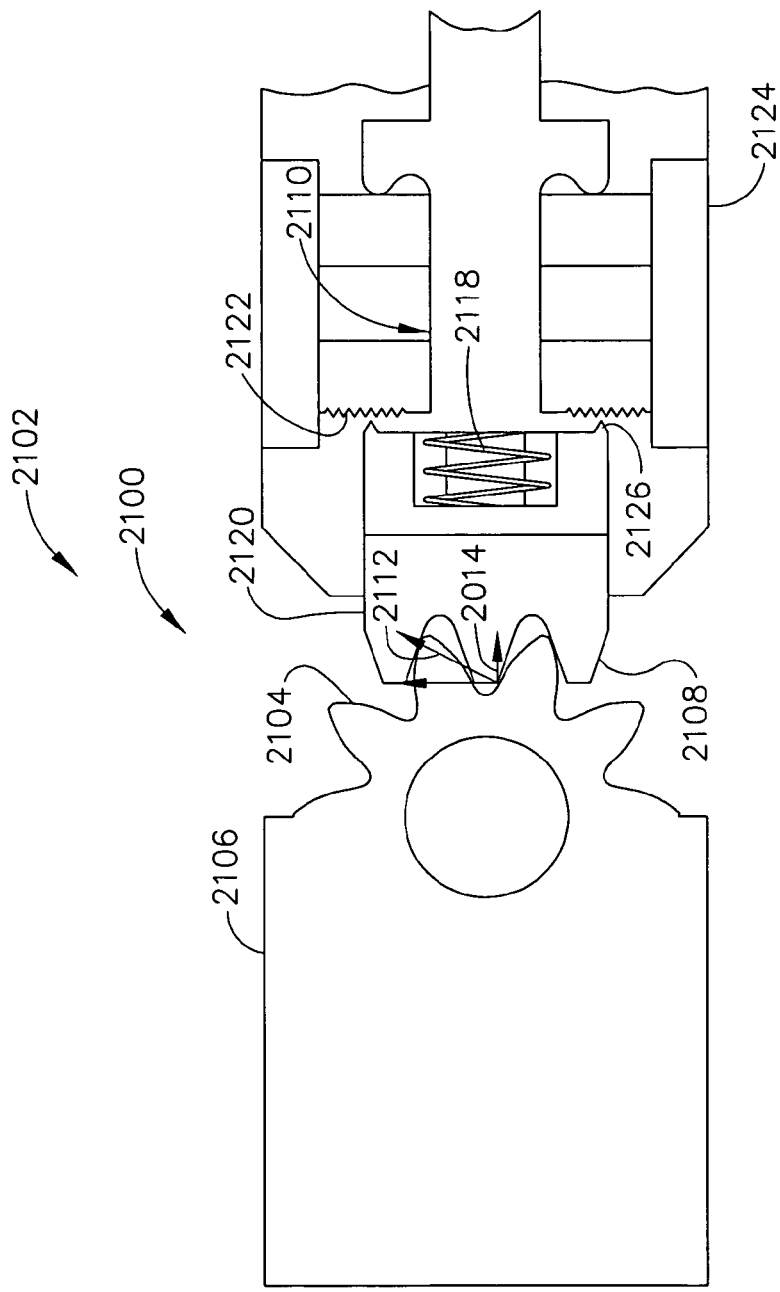
FIG. 11 is a top diagrammatic view of an additional alternative articulation mechanism for the surgical instrument of FIG. 1, a spring biases rack on a T-bar with locking features that engage due to backloading from an end effector.

In FIG. 11, yet an additional articulation locking mechanism 2100 for a surgical instrument 2102 is depicted that is normally unlocked and activated by the proximal force vector from the 20 degree pressure angle from gear teeth 2104 of an end effector 2106 and rack teeth 2108 of a T-bar 2110. When the end effector 2106 is backloaded, as depicted by nonorthogonal arrow 2112, the longitudinal vector of the pressure angle, depicted as arrow 2114, moves the T-bar 2110 proximally. This longitudinal force vector is applied to a stiff spring 2118 behind a rack 2120 of the T-bar 2110. When the spring 2118 deflects as T-bar 2110 moves proximally, locking teeth 2126 projecting proximally from the rack 2120 are brought into engagement with locking elements 2122, distally projecting and laterally aligned on a ground frame 2124.k 2120. The locking teeth 2126 and locking elements 2122 disengage when the proximal force vector is reduced or eliminated by removing the back loading of the end effector 2106 and allowing T-bar 2110 to move distally under urging from spring 2118.

Double Pivot Closure Sleeve and Single Pivot Frame Ground Combination

Figure 7:
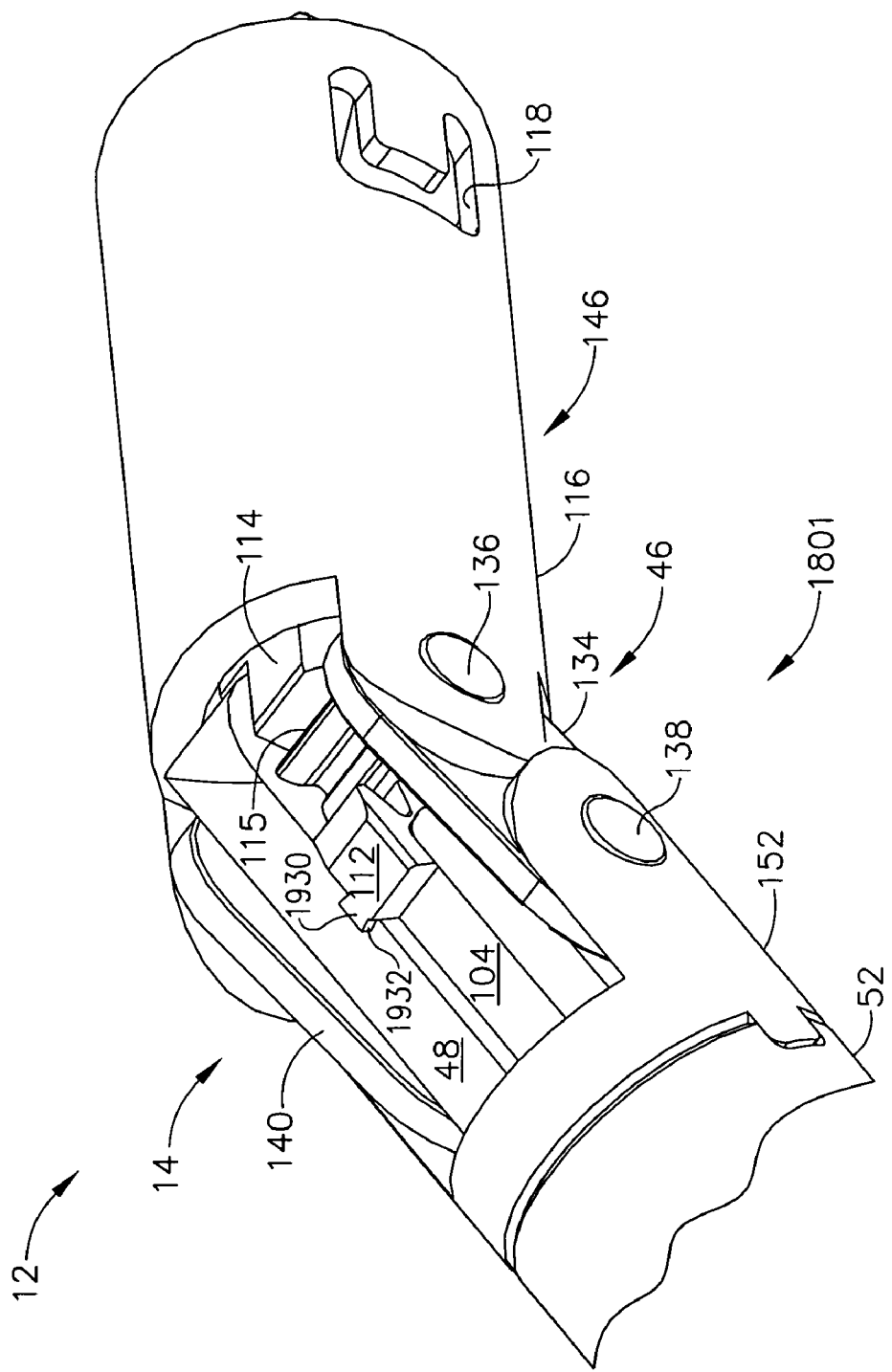
FIG. 7 is perspective detail view of an alternative articulation joint for the surgical instrument of FIG. 1 depicting a double pivoting closure sleeve assembly at a proximal position with a single pivot frame ground.

With reference to FIGS. 3-4 and 7, the implement portion 12 advantageously incorporates the double pivot closure sleeve assembly 46 that longitudinally translates over and encompasses a single pivot frame ground 48. These mechanisms and their operation will now be described in further detail. With particular reference to FIG. 7, the articulation mechanism 14 is depicted in an articulated state with the closure sleeve assembly 46 retracted proximally to an anvil open state. With the anvil 42 open, actuation of the articulation control 18 causes the articulated closure ring 116 to pivot about the upwardly directed distal pin 136 and downwardly directed distal pin 142 respectively of the upper and lower double pivot closure links 134, 140. The frame ground 48 pivots around a single pin, depicted as the proximal pin 157 that joins frame ground 48 to distal frame member 114. With the anvil 42 open, the proximal pin 147 of frame ground 48 is aligned with the distal most position of upper and lower double pivot links 134, 140 of the closure sleeve assembly 46. This positioning allows easy pivoting and rotation of the staple applying assembly 20 while the anvil 42 is open. When the closure sleeve assembly 46 is moved distally to pivot anvil 42 closed, the closure straight tube 52 moves distally about frame ground 48 and the articulated closure ring 116 moves distally along the articulated distal frame member 114 axis as urged by pivot links 134, 140. Dual pivoting pins 136, 138 and 142, 144 on links 134, 140 facilitate engagement with closure straight tube 52 and articulated closure ring 116 as they are urged towards the distal closure position when the device is articulated (not shown). At the distal closure position, the frame ground pivot pin ("proximal pin") 147 is vertically aligned with proximal pivot pins 138, 144 at full articulation or may fall at any point between distal pins 136, 142 and proximal pins 138, 144 while working effectively.

Solid Firing Bar Support

Figure 8:
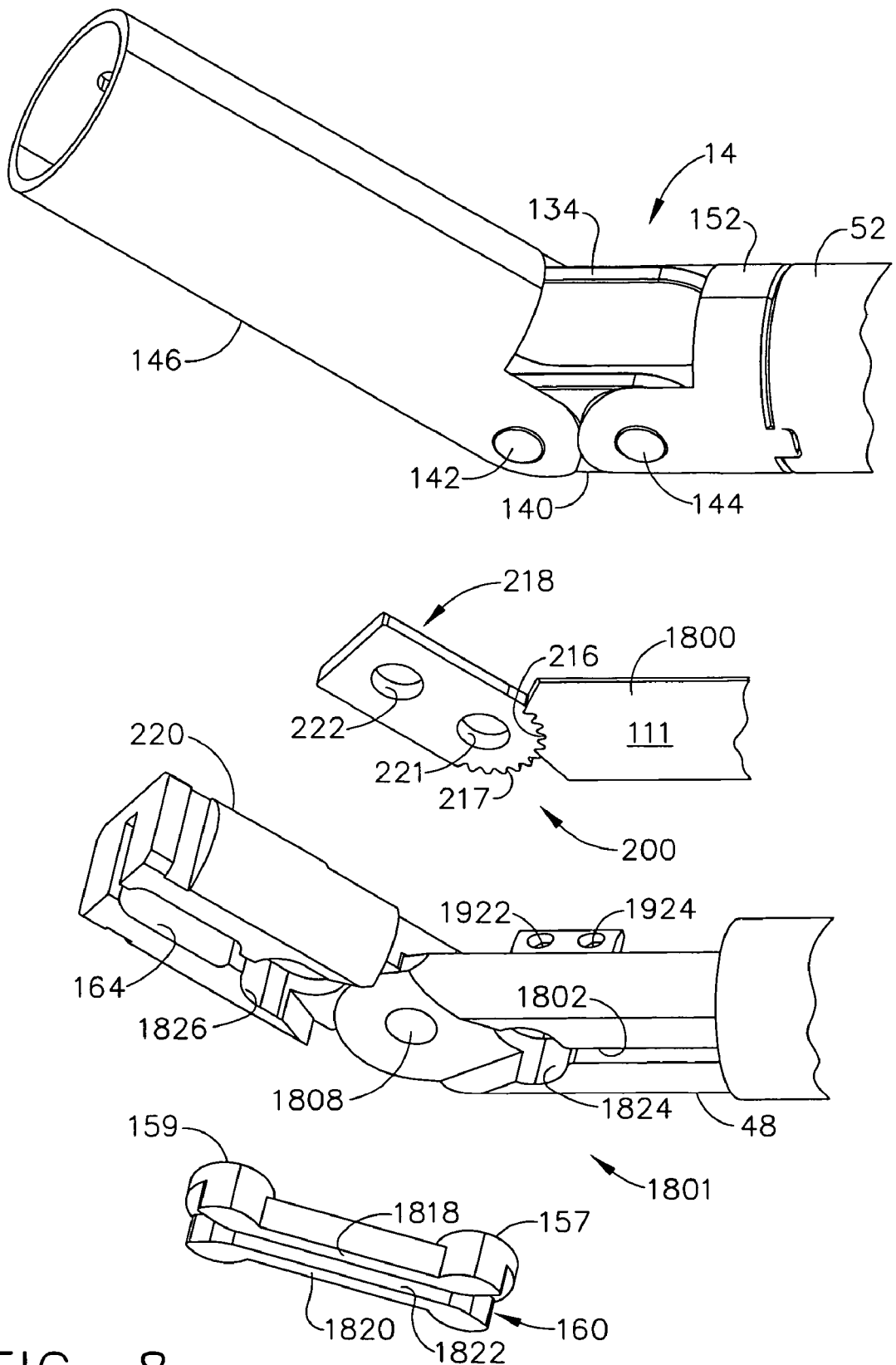
FIG. 8 is a bottom right perspective exploded view of the alternative articulation joint of FIG. 7 including a double pivoting fixed-wall dog bone link and a frame ground incorporating rail guides for a lateral moving member (T-bar).

In FIG. 8, the articulation mechanism 14 of FIG. 7 is partially exploded and viewed from the bottom, showing a solid wall firing bar support design (dog bone link 160) that offers advantages over conventional flexible support plates. Support plates are used to bridge the gap and guide and support the firing bar 66 through a single frame ground pivot articulation joint 1801. Flexible firing bars are known, but the incorporation of solid wall firing bars such as those shown in FIGS. 4, 8 and 9 offer unique advantages. Referring now to FIG. 8, frame ground 48 includes a frame knife slot 1802 that runs along the bottom of frame ground 48 and a distal knife slot 164 runs along the bottom of an articulating distal frame member 114 for the sliding reception of the firing bar 66 (not shown) therein. Frame ground 48 described above includes a direct single pivotal connection 157 with the distal frame member 114. The fixed wall dog bone link 160 that is rotatably connected on proximal pin end 157 and movably connected on distal pin end 159 includes left and right lateral guides 1818, 1820, defining therebetween a guidance slot 1822 for sliding passage of a firing bar 66 (FIG. 4).

Thus, to bridge the gap between frame ground 48 and the distal frame member 114, the fixed wall pivoting dog bone link 160 is pivotally attached to frame ground 48 and slidingly attached to frame member 114. Proximal pin 157 of the pivoting dog bone 160 is pivotally received in a bore 1824 in frame ground 48 enabling pivotal dog bone 160 to pivot about pocket 1824. A distal pin 159 extends upwards from pivotal dog bone 160 and is slidingly received in a slot 1826 in distal frame 114. Articulation of staple applying assembly 20 to an angle of such as 45 degrees from the longitudinal axis pivots pivoting dog bone 160 in bore 1824 at its proximal pin 157, and distal pin 157 slides in slot 1826 at its distal end 1814 to bend firing bar 66 to two spaced apart angles that are half of the angle of the staple applying assembly 20. Unlike previously referenced flexible support plates that bend the firing bar 66 to a 45 degree angle, the fixed wall pivoting dog bone 160 bends the firing bar 66 to two spaced apart angles of such as 22.5 degrees each. Bending the flexible firing bar or bars 66 to half the angle cuts the bend stress in the firing bars 66 to one half of that found in conventional articulation supports. Reducing the bending stress in the firing bars 66 reduces the possibility of permanently bending or placing a set in the firing bars, reduces the possibilities of firing jams, ensures lower firing bar retraction forces, and provides smoother operation of the firing system.

In FIG. 9, a surgical instrument 1900 includes double closure pivot. Single frame pivot articulation joint 1902 shows an alternate solid wall support plate mechanism 1904 that replaces the lower double pivot link 140 and dog bone link 1812. Left and right firing bar supports 1906, 1908 extend upwardly from a lower double pivot link 1910 of a closure sleeve assembly 1912. Clearance 1914 is provided in a frame ground 1916 for the firing bar supports 1906, 1908 to travel as the closure sleeve assembly 1912 moves distally to close the anvil 42 (not shown in FIG. 9) and proximally to open anvil 42. Like the above described pivoting dog bone 1812, the alternate lower double pivoting link 1910 also bends and supports the firing bar 66 (not shown in FIG. 9) to have two spaced apart bend angles that are up to one half of the bend angle of the staple applying assembly 20.

Lateral Member Guide Mechanisms

Figure 12:
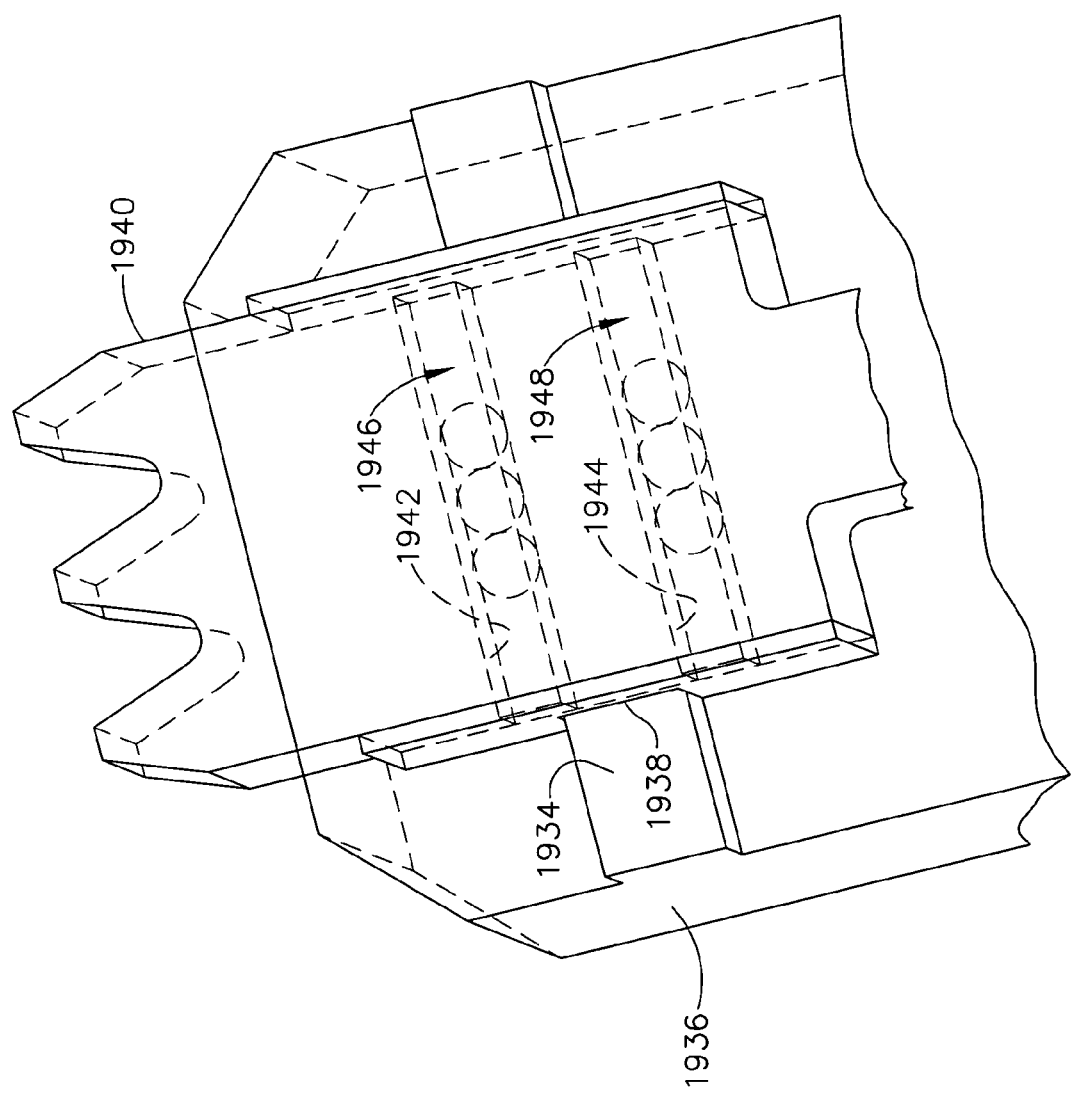
FIG. 12 is an alternative T-bar and frame ground incorporating lateral guidance for the surgical instrument of FIG. 1.
Figure 13:
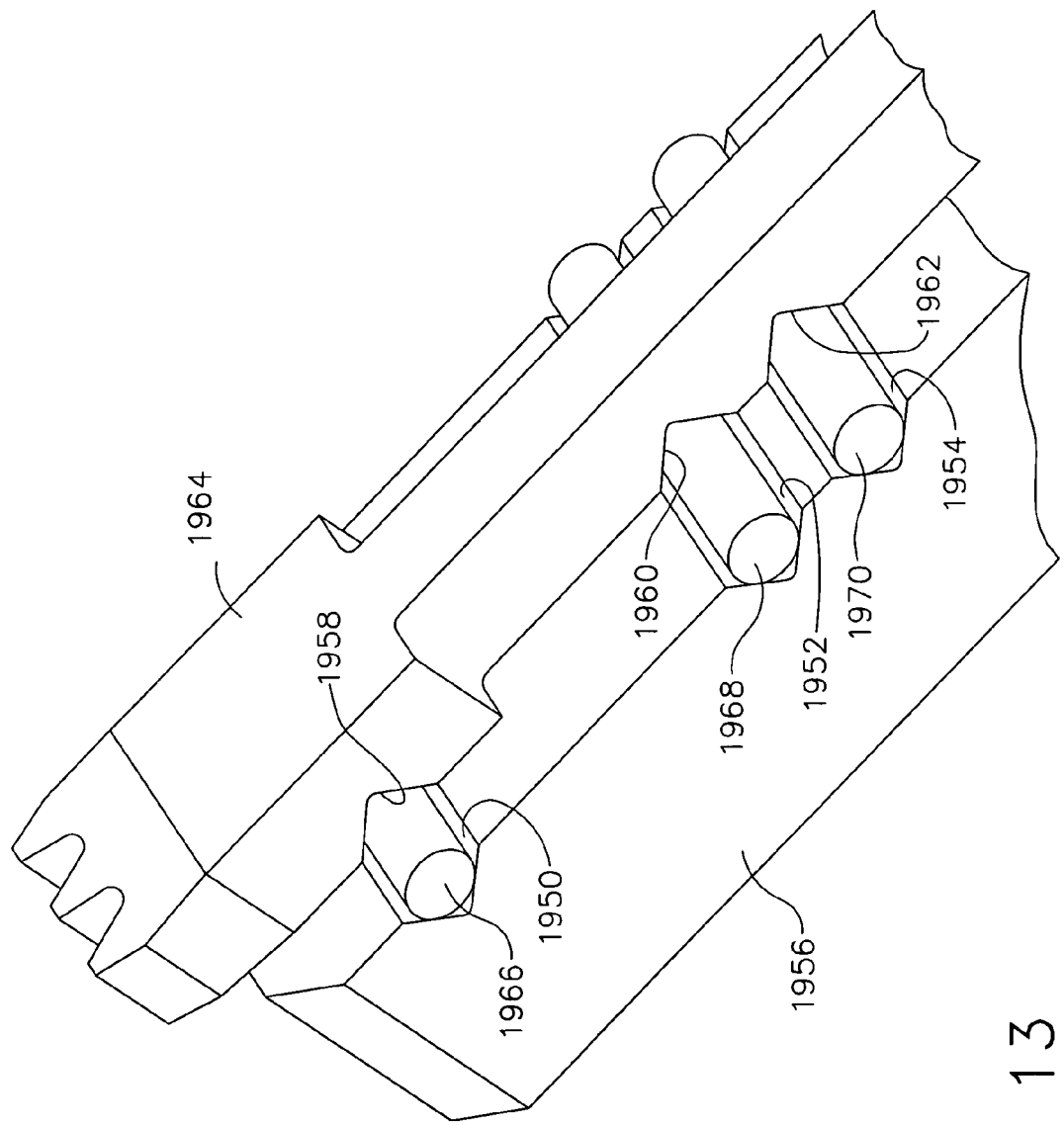
FIG. 13 is yet an additional alternative T-bar and frame ground incorporating lateral guidance for the surgical instrument of FIG. 1.

With further reference to FIG. 9, left and right upward flanges 1918, 1920 on the frame ground 1916 include distal and proximal lateral pin guides 1922, 1924 that pass laterally through holes in a T-bar 1926, assisting in minimizing binding in an articulation mechanism 1928. As another example, in FIG. 7, the T-bar 104 advantageously includes a dovetail lateral guide 1930 that laterally slides within a dovetail channel 1932 formed therein. As yet a further example, in FIG. 12, a raised rib 1934 on a frame ground 1936 is received within a rectangular slot 1938 formed in a T-bar 1940. To further facilitate non-binding lateral translation, distal and proximal lateral bearing tracks each include a respective plurality of ball bearings 1946, 1948. As yet a further example, in FIG. 13, a plurality of frame lateral grooves 1950-1954 are formed in a frame ground 1956 with corresponding T-bar lateral grooves 1958-1962 in a T-bar 1964. Slide rollers 1966-1970 reside trapped within respective pairs of lateral grooves 1950/ 1958, 1952/1960, 1954/1962. These are by no means an exhaustive list of lateral guidance members that prevent unwanted cocking or rotation of the T-bar 1940.

Double Pivot Frame Ground and Single Pivot Closure Combination

Figure 14:
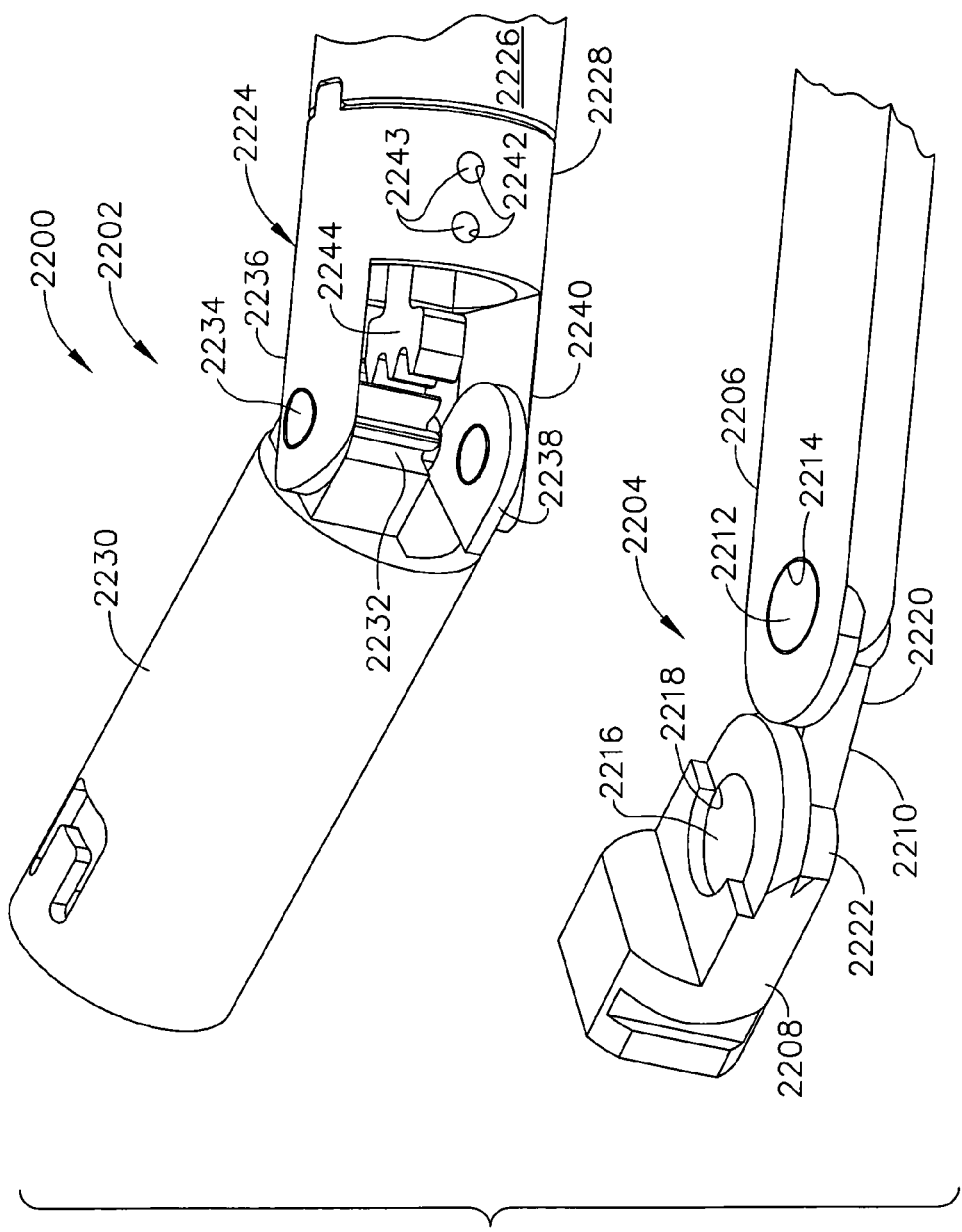
FIG. 14 is a left top perspective disassembled view of an alternative articulation mechanism including a double pivoting frame assembly and single pivoting closure sleeve assembly for the surgical instrument of FIG. 1.
Figure 15:
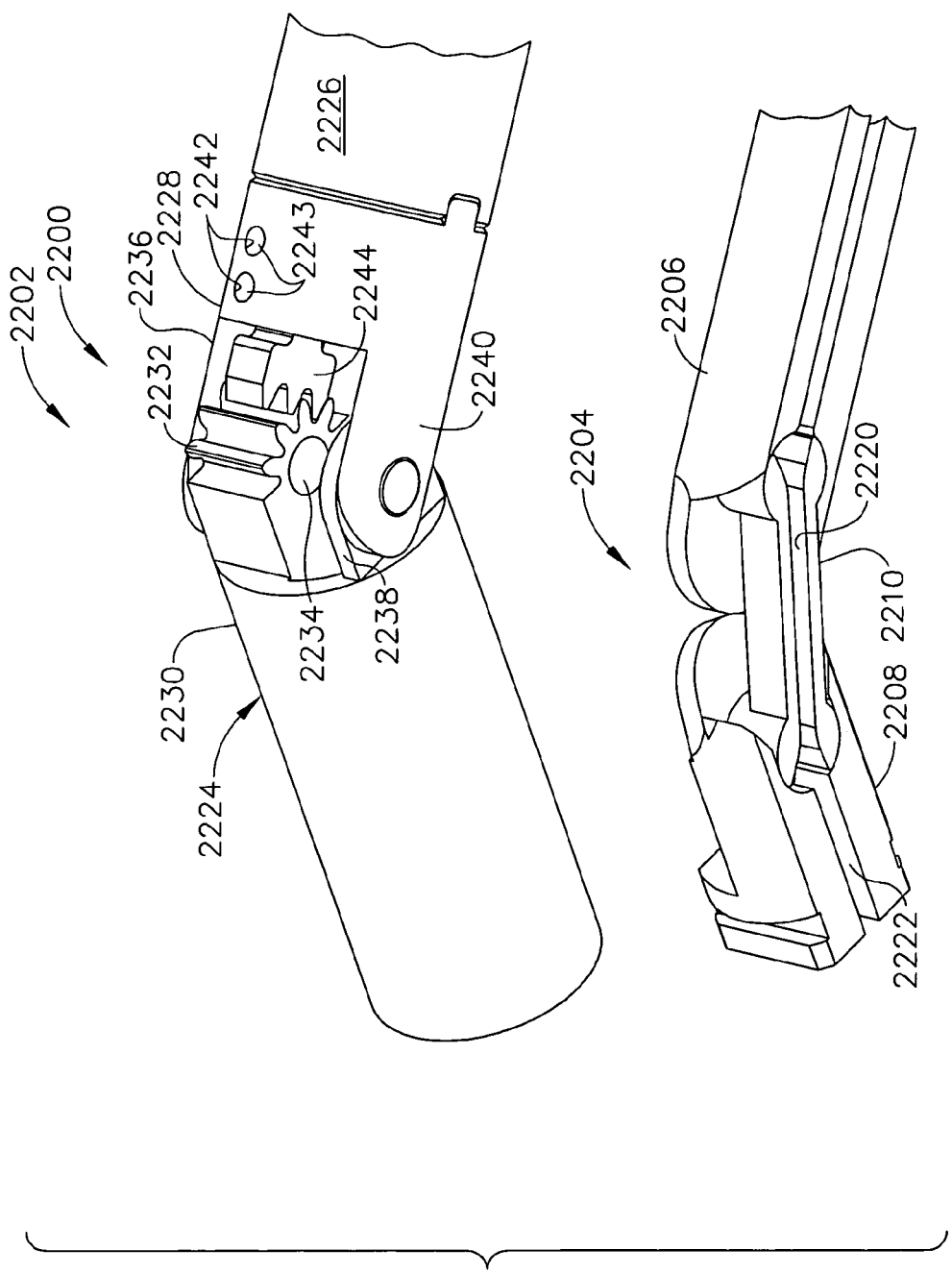
FIG. 15 is a left bottom perspective view of the alternative articulation mechanism of FIG. 14.

In FIGS. 14-15, an alternate frame ground and closure mechanism 2200 includes a surgical instrument 2202 that includes double pivoting frame assembly 2204. In particular, a frame ground 2206 is connected to distal frame member 2208 by a dual pivot frame dog bone 2210 having a proximal pivot pin 2212 pivotally engaging a proximal bore 2214 in frame ground 2206 and a distal pivot pin 2216 engaging a distal bore 2218 of distal frame member 2208. A guidance slot 2220 is located on the underside of dog bone 2210 for the guidance of a firing bar 66 (not shown in FIGS. 14-15) therein. Knife slot 2222 is located in distal frame member 2208. As shown, articulation of the closure ring 2230 to a 45 degree angle articulates distal frame member 2208 to a 45 degree angle and articulates frame dog bone 2210 to half that angle. Consequently, firing bar 66 is subjected to the two shallow half bends that are spaced apart and obtains all the benefits listed above.

Outermost closure sleeve assembly 2224 is different in that only one pivot axis of the double pivoting design of the frame assembly 2204 accommodates its longitudinal closure motion. As shown, a closure tube shaft 2226 has a clevis 2228 at a distal end. Clevis 2228 is pivotally engaged with a closure ring 2230. Closure ring 2230 has a proximal gear 2232 formed at a distal end and pin 2234 pivotally engages an upper tang 2236 of clevis 2228 and a lower arm 2238 engages with a lower tang 2240 of clevis 2228. Holes 2242 in the clevis 2228 receive lateral guides pins 2243 and slidably attach a T-bar 2244 therein to engage proximal gear 2232 of the closure ring 2230. Thus, this alternate mechanism 2200 uses a reversed single/dual pivot alternate concept from the previously described mechanism. That is, the alternate closure mechanism has a single pivot and the alternate frame ground has a dual pivot, unlike the previously described dual pivot closure mechanism with a single pivot frame ground.

Laterally Moving Articulation Mechanism

In FIGS. 16-19, a laterally moving articulation mechanism 230 is depicted schematically to show lateral motion being used to effect articulation of an end effector 232. Lateral motion is the movement of at least one element toward or away from the longitudinal axis of a surgical device 234. This motion is generally at right angles to the longitudinal axis, which is a horizontal line bisecting the mechanism 230, and does not involve rotational motion or longitudinal motion. Laterally moving articulation mechanisms can be fluidly actuated as shown in FIGS. 16-19 or mechanically actuated as shown in FIGS. 20-23.

Laterally Moving Fluid Articulation Mechanism

The laterally moving articulation mechanism 230 is shown schematically in FIGS. 16-19 and includes a fluid control system 235 having fluid filled parallel left and right fluid bladders 236, 238 extending longitudinally therein that move a lateral member or T-bar 240 laterally by the movement of fluids 242. All directions are in reference to the longitudinal axis. Referring to the unarticulated view of FIGS. 16 and 17, the distally located end effector 232 pivots about pin 244 and has a gear segment 246 at a proximal end. Pivot pin 244 is attached to a frame (not shown). A rack 248 at a distal end of the T-bar 240 operably engages gear segment 246. T-bar 240 and rack 248 are laterally movable along axis A-A. A distal portion of the long left and right fluid bladders 236, 238 lies laterally to the laterally movable T-bar 240 and is laterally constrained within a closure sleeve 250 and vertically constrained by a frame 252 below and a spacer 254 above. Left actuating fluid bladder 236 is filled with fluid 242 and has left distal actuating bladder 256, left fluid passageway 258, and a left proximal reservoir bladder 260. Right fluid bladder 238 contains fluid 242 and has a right distal actuating bladder 262, right fluid passageway 264, and right proximal reservoir bladder 268. A fixed divider 270 extends from the frame 252 and separates the bladders 260, 268 and the fluid passageways 258, 264. The fixed divider 270 and the closure sleeve 250 constrain the fluid passageways 258, 264 and prevent expansion in the fluid passage sections 258, 264 of the bladders 236, 238. A laterally movable "C"-shaped compression member 272 is included in articulation control mechanism 230 for the compression of one of the proximal reservoir bladders 260, 268 and the articulation of the end effector 232. In addition, other components such as a firing bar 274 passing through a firing bar slot 276 in the frame 252 may be incorporated (FIGS. 17, 19).

As shown in FIGS. 2 and 18-19, lateral movement of C-shaped compression member 272 to the left compresses right proximal reservoir bladder 260 forcing fluid into right fluid passageway 258 and right distal actuating bladder 256. As right distal actuating bladder 256 moves T-bar 240 laterally to the left, the left distal actuating bladder 262 is compressed and the end effector 232 is articulated to the right (clockwise as viewed from the top as shown). Compression of the left distal actuating bladder 262 causes fluid to flow proximally through the left fixed fluid passageway 264 and into left proximal reservoir bladder 266. In particular, an attached right wall 280 of the C-shaped compression member 272 moves to the left causing compression of the right proximal reservoir bladder 260. A corresponding movement left of an attached left wall 278 of the C-shaped compression member 272 provides space for the fluid from compressed left reservoir bladder 262 as the fluid flows into the expanding left proximal reservoir bladder 266.

This fluid control system 235 for the articulation mechanism 230 offers at least several advantages. First, the orientation of the actuating bladders 256, 262, proximal to the articulation joint or mechanism 230, allows the use of long bladders 236, 238 and longer T-bars 240 within the instrument 234. As a fluid-driven system, increasing the output force of the fluid control system 235 may be accomplished in two ways. First, for a fixed fluid area on the T-bar 240, the fluid pressure onto the fixed area may be increased. Second, for a fixed fluid pressure, the fluid contact area on the T-bar 240 may be increased. The first method results in a more compact design and higher system pressures. The second method results in a larger design and lower system pressures. To decrease cost, simplify the design, reduce system stress, and reduce risk of bladder rupture, the illustrative version depicts long distal actuating bladders 256, 262 in an advantageous position proximal to the articulation mechanism 230 within an elongate shaft of the instrument. It is this placement of the bladders 256, 262 that enable the bladders 256, 262 to be long and the articulation output force to be high for a low input pressure.

Thus, the output force of the articulation mechanism 230 can be increased (for the same input pressure) simply by increasing the pressure contact area of the distal balloons 256, 262 on T-bar 240. Pressure contact area increases are restricted to height and length. Since the diameter of conventional endoscopic surgical instruments are fixed at certain diameters to pass through insufflation ports, this limits the height change. Changing the length of the pressure contact area has the greatest effect and enables the lateral output force of the device to be advantageously tuned (by changing length) to meet whatever output force the system requires.

Fluids used in a laterally moving device can be either compressible or incompressible. As used herein, the term "fluid" comprises liquids, gases, gels, microparticles, and any other material which can be made to flow between a pressure gradient. While any fluid can be used, sterilized solutions such as saline, mineral oil or silicone are especially preferred.

Laterally Moving Mechanical Articulation Mechanism

Figure 20:
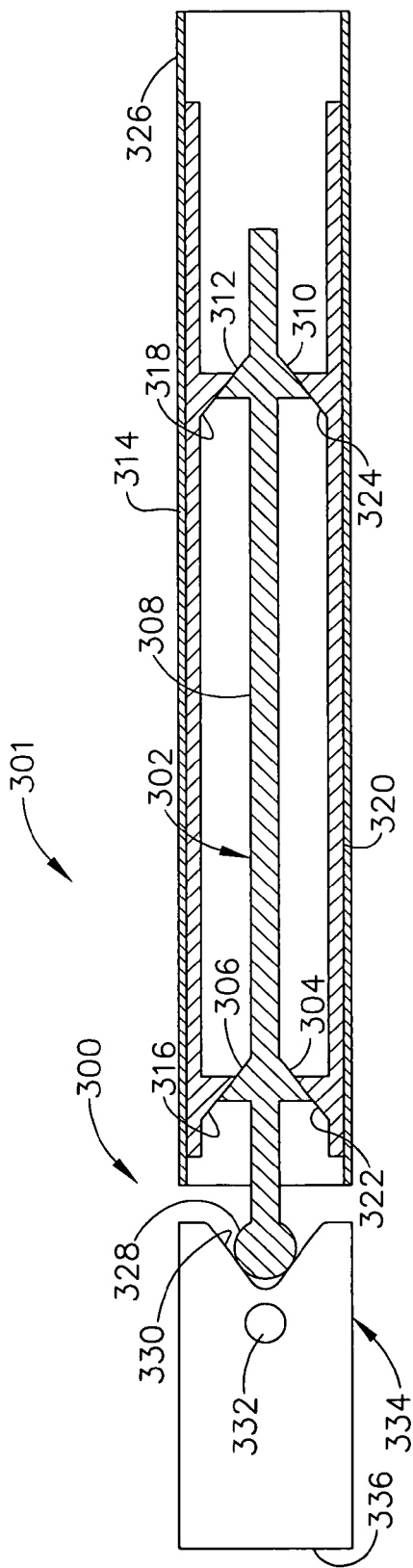
FIG. 20 is a top diagrammatic view of a surgical instrument articulated by at least one longitudinally moving member that laterally cams a slide bar, which in turn articulates an end effector.
Figure 21:
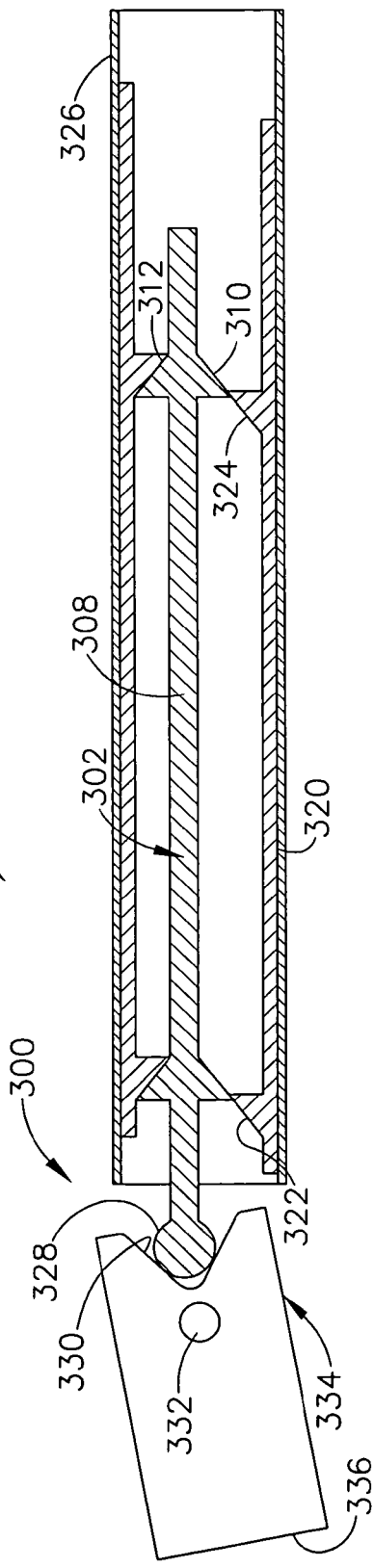
FIG. 21 is a top diagrammatic view of the surgical instrument of FIG. 20 in an articulated state.

Whereas fluid mechanisms are described above to cause lateral movement and articulation, mechanical mechanisms may accomplish a similar lateral motion as produced by the fluid bladders 206, 208. In FIGS. 20-21, an alternate laterally moving articulation mechanism 300 employs a mechanical control system, in particular a longitudinally moving member, to affect lateral motion and articulation for a surgical instrument 301. In the illustrative version, with particular reference to FIG. 20, a laterally moving slide bar 302 has at least one pair of angled left and right cam surfaces 304, 306 extending laterally therefrom on opposite sides of an elongate longitudinal shaft 308. In the illustrative version, another pair of proximal left and right angled cam surfaces 310, 312 are also included. A right longitudinally moving link 314 includes corresponding inwardly directed distal and proximal counter ramped surfaces 316, 318 that register and slidingly engage to distal and proximal right cam surfaces 306, 312 such that distal longitudinal movement of the moving link 312 causes leftward lateral movement of the slide bar 302. It should be appreciated that this ramping contact may be reversed such that distal movement causes rightward movement respectively.

It should be appreciated that a spring bias (not shown) may be included on the slide bar 302 to urge the slide bar 302 rightward into engagement with the right longitudinally moving link 314 so that the opposite proximal movement of the right longitudinal moving link 314 causes leftward movement of the slide bar 302. Alternatively, in the illustrative version, a left longitudinally moving link 320 includes corresponding inwardly directed distal and proximal counter ramped surfaces 322, 324 that register and slidingly engage to distal and proximal right cam surfaces 304, 310 so that distal longitudinal movement of the left longitudinally moving link 320 causes rightward lateral movement of the slide bar 302. It should be appreciated that this ramping contact may be reversed such that proximal movement causes leftward movement. It should be appreciated that the right and left longitudinally moving links 314, 320 and sliding bar 302 are supported within an elongate shaft 326 that allows this longitudinal movement of the former and lateral movement of the latter.

A distal end of the slide bar 302, depicted as a socket ball 328, is received within a V-shaped cam groove 330 proximally aligned and proximal to a pivot pin 332 of an end effector 334. Thus, in FIG. 2 1, proximal movement of the right longitudinally moving link 314 and distal movement of the left longitudinally moving link 320 causes rightward movement of the sliding bar 302 with a corresponding rightward movement of the socket ball 328. Thus, the V-shaped cam groove 330 is driven rightward, pivoting its most distal end 336 to the left. Alternatively, lateral movement of the slide bar 302 may be converted to articulation of the end effector 334 by the rack and gear engagement described above with respect to FIGS. 16-19. Thus, mechanical systems that use longitudinal movement can be used to provide lateral articulation for the surgical instrument 301.

Rotatable Link

Figure 23:
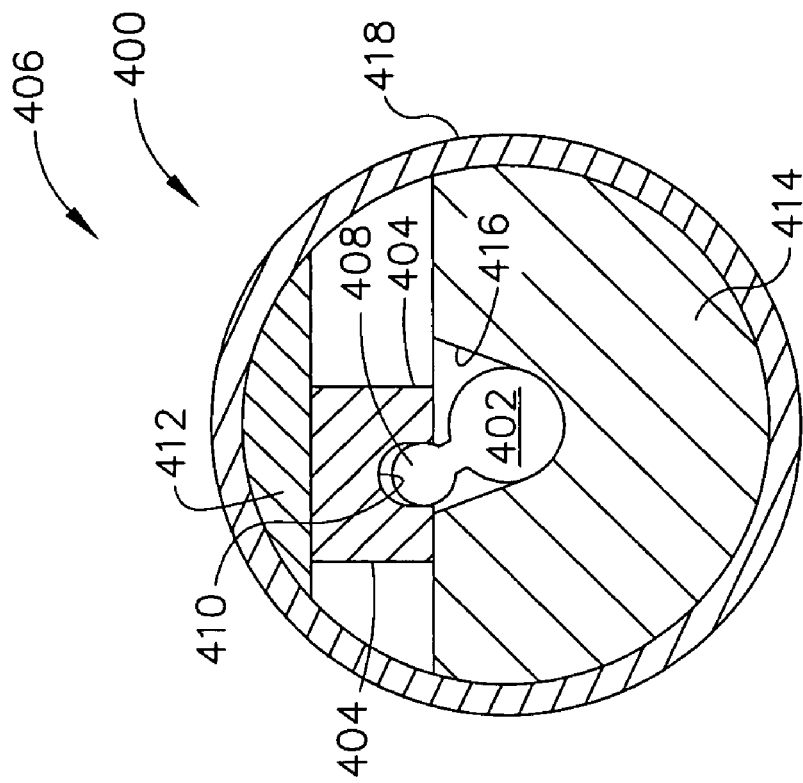
FIG. 23 is a front cross-section view in elevation of the alternative rotary link mechanical control system of FIG. 22 in an articulated state.
Figure 22:
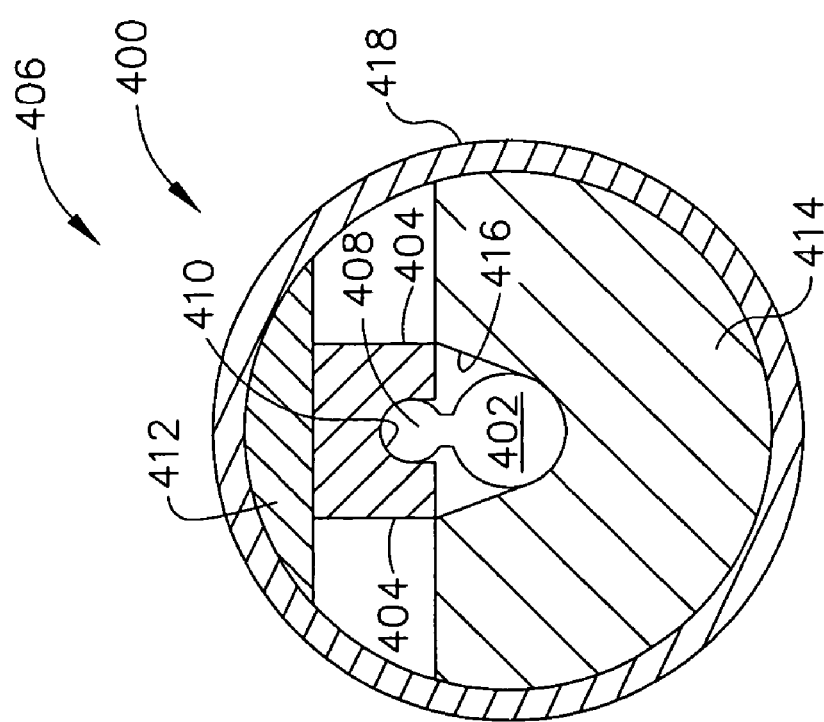
FIG. 22 is front, cross-section view in elevation of an alternative rotary link mechanical control system for a surgical instrument of FIG. 16 or 20 for laterally translating respectively a T-bar or slide bar, depicted in an unarticulated state.

In FIGS. 22 and 23, a further alternate articulation mechanism 400 uses a rotatable link 402 to move a lateral member, depicted as laterally moving slide bar 404, to cause articulation for a surgical instrument 406. The laterally moving slide bar 404 may operably engage with a rotary gear or a cammed groove as described above for FIGS. 16 and 20 at a proximal end of an end effector (not shown). Rotatable link 402 may be located below the slide bar 404 with at least one arm 408 extending rotatably transverse to the longitudinal axis therefrom to engage within a socket 410 within the slide bar. The slide bar 404 is vertically constrained between a top spacer 412 and a bottom frame 414, the later having a longitudinal trough 416 that receives the rotatable link 402 and accommodates rotation of the arm 408. The spacer 412 and frame 414 are encompassed by a tubular sleeve 418. Rotation of the rotary link 402 moves the arm 408 in an arc and thereby moves the slide bar 404 laterally in the direction of rotation.

Articulation Mechanism Having Opposing Buckling Flexible Members

In FIG. 24, a surgical instrument 500 has a slide member 502 aligned along a longitudinal axis of an elongate shaft 504 and allows lateral movement between a left buckling member 506 and a right buckling member 508 and is vertically constrained by a frame and spacer (not shown). Each buckling member 506, 508 has a respective fixed distal attachment 510, 512 and a longitudinally translatable proximal link 514, 516. Respective left and right flexible members 518, 520 inwardly bow in opposition against the slide bar 502, with the amount of lateral intrusion in relation to distal longitudinal movement of their respective proximal link 514, 516. In an unarticulated state shown in FIG. 24, the proximal links 514, 516 are not differentially positioned, and thus a distally projecting tip 522 of the slide member 502 is centered within a V-shaped cam groove 524 that proximally opens relative to a pivot pin 526 of an end effector 528. In FIG. 25, the left proximal link 514 has been distally advanced and the right proximal link has been proximally retracted, causing the slide bar 502 to laterally translate to the right, thereby causing camming of the distally projecting tip 522 against a right portion of the V-shaped cam groove 524 with resultant leftward articulation of the end effector 528 about the pivot pin 526.

Electromagnetic Lateral Articulation Control Mechanism

Figure 26:
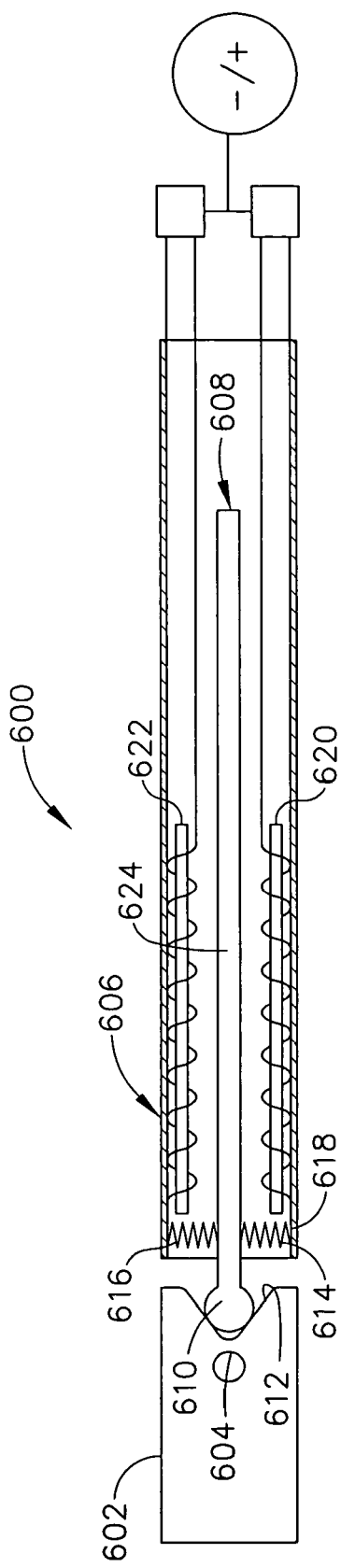
FIG. 26 is a top diagrammatic view of a surgical instrument having an electromagnetic lateral articulation control mechanism.
Figure 27:
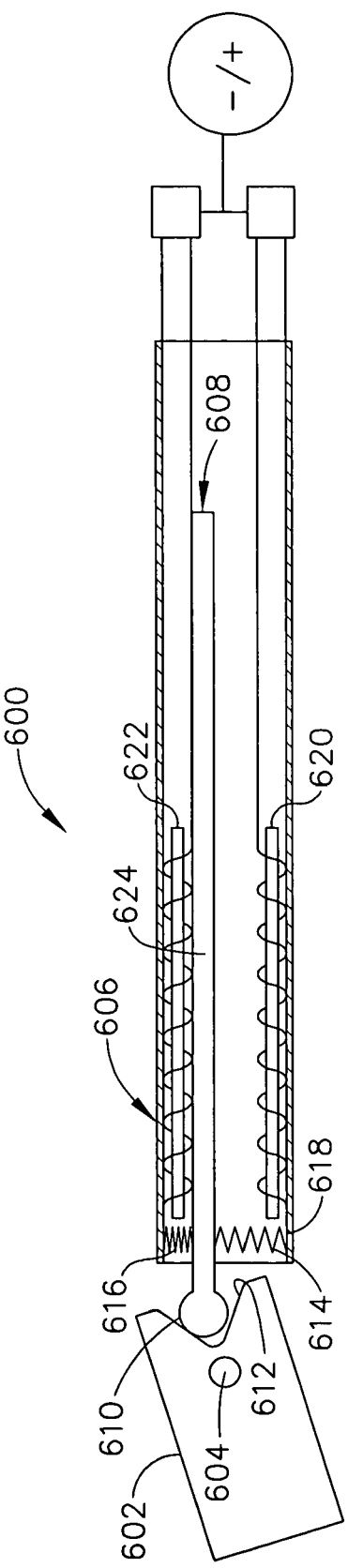
FIG. 27 is a top diagrammatic view of the surgical instrument of FIG. 26 in an articulated state.

In FIG. 26, a surgical instrument 600 has a distally connected end effector 602 that is selectively articulated in an arc about its pivot pin 604 relative to an elongate shaft 606 by lateral motion of a slide bar 608. In particular, a distal socket 610 of the slide bar 608 engages a V-shaped cam groove 612 opening proximal to the pivot pin 604. The slide bar 608 is vertically constrained within the elongate shaft 606 by a frame and spacer (not shown). Left and right compression springs 614, 616 that are inwardly directed on opposite lateral sides of the slide bar 608 are proximate to a distal end 618 of the elongate shaft 606. These springs 614, 616 provide a centering bias on the slide bar 608 and thus on the end effector 602. Left and right electromagnets 620, 622 on opposing sides of the slide bar 608 are selectively activated to attract a ferrous target 624 integral or affixed to the slide bar 608, thereby selectively displace the slide bar 608 laterally and effect articulation of the end effector 602, as depicted in FIG. 27. For simplicity, a longitudinally-aligned coil is depicted, although it should be appreciated that one or more electromagnets may be aligned to produce a magnetic field perpendicular to the slide bar 608, such as a plurality of coils (not shown) aligned along the longitudinal length of the slide bar 608 with each coil having its longitudinal axis aligned with the lateral movement axis of the slide bar 608.

Articulation Control Mechanism with Pressure Source

In FIG. 28, a surgical instrument 700 incorporates an articulation control mechanism 702 that utilizes left and right elongate piston supports 704, 706 that attach laterally on each side of a pivot pin 708 of an end effector 710. A spool valve 712 is slidingly located in bore 713 of valve frame 715 in a proximal portion (e.g., handle) 714 of the surgical instrument 700 and selectively communicates a pressure source (e.g., accumulator, pump, orifice to institutional or portable pressure source) 716. Lateral movement of spool valve 712 allows fluids to flow from pressurized material 718 into one of piston supports 704 or 706. Pressurized material 718 from the pressure source 716 may be fluid or pneumatic. For instance, the spool valve 712 may selectively communicate a hospital vacuum source to one of the elongate piston supports 704, 706, drawing back on the selected side as the other side expands when exposed to atmospheric pressure or is otherwise allowed to expand. It should be appreciated that an incompressible or compressible fluid may be used. Moreover, translating material in each elongate piston support 704, 706 may further include a proximal dynamic spool seal that is acted upon by the pressure source 716. As depicted in FIG. 29, the respective decrease and increase in longitudinal length of the elongate piston supports 704, 706 may result from a piston sliding in an elongate tube or alternately result from elongation of a circumferentially flexible material.

Fluid Bladders

Figure 30:
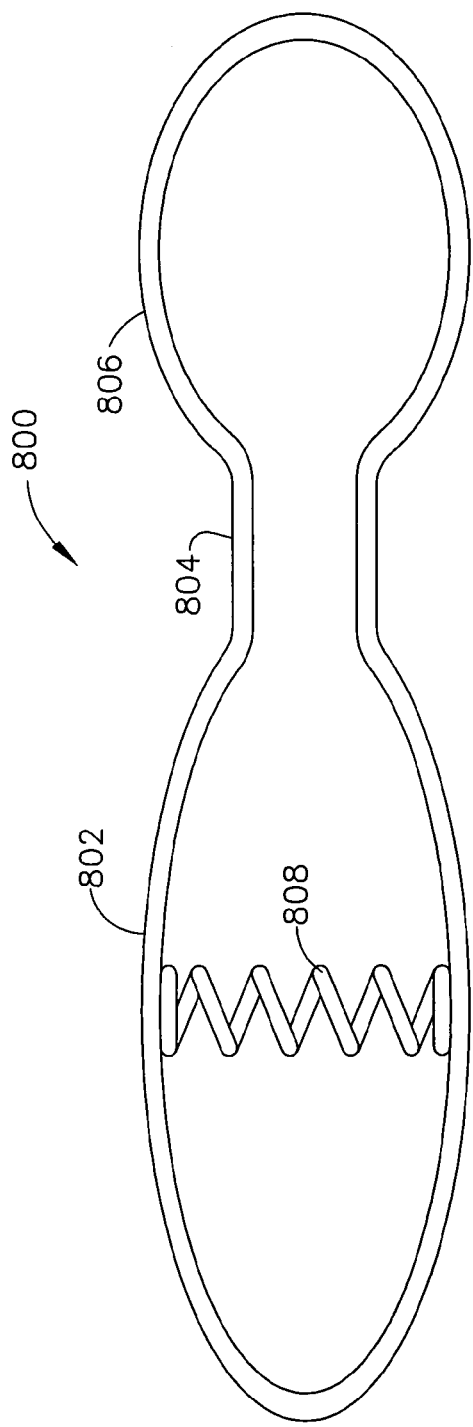
FIG. 30 is a diagrammatic view of a bladder having a lateral compression spring.

In FIG. 30, a bladder 800 is depicted to include an actuating bladder 802 in fluid communication through a fluid passage or conduit 804 to a reservoir bladder 806. In this illustrative version, a compression spring 808 laterally biases the actuating bladder 802 to an expanded state. Advantageous features of incorporation of the compression spring 808 includes providing a restoring force to expand bladder 802 or to center an end effector (not shown), as well as other advantages. If desired, springs can be placed in either one of both bladders 802, 806 or in both bladders 802, 806.

Such a bladder 800 may be constructed in various ways from various combinations of materials. While shown as a unified part above, these bladders 800 may be assembled from multiple parts or constructed as a single unitary fluid bladder 800. For multiple part construction, at least one of the bladders may be attached to any of the other elements. Many leak proof attachment methods are available for assembly such as welding, glue, press fit, heat staking, crimp fittings, clamps fittings, joints and the like. Two basic types of fluid bladders 800 may be constructed. One is a high pressure, non-elastic rigid bladder from either rigid or elastomeric materials, and the other is a lower pressure elastomeric balloon.

Rigid balloon materials are known in the medical art and are used for dilation or angioplasty or the expansion of stents within blood vessel walls. Rigid balloons are made from non-compliant or low compliant materials that retain their designed size and shape under high-pressure loading. Typically, these balloons are thin walled and are formed from high tensile materials with low elongation. Typical materials for these balloons are polyvinyl chloride (PVC), cross linked polyethylene, and polyester (PET) polyethylene terrapthalate, nylon and others. For angioplasty balloons, thin walled sections of PET tubing can be blow molded into a balloon shape. Each of the left and right fluid bladders may be formed from a continuous piece of thin walled tubing with both the proximal and distal bladders formed by expanding local sections of the thin walled tubing. Expansion of the proximal and distal bladder areas can be accomplished by locally heating the tubing and blow molding the bladder shapes therein. One of the open ends of the formed fluid bladders may then be sealed, and the other open end of the bladders may act as a fill port for fluids. After filling, the open fill port is sealed. Alternately, the fluid bladders may be assembled from multiple pieces rather than a single piece. Non-bladder portions of the fluid bladders 800, such as fluid passageways 804, may be formed from rigid or semi-rigid tubing or other materials.

Alternately, elastomeric balloons can also be used to construct fluid bladders 800. These elastomeric materials are formed into a first shape and, with the application of pressure, can expand to a larger shape. Elastomeric materials can expand and return to the original shape a number of times without degradation of elastomeric properties. While not able to handle pressures as high as rigid materials, elastomeric bladders can be used to articulate. Confining or constraining the elastomeric fluid bladders 800 between walls or constraints prevents bulging of bladder material into unwanted areas and increases the forces that can be applied. In FIGS. 16-19, the distal actuating bladders 256 are well constrained between closure sleeve 32, spacer 203, T-bar 230 and frame 34. Elastomeric bladders 210, 220 can be constructed by various processes including dip molding or, like IV bags, formed from two sheets that are welded or glued together. Elastomeric bladders 210, 220 can be formed from latex, rubber, silicone, polyurethane, polyethelene, polypropelene, Teflon, or any one of a number of elastic or semi-elastic engineering materials.

Additionally, conventional blow molding techniques can be used to form bladders 800. Unlike the thin walled PET shrink tubing used in angioplasty balloons, conventional blow molding techniques use a hollow tube or molded hollow preform that is heated and moved to an injection station where low pressure air is typically used to initially inflate the rod or preform. A burst of high-pressure gas is then applied to force the expanded hot tube or preform into contact with the walls of the mold to cool the blown material in the net shape. While producing thin walls, the preform blow molding process produces thin walls that are much thicker than the less than 4 mil angioplasty balloons. This process forms many current products such as soda bottles, disposable pipettes with a rigid tube and expanded bladder, and containers. For the formation of bladders 800, a preform shape is first injection molded with the appropriate material thickness at the expandable bladder areas to provide the desired wall thickness when the bladders are expanded in the blow molding process. Once the bladders are blow molded into net shape, they can be filled with fluid and sealed. Appropriate blow molding materials include nylon, polyester (PET), polyethelene, polyprolelene, high density polyethelene (HDPE) and any one of a number of known blow molding materials.

In addition to rigid and elastomeric bladders, bladder construction may be springy or flaccid. That is, at least one of the proximal bladders or at least one of the distal bladders may be constructed from a spring material that wants to resume its original shape after compression and release. Alternately, at least one of the proximal bladders or at least one of the distal bladders may be constructed from a generally flaccid material with a weak spring rate or, floppy non-rigid materials that won't attempt to expand back to the original pre-deformed shape. Flaccid bladders or springy bladders such as bladder 800 may include the internal compression spring 808 that forces the walls of the bladder 800 outward. The internal compression spring 808 may be formed from a variety of materials including metallic springs, plastic springs, foams, squeezable elastomerics and the like. A sealed assembly of a full flaccid bladder with a partially filled spring bladder (on a passageway) results in the spring bladder expanding and drawing fluid from the flaccid bladder. Assembly of a pair of partially compressed spring bladders (of equal spring rate walls and size) results in both spring bladders being in the partial compressed position. Compression of one of the partially filled spring bladders results in full expansion of the uncompressed spring bladder and reduction of the compressed spring bladder. Release of the compressed spring bladder enables the compressed spring bladder to expand and draw fluid back into the compressed spring bladder. This process is spring rate controlled and if both bladders have the same spring rate, the fluid will be drawn back in to the released compressed spring bladder until both spring bladders are equally filled. If desired, mismatched spring rates for the spring bladders can be used to draw and store fluids into one of the bladders as desired.

Figure 31:
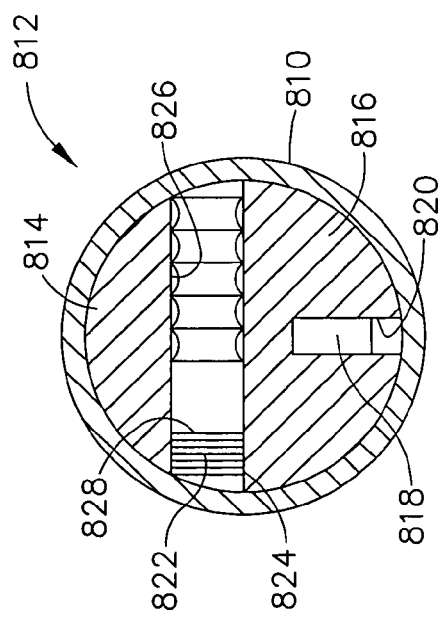
FIG. 31 is a front, cross-section view in elevation of a tubular shaft of the surgical instrument incorporating a pair of collapsible bellows for bladders showing the T-bar in an articulated position and one bellows expanded and one bellows collapsed.

While the proximal reservoir bladders 806 and distal actuating bladders 802 are shown in a rounded rectangular shape, the actual cross sectional shape of the bladder can be modified to be any shape. For example it could be advantageous to construct the distal and/or proximal bladders 802, 806 as a pleated bellows. For instance, a tubular shaft 810 of a surgical instrument 812, as depicted in FIG. 31, has a spacer 814 spaced apart from a frame 816. A firing bar 818 longitudinally translates in a firing bar slot 820 provided in a bottom surface of the frame 816. The left actuating bladder 802 and a right actuating bladder 824 are both of a rectangular pleated design. The right actuating bladder 824 is shown in a compressed state and the left actuating bladder 802 is shown in an expanded state in respective left or right lateral cavity 826, 828 defined between the tubular shaft 810 and a slide bar 830. Pleated right actuating bellows 824 collapse easily into the confined area of the right lateral cavity 826 as depicted. Similarly, pleated left actuating bellows 802 expand easily to fill the area of left lateral cavity 828. While not shown, pleated bladders can also be used for the proximal reservoir bladders 260, 266 of FIGS. 16-19. It should be appreciated that actuating bladders and distal bladders may be easily formed into other cross sectional shapes such as rounds, squares, triangles, hexagons, octagons, or any other shape that meets the needs of the mechanism.

Fluid Transfer Articulation

Whereas the above described lateral fluid mechanism uses bladders and lateral movement to cause articulation, other fluid transfer mechanisms will now be described. These fluid transfer mechanisms illustrate a number of alternate mechanisms of the present invention for transferring fluids from one location to another to effect articulation.

Figure 32:
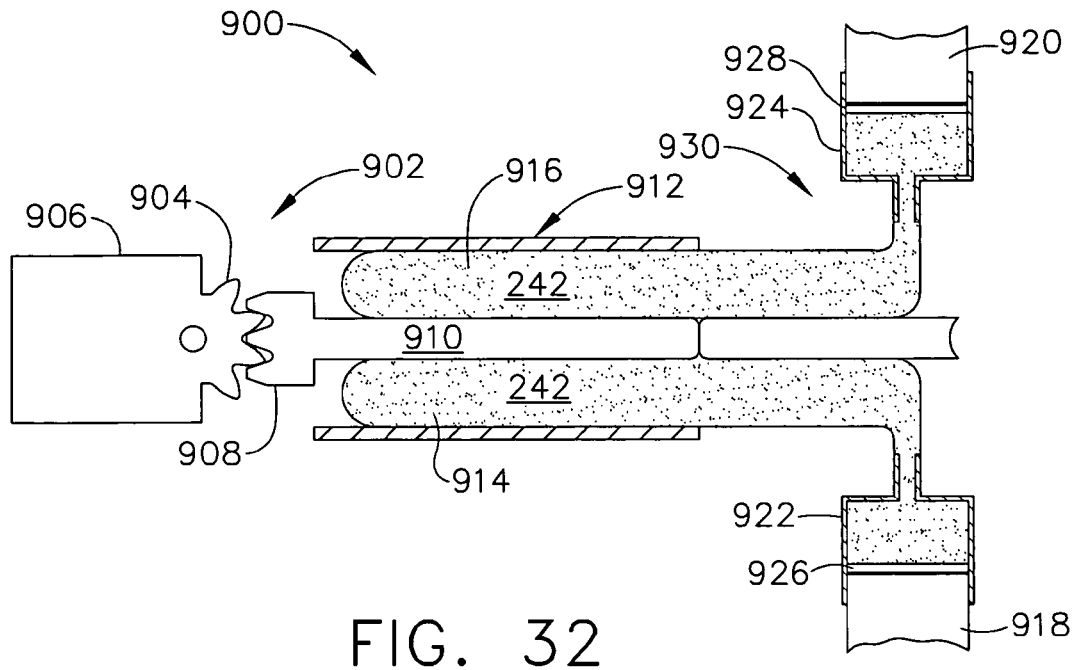
FIG. 32 is a top diagrammatic view of a surgical instrument incorporating fluid transfer articulation of opposing piston-driven bladders on a T-bar that pivots an articulation mechanism.

In FIG. 32, a surgical instrument 900 includes an articulation mechanism 902 containing fluid 242 between a proximally directed gear segment 904 on an end effector 906 that engages a rack 908 on a T-bar 910 that laterally translates with an elongate shaft 912 in response to differential expansion and compression of left and right distal bladders 914, 916. Such compression and expansion is remotely controlled by left and right control pistons 918, 920, which, in the illustrative version, are oriented for lateral movement within respective left and right cylinders 922, 924. Respective left and right dynamic seals 926, 928 make a movable fluid tight seal between the control pistons 918, 920 and their respective cylinders 922, 924.

Figure 33:
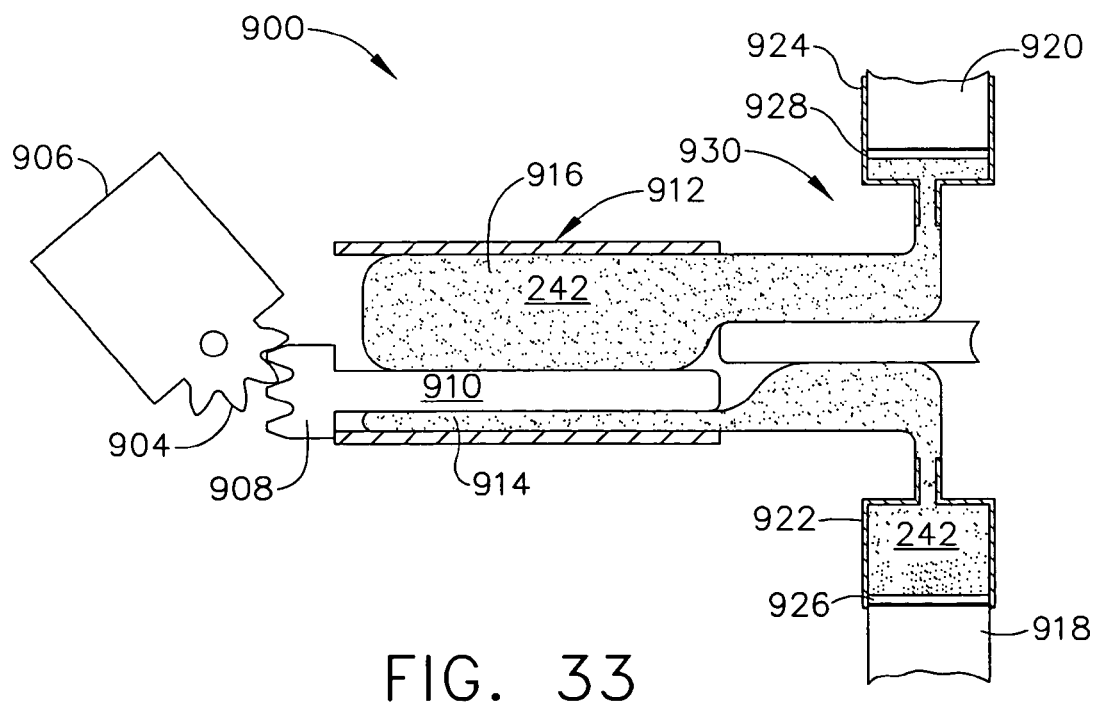
FIG. 33 is a top diagrammatic view of the surgical instrument of FIG. 32 in an articulated state.

A fluid transfer articulation system 930 thus formed moves the articulation mechanism 902 selectively to the right or left. In FIG. 33, the right control piston 920 has been actuated to expand the right distal bladder 916, causing the left distal bladder 914 to compress and extend the left distal bladder 918. With the corresponding leftward movement of the T-bar 910, the rack 908 rotates the gear segment 904 clockwise pivoting the end effector 906 to the right. It should be similarly appreciated that the left control piston 918 may have been pulled, drawing fluid from the left distal bladder 914 or that both control pistons 918, 920 are mechanically coupled to move differentially in concert.

Figure 34:
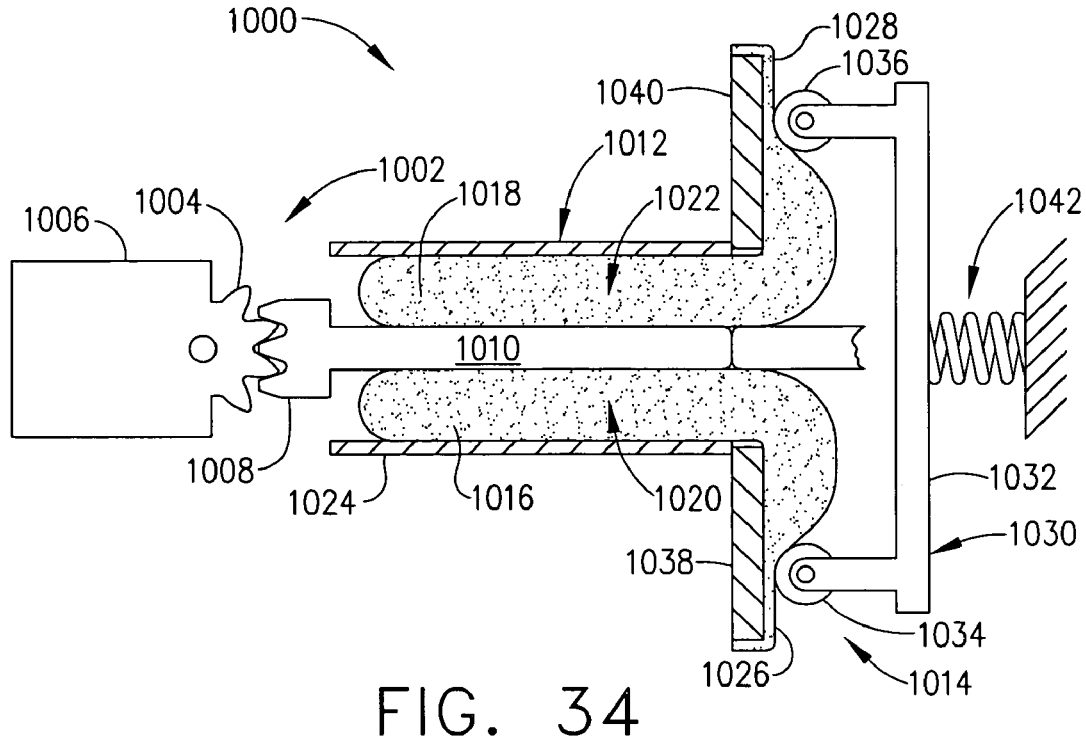
FIG. 34 is a top diagrammatic view of a surgical instrument incorporating fluid transfer articulation of opposing bladders, which are actuated by laterally moving pinch rollers, on a T-bar that pivots an articulation mechanism.

In FIG. 34, a surgical instrument 1000 includes an articulation mechanism 1002 of a proximally directed gear segment 1004 of an end effector 1006 that is engaged to a rack 1008 of a T-bar 1010 that laterally translates within an elongate shaft 1012 in response to a fluid transfer articulation system 1014. In particular, respective left and right distal laterally-operative portions 1016, 1018 of left and right continuous bladders 1020, 1022 are positioned on respective sides of the T-bar 1010 within a closure sleeve 1024 of the elongate shaft 1012. Left and right proximal bladder portions 1026, 1028 are part of a lateral control mechanism 1030. A laterally moving control bar 1032 moves left and right pinch rollers 1034, 1036 that respectively squeeze the left and right proximal bladder portions 1026, 1028 against left and right pinch surfaces 1038, 1040, which may be a hard surface or a resilient surface that deflects from roller contact.

Figure 35:
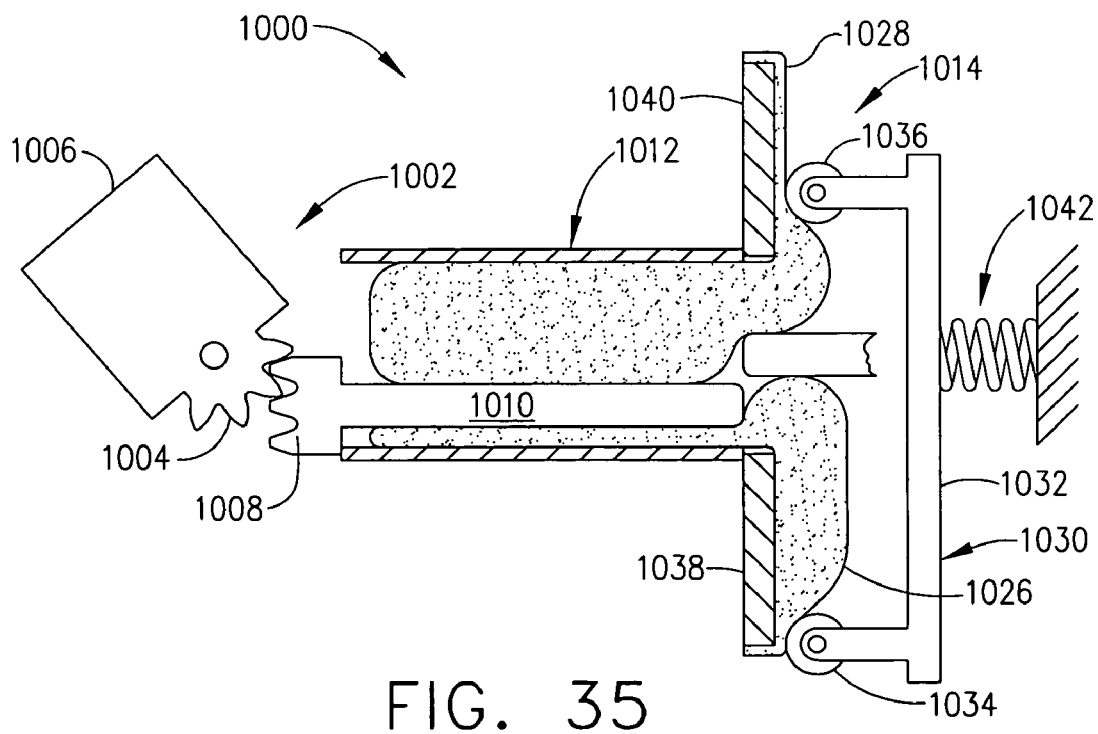
FIG. 35 is a top diagrammatic view of the surgical instrument of FIG. 35 in an articulated state.
Figure 36:
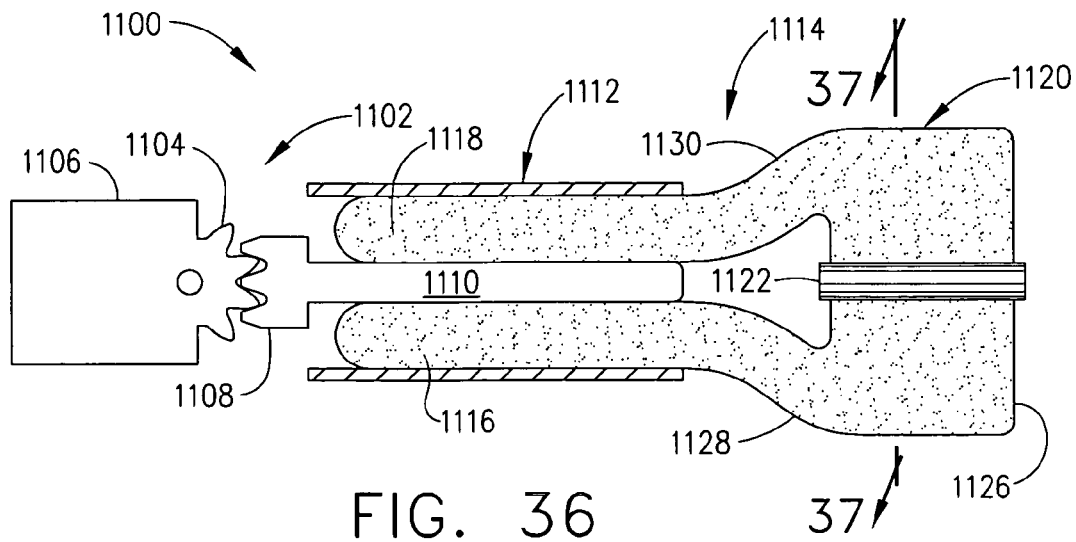
FIG. 36 is a top diagrammatic view of a surgical instrument incorporating a fluid transfer articulation of opposing distal portions of a single bladder differentially actuated by a mid-portion pinch roller.
Figure 37:
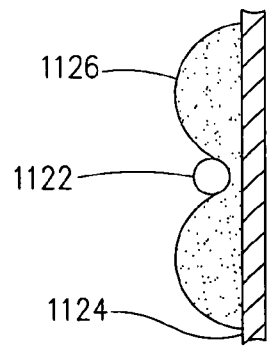
FIG. 37 is a cross-section of the mid-portion pinch roller along lines 37-37 of the surgical instrument of FIG. 36.

Leftward, lateral movement of the laterally moving control bar 1032, depicted in FIG. 35, squeezes fluid from the right proximal bladder portion 1028 into the right distal laterally-operative portion 1018. The expansion of the latter effects leftward lateral movement of the T-bar 1010 and thus rightward articulation of the end effector 1006. Cooperating with this movement, the leftward movement of the left pinch roller 1034 against the left proximal bladder portion 1026 provides space for fluids to flow in from the compressing left distal laterally-operative portion 1016 of the left continuous bladder 1020. One or more springs 1042 urge the laterally moving control bar 1032, and thus the pinch rollers 1034, 1036, toward their respective pinch surfaces 1038, 1040.

Figure 39:
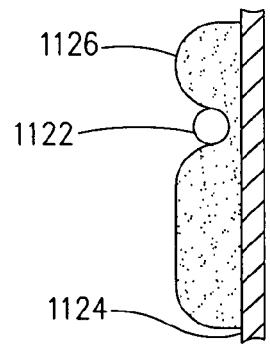
FIG. 39 is a cross-section of the mid-portion pinch roller along lines 39-39 of the surgical instrument of FIG. 38.
Figure 38:
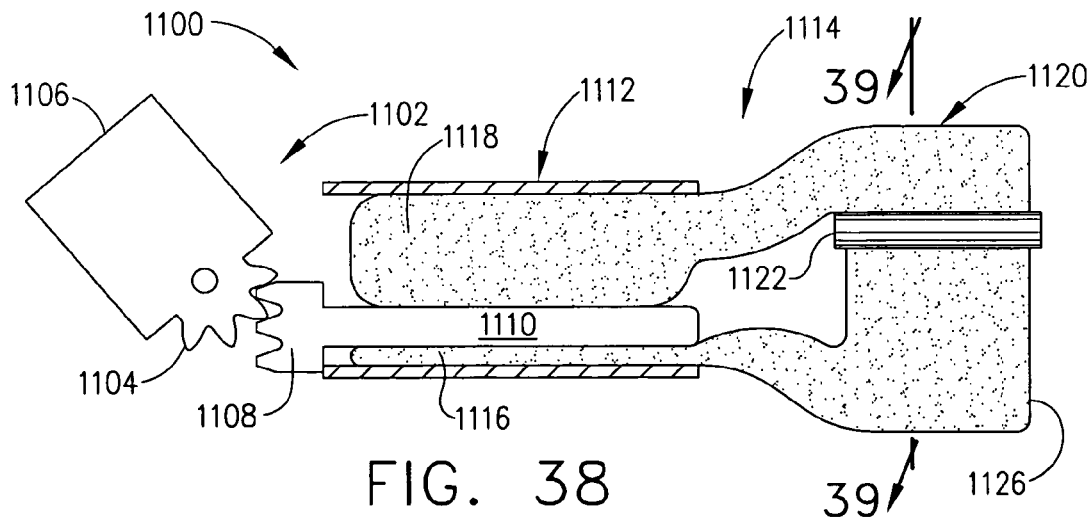
FIG. 38 is a top diagrammatic view of the surgical instrument of FIG. 36 in an articulated state.

In FIGS. 26-27, a surgical instrument 1100 includes an articulation mechanism 1102 of a proximally directed gear segment 1104 of an end effector 1106 that is engaged to a rack 1108 of a T-bar 1110 that laterally translates within an elongate shaft 1112 in response to a fluid transfer articulation system 1114. In particular, respective left and right distal laterally-operative portions 1116, 1118 of a U-shaped bladder 1120 are defined between a mid-point pinch roller 1122 acting against a pinch surface 1124 (e.g., flat surface, opposing pinch roller), thereby effectively separating the U-shaped bladder 1120 into two portions. Differentially forcing fluid from a selected one of the left and right distal laterally-operative portions 1116, 1118 allows the compressive force to transfer fluid into the other. In FIGS. 38-39, the pinch roller 1122 has traversed to the right, expanding the right distal laterally-operative portion 1118 causing leftward movement of the T-bar 1110 and thus rightward articulation of the end effector 1106.

It should be appreciated that the U-shaped bladder 1120 is depicted as having a bladder mid-section 1126, which is traversed by the mid-point pinch roller 1122, that communicates respectively via left and right communicating bladder portions 1128, 1130 to the left and right distal laterally operative portions 1116, 1118, which may comprise rigid conduits or a fluid passage formed in other structural portions of the elongate shaft 1112.

Figure 40:
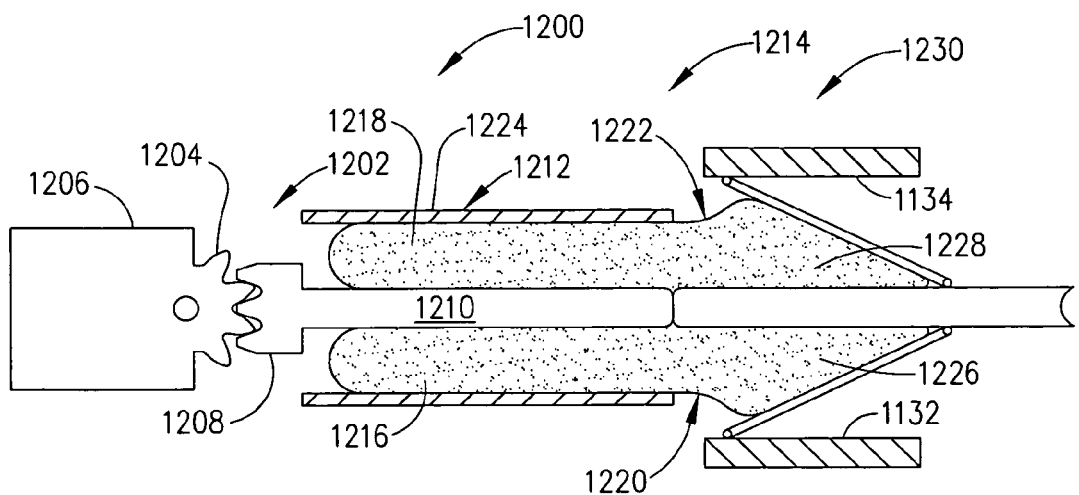
FIG. 40 is a top diagrammatic view of a surgical instrument incorporating a fluid transfer articulation of opposing distal portions of a single bladder differentially actuating bellows compression members.
Figure 41:
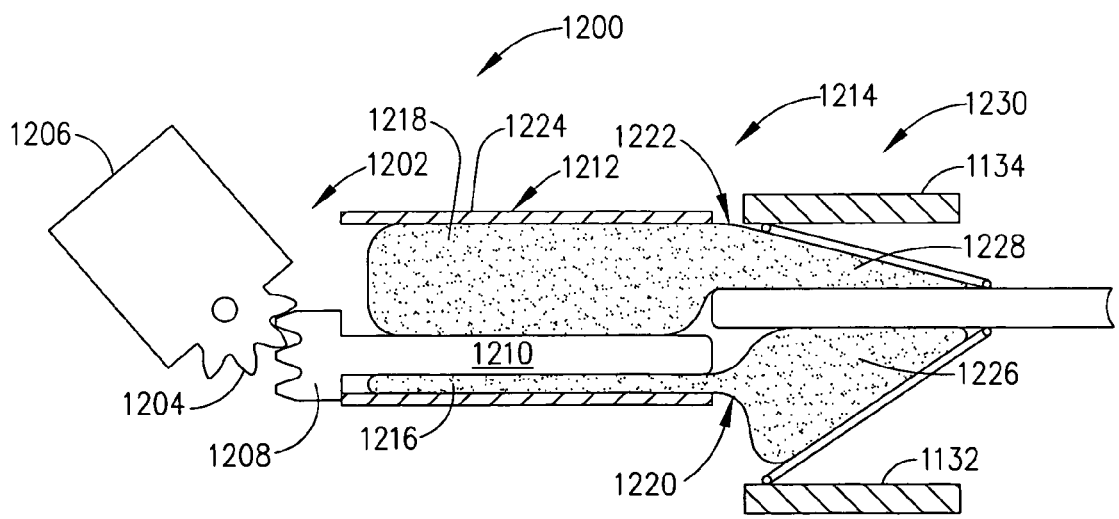
FIG. 41 is a top diagrammatic view of the surgical instrument of FIG. 40 articulated to the right.

In FIG. 40, a surgical instrument 1200 includes an articulation mechanism 1202 of a proximally directed gear segment 1204 of an end effector 1206 that is engaged to a rack 1208 of a T-bar 1210 that laterally translates within an elongate shaft 1212 in response to a fluid transfer articulation system 1214. In particular, respective left and right distal laterally-operative portions 1216, 1218 of left and right continuous bladders 1220, 1222 are positioned on respective sides of the T-bar 1210 within a closure sleeve 1224 of the elongate shaft 1212. Left and right proximal bladder portions 1226, 1228 are part of a lateral control mechanism 1230. In particular, left and right bellows compression members 1232, 1234 compress the left and right proximal bladder portions 1226, 1228 and respectively force fluid into the left and right distal laterally-operative portions 1218. In FIG. 41, the right bellow compression member 1234 is actuated inward, compressing the right proximal bladder portion 1228, expanding thereby the right distal laterally operative portion 1218. Thereby, the T-bar 1210 is laterally moved to the left, articulating the end effector 1206 to the right. In addition, the left distal laterally-operative portion 1216 is compressed, expanding the left proximal bladder portion 1226 and moving the left bellows compression member 1232 outward. Articulating to the left would entail the reverse operation.

Figure 42:
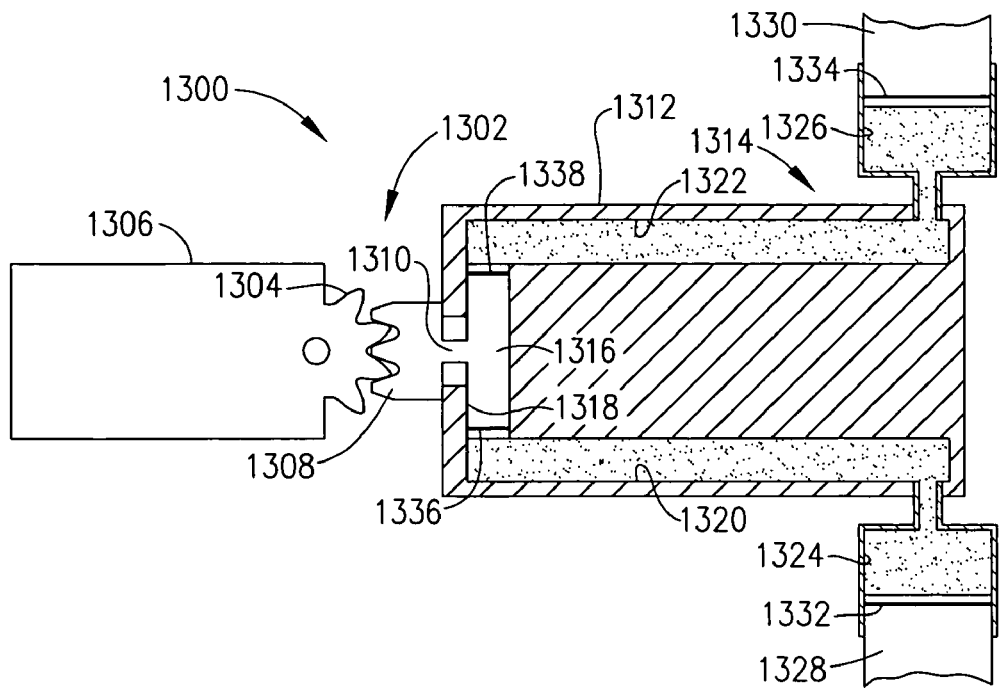
FIG. 42 is a top diagrammatic view of a surgical instrument incorporating a fluid transfer articulation of a T-bar proximally coupled to a lateral spool valve translated by piston displaced fluid movement.
Figure 43:
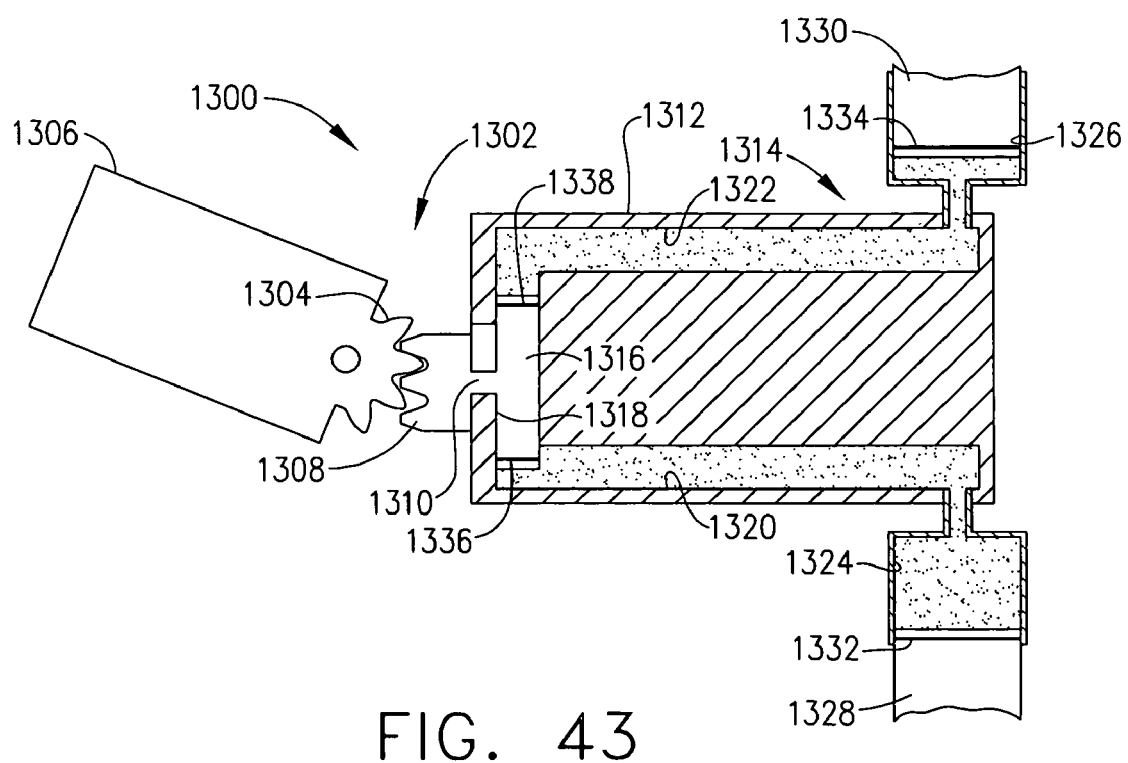
FIG. 43 is a top diagrammatic view of the surgical instrument of FIG. 42 in an articulated state.

In FIG. 42, a surgical instrument 1300 includes an articulation mechanism 1302 of a proximally directed gear segment 1304 of an end effector 1306 which is engaged to a rack 1308 of a T-bar 1310 that laterally translates within an elongate shaft 1312 in response to a fluid transfer articulation system 1314. In particular, a proximal portion of the T-bar 1310 is a spool valve ("distal piston") 1316 formed in a lateral spool bore 1318 that communicates between left and right fluid passages 1320, 1322 formed in the elongate shaft 1312, which in turn communicate to left and right proximal bores 1324, 1326. Left and right proximal pistons 1328, 1330 slide in left and right respective proximal bores 1324, 1326. To prevent fluid loss, proximal seals 1332, 1334 are located respectively on each of the proximal pistons 1328, 1330, and left and right distal seals 1336, 1338 are located respectively on left and right ends of the spool valve 1316. As shown in FIG. 43, lateral movement (to the left) of the right proximal piston 1330 causes lateral movement (to the left) of both the distal piston 1316 and left proximal piston 1328, articulating the end effector 1306 to the right.

In FIG. 44, a surgical instrument 1400 includes an articulation mechanism 1402 that includes a pivotal connection 1404 between an end effector 1406 and an elongate shaft 1408 that is controlled by a fluid transfer articulation system 1410. In particular, left and right fluid bores 1412, 1414 provide fluid communication between proximal and distal ends 1416, 1418 of the elongate shaft 1408. The left fluid bore 1412 terminates respectively at a left proximal cylinder 1420 and a left distal cylinder 1422. The right fluid bore 1414 terminates respectively at a right proximal cylinder 1424 and a right distal cylinder 1426. It should be appreciated that the fluid bores 1412, 1414 may comprise a unitary cylindrical tube or other assembled fluidic components. A left distal piston 1428, sealed by a left distal piston seal 1430, longitudinally translates distally out of the left distal cylinder 1422 into abutment to the end effector 1406 to the left of the pivotal connection 1404. A right distal piston 1432, sealed by a right distal piston seal 1434, longitudinally translates distally out of the right distal cylinder 1424 into abutment to the end effector 1406 to the right of the pivotal connection 1404. A left proximal piston 1436, sealed by a left proximal piston seal 1438, longitudinally translates proximally out of left proximal cylinder 1420 and is coupled to a left-side attachment 1440 to a rotational articulation control actuator 1442. A right proximal piston 1444, sealed by a right proximal piston seal 1446, longitudinally translates proximally out of right proximal cylinder 1422 and is coupled to a right-side attachment 1448 to the rotational articulation control actuator 1442. Left-side fluid 1450 trapped in the left fluid bore 1412 fluidically communicates movement of the left proximal piston 1436 to the left distal piston 1422. Right-side fluid 1452 trapped in the right fluid bore 1414 fluidically communicates movement of the right proximal piston 1444 to the right distal piston 1432. Thus, as in FIG. 45, counterclockwise rotation of the rotational articulation control actuator 1442, as viewed from the top, distally advances the right proximal piston 1444, right-side fluid 1452, and thus the right distal piston 1432 while retracting proximally the left proximal piston 1436, the left-side fluid 1450 and thus the left distal piston 1422. The differential abutment of the distal pistons 1422, 1432 against the end effector 1406 causes leftward articulation. Reversing the rotation of the rotational articulation control actuator 1442 would result in rightward articulation.

Figure 46:
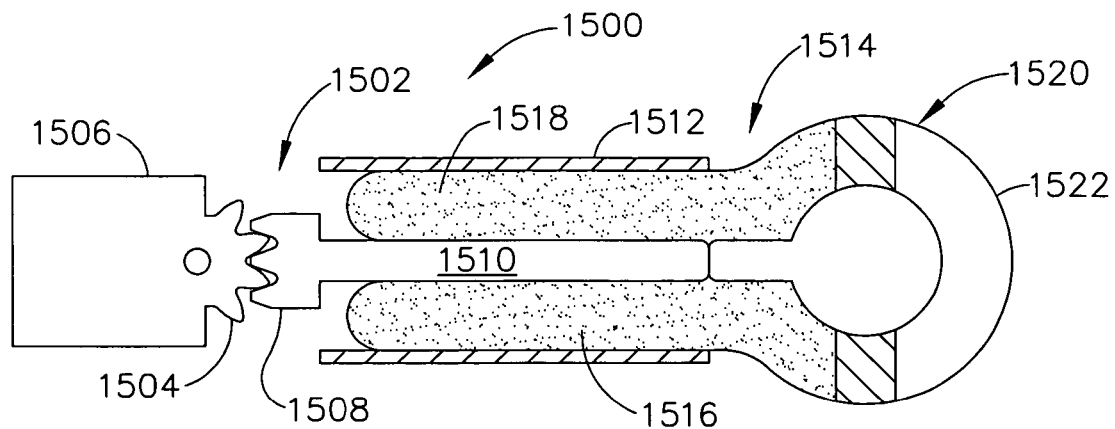
FIG. 46 is a top diagrammatic view of a surgical instrument incorporating a tuning-fork shaped bladder whose distal end laterally translates an articulation mechanism in response to fluid displacement by a mid-portion rotary pump.
Figure 47:
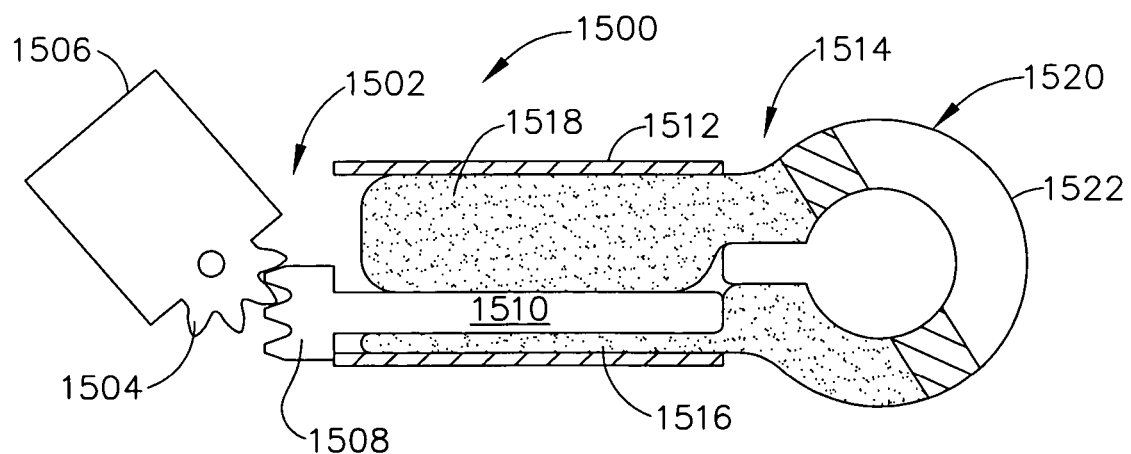
FIG. 47 is a top diagrammatic view of the surgical instrument of FIG. 46 with the rotary pump actuated counterclockwise when viewed from the top to cause rightward articulation of an end effector.

In FIG. 46, a surgical instrument 1500 that includes an articulation mechanism 1502 of a proximally directed gear segment 1504 of an end effector 1506 is engaged to a rack 1508 of a T-bar 1510 that laterally translates within an elongate shaft 1512 in response to a fluid transfer articulation system 1514. In particular, respective left and right distal laterally-operative portions 1516, 1518 are part of a tuning fork-shaped bladder 1520. A rotary pump 1522 acts upon a circular mid-portion 1522 of the tuning fork-shaped bladder 1520, effectively separating the bladder 1520 into two differentially adjustable portions, differentially forcing fluid into a selected one of the left and right distal laterally-operative portions 1516, 1518 while allowing the compressive force to be transferred to the other to force fluid from the other. In FIG. 47, the rotary pump 1522 has rotated counterclockwise as viewed from the top, expanding the right distal laterally-operative portion 1518 causing leftward movement of the T-bar 1510 and thus rightward articulation of the end effector 1506.

Figure 48:
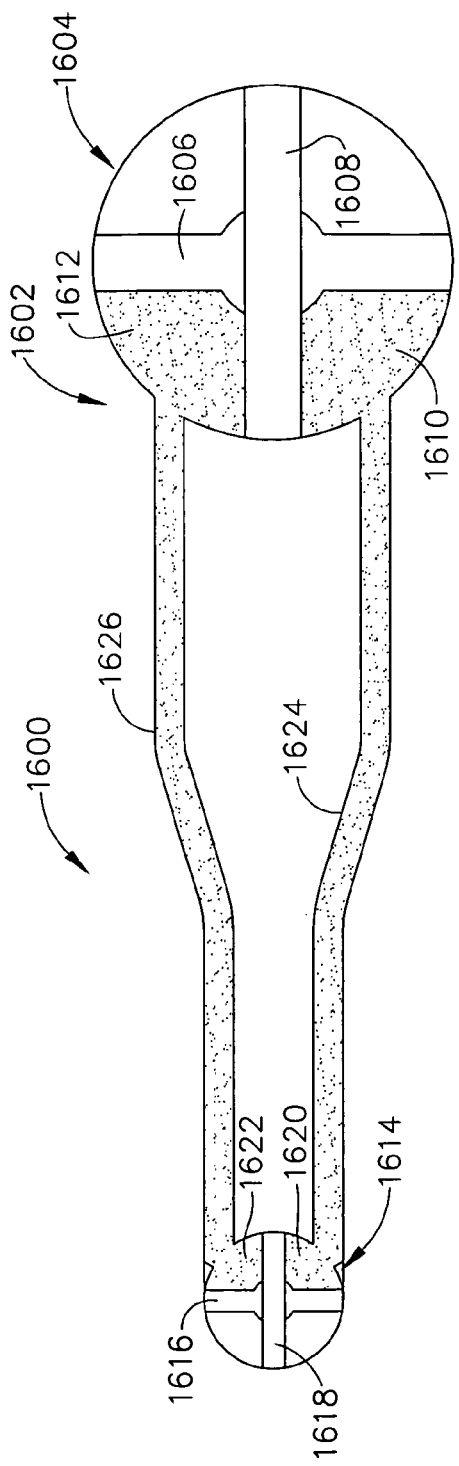
FIG. 48 is a top diagrammatic view of a surgical instrument incorporating fluid transfer articulation mechanism comprised of a two-vane distal turbine differentially and fluidically coupled to a proximal two-vane control.
Figure 49:
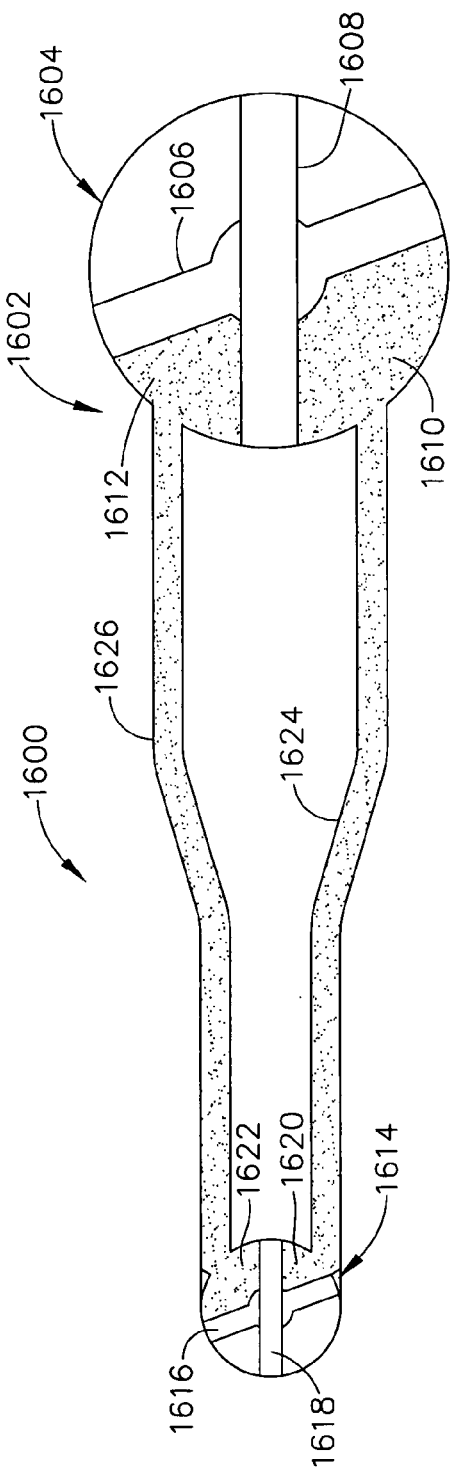
FIG. 49 is a top diagrammatic view of the surgical instrument of FIG. 49 with the proximal two-vane control rotated counterclockwise as viewed from above to cause leftward rotation of an end effector.
Figure 50:
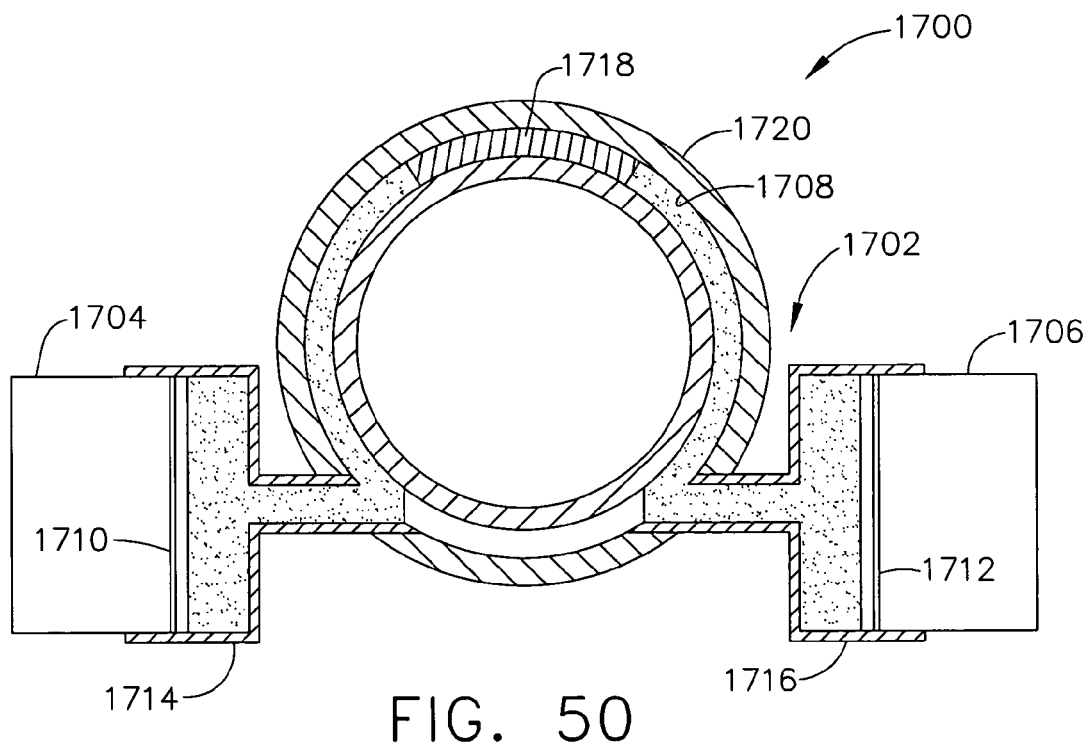
FIG. 50 is back diagrammatic view of a surgical instrument with a fluid transfer articulation mechanism using opposing pistons to create a rotational motion about a circular fluid passage in an elongate shaft.
Figure 51:
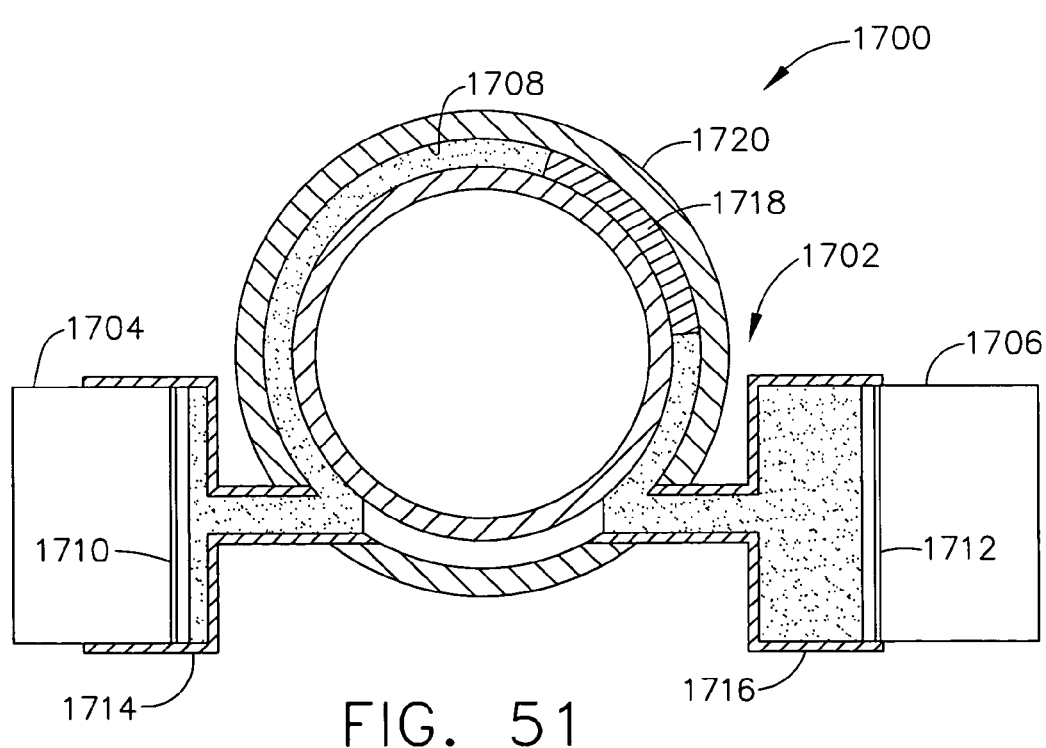
FIG. 51 is a back diagrammatic view of the surgical instrument of FIG. 50 with a rotary member moved clockwise due to a rightward lateral control input.

In FIG. 48, a surgical instrument 1600 includes a fluid transfer articulation system 1602 that includes a proximal cylindrical cavity 1604 that is laterally bisected by a rotary control actuator 1606 and longitudinally bisected by a stationary sealing barrier 1608 to form left and right proximal reservoirs 1610, 1612 that are the two distal compartments of four thus defined. A smaller distal cylindrical cavity 1614 is also similarly bisected by a lateral follower actuator 1616 and longitudinally bisected by a stationary sealing barrier 1618 into four quadrants, with the proximal two being left and right distal compartments 1620, 1622. A left fluid conduit 1624 communicates between the left proximal reservoir 1610 and the left distal compartment 1620 and a right fluid conduit 1626 communicates between the right proximal reservoir 1612 and the right distal compartment 1622. Thus, as depicted in FIG. 49, counterclockwise rotation of the rotary control actuator 1606 reduces the size of the right proximal reservoir 1612 while expanding the left proximal reservoir 1610 with a corresponding reaction at the right and left distal compartments 1622, 1620. An end effector (not shown) that is pivotally coupled to the lateral follower actuator 1616 would thus articulate in response thereto.

In FIG. 40, In FIG. 40, a surgical instrument 1700 incorporates a laterally moving control mechanism 1702 of laterally opposing left and right pistons 1704, 1706 that move in concert such that a rotary fluid flow is produced in a circular fluid passage 1708 that communicates therebetween. In particular, each piston 1704, 1706, which includes a respective left and right piston seals 1710, 1712, is received respectively in a left and right cylinder bore 1714, 1716, the latter in fluid communication by the circularly fluid passage 1708, a portion of which may include a longitudinal fluid passages (not shown). A curved rotary member 1718 is rotated by this differential fluid flow about a longitudinal axis of an elongate shaft 1720 of the surgical instrument 1700. In FIG. 41, rightward lateral movement of the pistons 1704, 1706 causes the rotary member 1718 to move clockwise from the 6 o'clock position to the 8 o'clock position. It should be appreciated that the rotary member 1718 is operably coupled to a rotary drive mechanism (not shown) such as the gear drives described in commonly-owned U.S. Pat. No. 7,110,269 "SURGICAL INSTRUMENT INCORPORATING AN ARTICULATION MECHANISM HAVING ROTATION ABOUT THE LONGITUDINAL AXIS" to Wales et al., filed Jul. 9, 2003, which is hereby incorporated by reference in its entirety.

Tiller Articulation

In FIG. 52, a surgical instrument 2400 includes a tiller articulation mechanism 2402 of a proximally directed tiller 2404 of an end effector 2406 that is pivotally engaged to an elongate shaft 2412 at a vertical pivot pin 2408 presenting a tiller arm 2410 that pivots inside of the elongate shaft 2412 in response to a fluid transfer articulation system 2414. In particular, respective left and right distal laterally-operative portions 2416, 2418 of left and right continuous bladders 2420, 2422 are positioned on respective sides of the tiller arm 2410 within a closure sleeve 2424 of the elongate shaft 2412. Left and right proximal bladder portions 2426, 2428 are part of a lateral control mechanism 2430. In particular, left and right compression members 2432, 2434 compress the left and right proximal bladder portions 2426, 2428 and respectively force fluid into the left and right distal laterally-operative portions 2418. In FIG. 53, the right compression member 2434 is actuated inward, compressing the right proximal bladder portion 2428, expanding thereby the right distal laterally operative portion 2418. Thereby, the tiller arm 2410 is pivoted laterally and moved to the left, articulating the end effector 2406 to the right. In addition, the left distal laterally-operative portion 2416 is compressed, expanding the left proximal bladder portion 2426 and moving the left compression member 2432 outward. Articulating to the left would entail the reverse operation.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For instance, a single fluid transfer approach may be incorporated wherein a single fluid actuator expands and compresses to effect articulation, perhaps assisted by a resilient opposing member that is not in fluid or pneumatic communication to the handle. An application consistent with such a design, for instance, could include just one bladder attached to a T-bar so that when compressed by the withdrawal of fluid, it pulls the T-bar with it.

What is claimed is:

1. A surgical instrument, comprising:
a proximal portion configured for manipulation external to a patient;
an elongate shaft attached to the proximal portion and extending distally therefrom, the elongate shaft defining a longitudinal axis;
an end effector;
an articulation joint attaching the end effector to a distal end of the elongate shaft;
a fluid control attached to the proximal portion operably configured to
a) transfer fluid longitudinally through the elongate shaft through a first fluid passage extending distally from the fluid control, and
b) transfer in an opposite sense fluid longitudinally through a second fluid passage extending distally from the fluid control;
a first fluid actuator distal to the fluid control and in fluid communication with the first fluid passage and responsive to the fluid transferred by the fluid control to articulate the articulation joint;
a second fluid actuator in fluid communication with the second fluid passage and distal to the fluid control, the second fluid actuator responding in an opposite sense to fluid transferred by the fluid control to assist the first fluid actuator to articulate the articulation joint;
an actuating member constrained for lateral movement within the elongate shaft and having a distal end of the actuating member positioned in the articulation joint; and
a proximal surface of the end effector engaged to the distal end of the actuating member for converting a lateral motion of the actuating member to a pivoting motion of the end effector, wherein the first fluid actuator is positioned to a first lateral side of the actuating member in the elongate shaft and the second fluid actuator is positioned to an opposing second lateral side of the actuating member in the elongate shaft and the first fluid actuator and the second fluid actuator move the actuating member laterally to the longitudinal axis in response to the fluid transferred by the fluid control.

2. The articulation instrument of claim 1, wherein the articulation member includes a proximal portion comprising oppositely projecting first and second distal pistons that laterally move within respective first and second distal cylinders that communicate respectively with the first and second fluid passages.

3. The surgical instrument of claim 1, wherein the fluid control comprises:
a first fluid reservoir in communication with the first fluid passage;
a second fluid reservoir in communication with the second fluid passage; and
an articulation control operatively configured to compress a selected one of the first and second fluid reservoirs while allowing the unselected one of the first and second fluid reservoirs to expand in response to compressive forces on the selected one of the first and second fluid reservoirs.

4. The surgical instrument of claim 3, wherein first and second fluid reservoirs comprise respective piston cylinders, the articulation control comprising respective first and second pistons received for movement in the first and second piston cylinders.

5. The surgical instrument of claim 3, wherein the articulation control moves laterally for differentially compressing the first and second fluid reservoirs.

6. The surgical instrument of claim 5 wherein when the articulation control moves in a lateral direction to compress the first fluid reservoir and to expand the second fluid reservoir, a distal tip of the end effector moves at least partially in a lateral direction opposite to that of the articulation control.

7. The surgical instrument of claim 5, wherein the first and second fluid reservoirs comprise respective proximal piston cylinders, the articulation control comprising respective first and second proximal pistons received for movement in the first and second piston cylinders and a rotating control actuator positioned to differentially move the first and second proximal pistons.

8. The surgical instrument of claim 1, wherein the fluid control comprises:
a fluid reservoir in communication with the first fluid passage and the second fluid passage;

a movable sealing surface separating the fluid reservoir into first and second reservoir portions; and a lateral actuator operatively configured to move the movable sealing surface to differentially adjust a fluid volume for each of the first and second reservoir portions.

9. The surgical instrument of claim 8, wherein the lateral actuator comprises a means for differentially adjusting the fluid volume for each of the first and second reservoir portions.

10. The surgical instrument of claim 1, wherein the proximal surface of the end effector comprises a gear segment and the distal end of the actuating member comprises a gear rack.

11. The surgical instrument of claim 10, further comprising a locking member in the elongate shaft selectively, distally and longitudinally translating to engage the gear segment of the end effector for locking the articulation joint.

12. The surgical instrument of claim 11, wherein the locking member is distally biased and includes a proximal pin, the fluid control including a toothed surface that cams the proximal pin proximally during actuation and allows the proximal pin to distally move into a corresponding tooth root of the toothed surface when the fluid control stops.

13. The surgical instrument of claim 1, wherein the first and second fluid actuators comprise respectively first and second distal pistons each engaged to opposing sides of the end effector spaced about a pivot axis thereof.

14. The surgical instrument of claim 13, wherein the fluid control comprises a selector valve operatively configured to couple a selected one of the first and second fluid passages to a pressurized fluid source and to relieve pressure to the unselected one of the first and second fluid passages.

15. The surgical instrument of claim 1, wherein the articulation joint comprises a tiller projecting proximally from the end effector, pivotally received in the elongate shaft, and extending therein to present a tiller arm, the first fluid actuator comprising a first bladder positioned to a first lateral side of the tiller arm in the elongate shaft and the second fluid actuator comprising a second bladder positioned to an opposing second lateral side of the tiller arm in the elongate shaft.

16. The surgical instrument of claim 1, wherein at least a portion of the first fluid actuator moves laterally to the longitudinal axis in response to the fluid transferred by the fluid control.

17. The surgical instrument of claim 1 wherein transferred fluid moves longitudinally in a first direction in the first fluid passage and transferred fluid moves longitudinally in a second direction in the second fluid passage and the first direction is opposite to the second direction.

18. The surgical instrument of claim 1, wherein at least a portion of each of the first fluid actuator and the second fluid actuator moves laterally to the longitudinal axis to articulate the end effector.

19. The surgical instrument of claim 18, wherein at least a portion of the first fluid actuator and at least a portion of the second fluid actuator moves laterally in the same direction to articulate the end effector.

20. The surgical instrument of claim 1, further comprising a first bladder for the first fluid actuator and a second bladder for the second fluid actuator.

21. A surgical instrument, comprising:
a proximal portion configured for manipulation external to a patient;
an elongate shaft attached to the proximal portion and extending distally therefrom, the elongate shaft defining a longitudinal axis and including a first and second fluid passage extending distally through a proximal portion thereof;
an end effector;
an articulation joint attaching the end effector to the elongate shaft;
a fluid control attached to the proximal portion and operably configured to differentially transfer at least one fluid longitudinally therefrom through the elongate shaft via the first and second fluid passages;
a first fluid actuator in fluid communication with the first fluid passage and distal to the fluid control; and
a second fluid actuator in fluid communication with the second fluid passage and distal to the fluid control; and
an actuating member constrained for lateral movement within the elongate shaft and having a distal end of the actuating member positioned in the articulation joint, the distal end engaged to a proximal surface of the end effector for converting a lateral motion of the actuating member to a pivoting motion of the end effector, wherein the first fluid actuator is positioned to a first lateral side of the actuating member in the elongate shaft and the second fluid actuator is positioned to an opposing second lateral side of the actuating member in the elongate shaft and wherein the first and second fluid actuators cooperatively respond to the differential transfer of the at least one fluid to articulate the articulation joint by moving the actuating member laterally to the longitudinal axis in response to the at least one fluid transferred by the fluid control.

22. The surgical instrument of claim 21 wherein the fluid is non-compressible.

23. The surgical instrument of claim 21 wherein the fluid is compressible.

24. A surgical instrument, comprising:
a proximal portion configured for manipulation external to a patient;
an elongate shaft attached to the proximal portion;
an end effector;
an articulation joint attaching the end effector to the elongate shaft;
a fluid control means for bi-directionally transferring a fluid longitudinally through the elongate shaft;
a first fluid actuator and a second fluid actuator located within the elongate shaft distal to the fluid control means and in fluid communication therewith;
an actuating member constrained for lateral movement within the elongate shaft and having a distal end of the actuating member positioned in the articulation joint, the distal end engaged to a proximal surface of the end effector for converting a lateral motion of the actuating member to a pivoting motion of the end effector, wherein the first fluid actuator is positioned to a first lateral side of the actuating member in the elongate shaft and the second fluid actuator is positioned to an opposing second lateral side of the actuating member in the elongate shaft and wherein the first and second fluid actuators cooperatively respond to the differential transfer of fluid from the fluid control means to move the actuating member laterally to the longitudinal axis in response to the fluid transferred by the fluid control means; and
a fluid actuating means distal to the fluid control and responsive to the transferred fluid from the elongate shaft to move the actuating member laterally in response to the fluid transferred by the fluid control means and articulate the articulation joint.

* * * * *